(12) United States Patent
Liu et al.

(10) Patent No.: US 9,738,695 B2
(45) Date of Patent: Aug. 22, 2017

(54) COMPOSITIONS AND METHODS OF USING ISLET NEOGENESIS PEPTIDES AND ANALOGS THEREOF

(71) Applicant: SHENZHEN HIGHTIDE BIOPHARMACEUTICAL, LTD., Shenzhen (CN)

(72) Inventors: Liping Liu, Shenzhen (CN); Ru Bai, Shenzhen (CN)

(73) Assignee: SHENZHEN HIGHTIDE BIOPHARMACEUTICAL, LTD., Shenzhen (CN)

( * ) Notice: Subject to any disclaimer, the term of this patent is extended or adjusted under 35 U.S.C. 154(b) by 0 days.

(21) Appl. No.: 15/177,206

(22) Filed: Jun. 8, 2016

(65) Prior Publication Data

US 2017/0002049 A1 Jan. 5, 2017

Related U.S. Application Data

(63) Continuation of application No. 14/417,110, filed as application No. PCT/CN2014/073483 on Mar. 14, 2014, now Pat. No. 9,388,215.

(30) Foreign Application Priority Data

Mar. 15, 2013 (WO) ................ PCT/CN2013/072771

(51) Int. Cl.

| A61K 38/00 | (2006.01) |
| C07K 14/475 | (2006.01) |
| A61P 29/00 | (2006.01) |
| C07K 7/08 | (2006.01) |
| C07K 14/47 | (2006.01) |
| C07K 7/02 | (2006.01) |

(52) U.S. Cl.
CPC .............. *C07K 14/475* (2013.01); *C07K 7/02* (2013.01); *C07K 7/08* (2013.01); *C07K 14/4705* (2013.01); *C07K 14/4733* (2013.01); *C07K 14/4738* (2013.01); *A61K 38/00* (2013.01)

(58) Field of Classification Search
CPC .... C07K 14/475; C07K 7/08; C07K 14/4733; C07K 14/4738; C07K 7/02; C07K 14/4705; A61K 38/00
See application file for complete search history.

(56) References Cited

U.S. PATENT DOCUMENTS

| 5,804,421 | A | 9/1998 | Vinik et al. |
| 5,834,590 | A | 11/1998 | Vinik et al. |
| 5,935,813 | A | 8/1999 | Hillman et al. |
| 6,492,499 | B1 | 12/2002 | Hillman et al. |
| 6,812,339 | B1 | 11/2004 | Venter et al. |
| 6,824,822 | B2 | 11/2004 | Rickey et al. |
| 7,740,664 | B2 | 6/2010 | Benabdillah |
| 8,012,928 | B2 | 9/2011 | Bluth et al. |
| 8,329,648 | B2 | 12/2012 | Fineman et al. |
| 2002/0009730 | A1 | 1/2002 | Chenchik et al. |
| 2002/0052308 | A1 | 5/2002 | Rosen et al. |
| 2003/0109004 | A1 | 6/2003 | Hillman et al. |
| 2003/0166031 | A1 | 9/2003 | Vinik et al. |
| 2003/0212000 | A1 | 11/2003 | Van Antwerp |
| 2004/0018623 | A1 | 1/2004 | Rosenberg |
| 2004/0018970 | A1 | 1/2004 | Shimkets et al. |
| 2005/0277593 | A1 | 12/2005 | Dieckgraefe et al. |
| 2006/0009516 | A1 | 1/2006 | Rosenberg |
| 2006/0275794 | A1 | 12/2006 | Carrino et al. |
| 2007/0015271 | A1 | 1/2007 | Rosen et al. |
| 2007/0037165 | A1 | 2/2007 | Venter et al. |
| 2007/0072292 | A1 | 3/2007 | Tsang et al. |
| 2007/0087971 | A1 | 4/2007 | Levetan et al. |
| 2007/0184504 | A1 | 8/2007 | Vinik et al. |
| 2008/0171704 | A1 | 7/2008 | Vinik et al. |
| 2008/0300190 | A1 | 12/2008 | Levetan et al. |
| 2009/0142338 | A1 | 6/2009 | Levetan |
| 2009/0183320 | A1 | 7/2009 | Benabdillah |
| 2010/0004213 | A1 | 1/2010 | Abbas et al. |
| 2010/0093605 | A1 | 4/2010 | Levetan et al. |
| 2010/0158809 | A1 | 6/2010 | Bluth et al. |
| 2010/0172922 | A1 | 7/2010 | Hooper et al. |
| 2011/0008887 | A1 | 1/2011 | Tsang et al. |
| 2011/0086770 | A1 | 4/2011 | Wild et al. |
| 2011/0229435 | A1 | 9/2011 | Hooper et al. |
| 2011/0280833 | A1 | 11/2011 | Levetan et al. |

FOREIGN PATENT DOCUMENTS

| CA | 2343602 A1 | 10/2001 |
| CN | 102827253 A | 12/2012 |

(Continued)

OTHER PUBLICATIONS

Exocrine Pancreatic Insufficiency, from http://emedicine.medscape.com/article/2121028-overview, pp. 1-6, accessed Sep. 26, 2016.*
Welsh et al, Stimulation of pancreatic islet beta-cell replication by oncogenes, Proc. Natl. Acad. Sci. USA, 1988, 85, pp. 116-120.*
Pancreatic Islet Transplantation, from NIH, Sep. 2013, pp. 1-12.*
How Is Metabolic Syndrome Treated?, from https://www.nhlbi.nih.gov/health/health-topics/topics/ms/treatment, p. 1, accessed Sep. 26, 2016.*
Vitamins to Promote Nerve Regeneration After Surgery, from http://www.livestrong.com/article/506073-vitamins-to-promote-nerve-regeneration-after-surgery/, p. 1-5, accessed Sep. 26, 2016.*

(Continued)

*Primary Examiner* — Julie Ha
*Assistant Examiner* — Li Ni Komatsu
(74) *Attorney, Agent, or Firm* — Jones Day

(57) ABSTRACT

The invention provides peptides and analogs of INGAP and HIP peptides. The peptides and analogs can be used in methods for treating various diseases and conditions. Such diseases and conditions can include impaired pancreatic function, treating a metabolic disease, for example, diabetes, both type 1 and type 2 diabetes, islets induction, expansion and proliferation for transplantation, promoting neuroprotection or nerve regeneration, promoting liver regeneration or inhibiting inflammation.

16 Claims, 11 Drawing Sheets

(56) References Cited

FOREIGN PATENT DOCUMENTS

| | | |
|---|---|---|
| EP | 1488798 A1 | 12/2004 |
| EP | 2080812 A1 | 7/2009 |
| EP | 2260857 A1 | 12/2010 |
| EP | 2295066 A1 | 3/2011 |
| ES | 2374370 A1 | 2/2012 |
| JP | 2004065120 A | 3/2004 |
| JP | 2006135998 A | 5/2006 |
| KR | 10-2006-0071653 | 6/2006 |
| KR | 10-2006-0089873 | 8/2006 |
| WO | WO 91/16428 A1 | 10/1991 |
| WO | WO 94/15218 A1 | 7/1994 |
| WO | WO 95/00655 A1 | 1/1995 |
| WO | WO 95/11984 A2 | 5/1995 |
| WO | WO 95/27071 A2 | 10/1995 |
| WO | WO 96/26215 A1 | 8/1996 |
| WO | WO 00/55350 A1 | 9/2000 |
| WO | WO 02/40710 A2 | 5/2002 |
| WO | WO 02/48189 A2 | 6/2002 |
| WO | WO 02/056028 A2 | 7/2002 |
| WO | WO 02/059315 A2 | 8/2002 |
| WO | WO 02/070551 A2 | 9/2002 |
| WO | WO 03/016475 A2 | 2/2003 |
| WO | WO 03/020746 A1 | 3/2003 |
| WO | WO 03/033808 A2 | 4/2003 |
| WO | WO 03/034984 A2 | 5/2003 |
| WO | WO 03/057862 A2 | 7/2003 |
| WO | WO 03/059934 A2 | 7/2003 |
| WO | WO 03/095618 A2 | 11/2003 |
| WO | WO 2004/007770 A2 | 1/2004 |
| WO | WO 2004/020588 A2 | 3/2004 |
| WO | WO 2004/092352 A2 | 4/2004 |
| WO | WO 2004/037277 A2 | 5/2004 |
| WO | WO 2004/055519 A2 | 7/2004 |
| WO | WO 2005/031001 A2 | 4/2005 |
| WO | WO 2005/113812 A2 | 12/2005 |
| WO | WO 2005/118615 A1 | 12/2005 |
| WO | WO 2006/128083 A2 | 11/2006 |
| WO | WO 2007/056511 A2 | 5/2007 |
| WO | WO 2007/071437 A2 | 6/2007 |
| WO | WO 2008/011518 A2 | 1/2008 |
| WO | WO 2008/021290 A2 | 2/2008 |
| WO | WO 2008/064306 A2 | 5/2008 |
| WO | WO 2008/079406 A2 | 7/2008 |
| WO | WO 2008/085601 A2 | 7/2008 |
| WO | WO 2008/115525 A2 | 9/2008 |
| WO | WO 2008/118946 A1 | 10/2008 |
| WO | WO 2008/118948 A1 | 10/2008 |
| WO | WO 2009/029847 A1 | 3/2009 |
| WO | WO 2009/049222 A1 | 4/2009 |
| WO | WO 2009/062102 A2 | 5/2009 |
| WO | WO 2009/073565 A2 | 6/2009 |
| WO | WO 2009/097155 A1 | 8/2009 |
| WO | WO 2009/099582 A2 | 8/2009 |
| WO | WO 2009/116861 A2 | 9/2009 |
| WO | WO 2010/033207 A1 | 3/2010 |
| WO | WO 2010/038831 A1 | 4/2010 |
| WO | WO 2010/062663 A1 | 6/2010 |
| WO | WO 2010/091122 A1 | 8/2010 |
| WO | WO 2011/015446 A1 | 2/2011 |
| WO | WO 2011/043834 A1 | 4/2011 |
| WO | WO 2011/084808 A2 | 7/2011 |

OTHER PUBLICATIONS

Foods that help liver regeneration, from http://www.belmarrahealth.com/foods-that-help-liver-regeneration/, pp. 1-8, accessed Sep. 26, 2016.*
Allen et al., "The Cambridge Crystallographic Data Centre: Computer-Based Search, Retrieval, Analysis and Display of Information," Acta Cryst. B 35:2331-2339 (1979).
Anderson, "Human gene therapy," Nature 392(6679 Suppl):25-30 (1998).
Anderson, Incorporation in Neuropeptide Protocols, Brent and Carvell, Eds. 73:49-60 (1997).
Barbosa et al., "Islet neogenesis-associated protein signaling in neonatal pancreatic rat islets: involvement of the cholinergic pathway," J. Endocrinol. 199(2):299-306 (2008) (Epub Sep. 4, 2008).
Berge et al., "Pharmaceutical salts," J. Pharm. Sci. 66(1):1-19 (1977).
Borelli et al., "INGAP-related pentadecapeptide: its modulatory effect upon insulin secretion," Regul. Pept. 131(1-3):97-102 (2005).
Borelli et al., "Transcription, expression and tissue binding in vivo of INGAP and INGAP-related peptide in normal hamsters," Regul. Pept. 140(3):192-197 (2007) (Epub Jan. 19, 2007).
Brugghe et al., "Simultaneous multiple synthesis and selective conjugation of cyclized peptides derived from a surface loop of a meningococcal class 1 outer membrane protein," Int. J. Pept. Protein Res. 43(2):166-172 (1994).
Chang et al., "Targeted expression of islet neogenesis associated protein to beta cells enhances glucose tolerance and confers resistance to streptozotocin-induced hyperglycemia," Mol. Cell. Endocrinol. 335(2):104-109 (2011) (Epub Dec. 25, 2010).
Closa et al., "Pancreatitis-associated protein: from a lectin to an anti-inflammatory cytokine," World J. Gastroenterol. 13(2):170-174 (2007).
Cudic et al., "Pseudopeptide Synthesis via Fmoc Solid-Phase Synthetic Methodology,"Mini-Rev. Organic Chem. 4:268-280 (2007).
Dungan et al., "Effects of therapy in type 1 and type 2 diabetes mellitus with a peptide derived from islet neogenesis associated protein (INGAP)," Diabetes Metab. Res. Rev. 25(6):558-565 (2009).
Dunnett et al., "Neuronal cell transplantation for Parkinson's and Huntington's diseases," Br. Med. Bull. 53(4):757-776 (1997).
Dusetti et al., "Molecular cloning, genomic organization, and chromosomal localization of the human pancreatitis-associated protein (PAP) gene," Genomics 19(1):108-114 (1994).
Dutta, "Small peptides-new targets for drug research," Chem. Br. 25:159-62 (1989).
Francini et al., "Selective effect of INGAP-PP upon mouse embryonic stem cell differentiation toward islet cells," Regul. Pept. 153(1-3):43-48 (2009) (Epub Dec. 30, 2008).
GenBank Accession No. AAB16754 (Translated from: GenBank U41738) ; GI No. 1514684 (Dec. 13, 2001).
GenBank Accession No. AAB24642 (Translated from: GenBank S51768); GI No. 262369 (May 8, 1993).
GenBank Accession No. AAB86497 (Translated from: GenBank U41737); GI No. 1514682 (Mar. 11, 2002).
GenBank Accession No. CAA48605 (Translated from: GenBank X68641); GI No. 312807 (Jun. 30, 1993).
GenBank Accession No. CAD68135 (Translated from: GenBank AX644850); GI No. 28610828 (Feb. 27, 2003).
Gerhard et al., "The status, quality, and expansion of the NIH full-length cDNA project: the Mammalian Gene Collection (MGC)," Genome Res. 14(10B):2121-2127 (2004).
Hermonat et al., "Use of adeno-associated virus as a mammalian DNA cloning vector: transduction of neomycin resistance into mammalian tissue culture cells," Proc. Natl. Acad. Sci. U.S.A. 81(20):6466-6470 (1984).
Itoh et al., "Cloning and tissue-specific expression of cDNAs for the human and mouse homologues of rat pancreatitis-associated protein (PAP)," Biochim. Biophys. Acta 1172(1-2):184-186 (1993).
Kapur et al., "Short-term effects of INGAP and Reg family peptides on the appearance of small β-cells clusters in non-diabetic mice," Islets 4(1):40-48 (2012) (Epub Jan. 1, 2012).
Kent, "Chemical synthesis of peptides and proteins," Ann. Rev. Biochem. 57:957-989 (1988).
Khan et al., "Human fetal liver-derived stem cell transplantation as supportive modality in the management of end-stage decompensated liver cirrhosis," Cell Transplant 19(4):409-418 (2010).
Kopple et al., "Conformations of Cyclic Peptides. VI. Factors Influencing Mono-, 1,4-Di-, and 1,2,4-Trisubstituted Cyclic Hexapeptide Backbones," J. Am. Chem. Soc. 94(3):973-981 (1972).
Langer et al., "Designing materials for biology and medicine," Nature 428(6982):487-492 (2004).

(56) References Cited

OTHER PUBLICATIONS

Langer, "Drug delivery and targeting," Nature 392(6679 Suppl):5-10 (1998).

Lasserre et al., "Structural organization and chromosomal localization of a human gene (HIP/PAP) encoding a C-type lectin overexpressed in primary liver cancer," Eur. J. Biochem. 224(1):29-38 (1994).

Lebkowski et al., "Adeno-associated virus: a vector system for efficient introduction and integration of DNA into a variety of mammalian cell types," Mol. Cell. Biol. 8(10):3988-3996 (1988).

Levetan et al., "Discovery of a human peptide sequence signaling islet neogenesis," Endocr. Pract. 14(9):1075-1083 (2008).

Li et al., "Islet neogenesis-associated protein-related pentadecapeptide enhances the differentiation of islet-like clusters from human pancreatic duct cells," Peptides 30(12):2242-2249 (2009) (Epub Sep. 10, 2009).

Lieu et al., "HIP/PAP accelerates liver regeneration and protects against acetaminophen injury in mice," Hepatology 42(3):618-626 (2005).

Lipsett et al., "β-Cell Neogenesis During Prolonged Hyperglycemia in Rats," Diabetes 51(6):1834-1841 (2002).

Lloyd-Williams et al., "Tetrahedron Report No. 347, Convergent Solid-Phase Peptide Synthesis," Tetrahedron 49:11065-11133 (1993).

Madrid et al., "Islet neogenesis-associated protein pentadecapeptide (INGAP-PP): mechanisms involved in its effect upon beta-cell mass and function," Regul. Pept. Oct. 9, 2009;157(1-3):25-31 (2009) (Epub Jun. 3, 2009).

Merrifield, "Concept and early development of solid-phase peptide synthesis," Methods Enzymol. 289:3-13 (1997).

Merrifield, "Solid Phase Peptide Synthesis. I. The Synthesis of a Tetrapeptide," J. Am. Chem. Soc. 85:2149-2154 (1963).

Orelle et al., "Human pancreatitis-associated protein. Messenger RNA cloning and expression in pancreatic diseases," J. Clin. Invest. 90(6):2284-2291 (1992).

Paula et al., "Requirement of NF-kappaB signalling pathway for modulation of the cholinergic muscarinic $M_3$ receptor expression by INGAP-PP in insulin-producing cells," Eur. J. Pharmacol. 642(1-3):37-46 (2010) (Epup Jun. 10, 2010).

Petropavlovskaia et al., "Development of an in vitro pancreatic tissue model to study regulation of islet neogenesis associated protein expression," J. Endocrinol. 191(1):65-81 (2006).

Rafaeloff et al., "Cloning and sequencing of the pancreatic islet neogenesis associated protein (INGAP) gene and its expression in islet neogenesis in hamsters," J. Clin. Invest. 99(9):2100-2109 (1997).

Ren et al., "Evaluation of in vitro differentiation of human adipose-derived stem cells into islet-like cell clusters induced by INGAP-pp protocol," Journal of Jilin University (Medicine Edition) 36(6):1189-1195 (2010). (English translation of Abstract provided).

Rosenberg et al., "A pentadecapeptide fragment of islet neogenesis-associated protein increases beta-cell mass and reverses diabetes in C57BL/6J mice," Ann. Surg. 240(5):875-884 (2004).

Rosenberg et al., "Islet-cell regeneration in the diabetic hamster pancreas with restoration of normoglycaemia can be induced by a local growth factor(s)," Diabetologia 39(3):256-262 (1996).

Rusinko et al., "Using CONCORD To Construct a Large Database of Three-Dimensional Coordinates from Connection Tables," J. Chem. Inf. Comput. Sci. 29(4):251-255 (1989).

Schlesinger et al., "Alphavirus vectors for gene expression and vaccines," Curr. Opin. Biotechnol. 10(5):434-439 (1999).

Shapiro et al., "Islet transplantation in seven patients with type 1 diabetes mellitus using a glucocorticoid-free immunosuppressive regimen," N. Engl. J. Med. 343(4):230-238 (2000).

Silva et al., "INGAP-PP up-regulates the expression of genes and proteins related to $K^+_{ATP}$ channels and ameliorates $Ca^{2+}$ handling in cultured adult rat islets," Regul. Pept. 148(1-3):39-45 (2008) (Epub Mar. 4, 2008).

Strausberg et al., "Generation and initial analysis of more than 15,000 full-length human and mouse cDNA sequences," Proc. Natl. Acad. Sci. U.S.A. 99(26):16899-16903 (2002) (Epub Dec. 11, 2002).

Tam et al., "INGAP peptide improves nerve function and enhances regeneration in streptozotocin-induced diabetic C57BL/6 mice," FASEB J. 18(14):1767-1769 (2004) (Epub Sep. 2, 2004).

Tam et al., "Islet-neogenesis-associated protein enhances neurite outgrowth from DRG neurons," Biochem. Biophys. Res. Commun. 291(3):649-654 (2002).

Tam et al., "Neurite outgrowth in dorsal root ganglia induced by islet neogenesis-associated protein peptide involves protein kinase A activation," Neuroreport 17(2):189-193 (2006).

Taylor-Fishwick et al., "Cloning genomic INGAP: a Reg-related family member with distinct transcriptional regulation sites," Biochim. Biophys. Acta 1638(1):83-89 (2003).

Taylor-Fishwick et al., "Islet neogenesis associated protein transgenic mice are resistant to hyperglycemia induced by streptozotocin," J. Endocrinol. 190(3):729-737 (2006).

Taylor-Fishwick et al., "Pdx-1 regulation of the INGAP promoter involves sequestration of NeuroD into a non-DNA-binding complex," Pancreas 39(1):64-70 (2010).

Wang et al., "Enhanced islet expansion by β-cell proliferation in young diabetes-prone rats fed a protective diet," J. Cell. Physiol. 224(2):501-508 (2010).

Yatoh et al., "Differentiation of affinity-purified human pancreatic duct cells to β-cells," Diabetes 56(7):1802-1809 (2007) (Epub May 1, 2007).

Ying et al., "Cancer therapy using a self-replicating RNA vaccine," Nat. Med. 5(7):823-827 (1999).

Zha et al., "Effects of islet neogenesis-associated protein pentadecapeptide on cell mass and insulin secretion of pancreatic β-cells," J. Endocrinol. Invest. 35(7):634-639 (2012) (Epub Sep. 23, 2011).

\* cited by examiner

COMPOSITIONS AND METHODS OF USING ISLET NEOGENESIS PEPTIDES AND ANALOGS THEREOF

BACKGROUND OF THE INVENTION

This application is a continuation of application Ser. No. 14/417,110, now U.S. Pat. No. 9,388,215, which is a U.S. national stage application of PCT/CN2014/073483, having an international filing date of Mar. 14, 2014, which claims priority to PCT/CN2013/072771, having an international filing date of Mar. 15, 2013, each of which the entire contents are incorporated herein by reference.

The instant application contains a Sequence Listing which has been submitted electronically in ASCII format and is hereby incorporated by reference in its entirety. Said ASCII copy, created on Jan. 7, 2016, is named 13606-001-999_SL.txt and is 40,868 bytes in size.

The present invention relates generally to the field of medicine and pharmaceuticals, and more specifically to peptide therapies for treating diabetes and other diseases.

Diabetes mellitus (DM) afflicts over 300 million people worldwide. There are two main types of DM: type 1 DM (T1D) and type 2 DM (T2D). T1D results from the body's failure to produce insulin, and requires the patient to administer insulin daily. T2D results from insulin resistance, a condition in which cells fail to use insulin properly. There are many approved non-insulin therapies for T2D. However, there is a large portion of late stage T2D patients requiring insulin administration due to the loss of β-cell function as the disease progresses.

Development of diabetes is associated with substantial losses in pancreatic islet mass. At the time of diagnosis, over 90% of islet mass has been lost in T1D patients, and approximately 50% has been lost in T2D patients. Many attempts have been made in quest of a potential stimulus for islet neogenesis, which is considered as the optimal treatment for both T1D and T2D.

Recently, investigators have shown that islet neogenesis-associated protein (INGAP) from hamster, human proIslet peptide (HIP), glucagon like peptide-1 (GLP-1), islet endocrine neuropeptide vasoactive intestinal peptide (VIP), epidermal growth factor and gastrin, and others, are capable of inducing pancreatic progenitor cells, located in the nonendocrine fraction of the pancreas, to differentiate into fully functional islets in various animal models. Among these compounds, INGAP peptide (INGAP-PP), a 15-mer peptide derived from the sequence of INGAP at amino acids 104-118, has been shown to induce islet neogenesis in multiple animal models, reverse streptozotocin (STZ) induced diabetes in mice, increase C-peptide secretion in T1D patients, and improve glycemic control in T2D patients. Additional biological effects of INGAP-PP have been reported, including dose dependent stimulation of expansion of β-cell mass, β-cell replication, reduced β-cell apoptosis, and increased insulin secretion. In human studies, there was an effect with an improvement of glucose homeostasis, confirmed by HbA1c reduction at 90 days in patients with T2D, and by a significant increase in C-peptide secretion in patients with T1D. However, the short plasma half-life of INGAP-PP and the need for administration in a high dose have significantly limited clinical applications of this peptide.

HIP, the bioactive peptide encoded by a portion of the human regenerating islet-derived 3 alpha (REG3A) gene, is the human homolog of the INGAP peptide. Previous studies have shown that treatment of human pancreatic ductal tissues with HIP stimulated the production of insulin. Administration of HIP improved glycemic control and increased islet number in diabetic mice. The stabilized form of HIP has been tested in a single ascending dose clinical trial with the goal of exploring the tolerability, safety and pharmacokinetics. Like INGAP-PP, high dose is requied of HIP, thus significantly limit clinical applications of the parent HIP peptide.

Thus, there exists a need to develop additional drugs for treatment of diabetes or other diseases associated with impaired pancreatic function. The present invention addresses this need, and provides related advantages as well.

SUMMARY OF INVENTION

The invention provides peptides and analogs of INGAP and HIP peptides. The peptides and analogs can be used for treating various disease and conditions associated with impaired pancreatic function, treating metabolic diseases including diabetes, both type 1 and type 2 diabetes, prediabetes, and metabolic syndrome. The peptides and analogs can also be used for induction of islets, expansion and proliferation for transplantation, promoting neuroprotection, promoting nerve regeneration, promoting liver regeneration, and inhibiting inflammation.

BRIEF DESCRIPTION OF THE DRAWINGS

FIG. 6A: Blood glucose (BG) after 21 day treatment; FIG. 6B: Fasting insulin levels after 21 day treatment; FIG. 6C: Area under curve (AUC) of glucose measured in oral glucose tolerance test (OGTT) after 21 day treatment.

FIG. 9A shows the number of extra islet cluster (EIC) in female C57BL/6J mice after 10 days of treatment. FIG. 9B shows the total area of EIC in female C57BL/6J mice after 10 days of treatment.

FIG. 9C shows representative ductal associated EIC in pancreas after administration of INGAP-PP peptide or INGAP-PP analog.

DETAILED DESCRIPTION OF THE INVENTION

Figure 1:
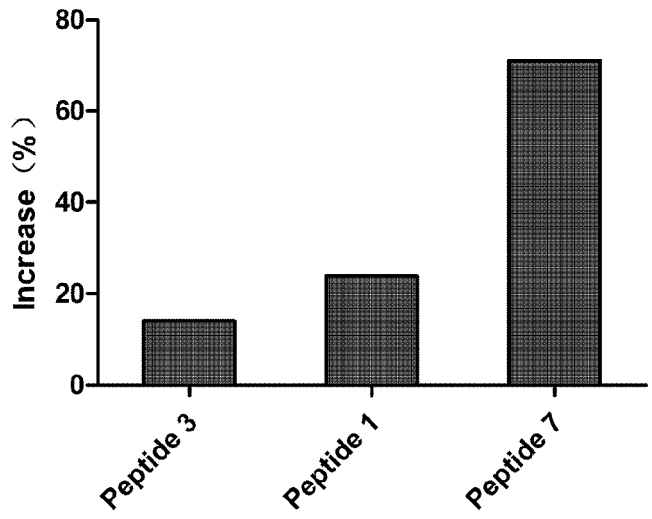
FIG. 1 shows the comparison of ARIP cell (a rat pancreatic ductal cell line) proliferation in the presence of 100 nM of INGAP Scrambled PP 1 (Peptide 3), INGAP-PP (Peptide 1), and a selected peptide analog, Peptide 7 (see Table 2).

The present invention provides compounds, in particular peptide and peptide analogs, that exhibit properties useful for treating a variety of diseases and conditions, particularly diseases and conditions relating to diabetes. The peptides and analogs of the invention are additionally useful for treating impaired pancreatic function, treating metabolic diseases, ex vivo islet induction, expansion and proliferation for transplantation, increasing the survival of transplanted islets in vivo, promoting neuroprotection or nerve regeneration, promoting liver regeneration, and inhibiting inflammation.

As disclosed herein, the present invention provides a series of INGAP-PP and HIP analogs with comparable or improved stability and activities compared to the wild-type peptides (see Tables 2 and 3). The improved pharmaceutical properties of these peptide analogs make them particularly suitable for clinical development. The present invention also provides pharmaceutical compositions comprising a compound according to the present invention and the use of compounds according to the present invention for preparing medicaments for treating metabolic diseases, including but not limited to type 1 diabetes (T1D) and type 2 diabetes (T2D). The invention further provides the compositions of the invention in suitable formulations, including sustained release formulations.

As described previously, a hamster protein was identified that promoted pancreatic islet neogenesis and was termed islet neogenesis associated protein (INGAP) (see U.S. Pat. No. 5,834,590). A pentadecapeptide fragment of INGAP, referred to herein as INGAP-PP, has been described and shown to reverse diabetes in a mouse model (Rosenberg et al., *Ann. Surg.* 240:875-884 (2004); US publication 2006/0009516; see also US publication 2008/0171704; Kapur et al., *Islets* 4:1-9 (2012); Chang et al., *Mol. Cell. Endocrinol.* 335:104-109 (2011); Borelli et al., *Regulatory Peptides* 131:97-102 (2005); Dungan et al., *Diabetes/Metabolism Res. Rev.* 25:558-565 (2009); Zha et al., *J. Endocrinol. Invest.* 35:634-639 (2012); Wang et al., *J. Cell. Physiol.* 224:501-508 (2010); Petropavlovskaia et al., *J. Endocrinol.* 191:65-81 (2006); Taylor-Fishwick et al., *Pancreas* 39:64-70 (2010); Rosenberg, *Diabetologia* 39:256-262 (1996); Madrid et al., *Regulatory Peptides* 157:25-31 (2009); and Taylor-Fishwick et al., *J. Endocrinol.* 190:729-737 (2006)). A human peptide, termed human proIslet peptide (HIP) has also been described (Levetan et al., *Endocrin. Pract.* 14:1075-1083 (2008); US publication 2011/0280833). The present invention provides analogs of INGAP-PP and HIP peptides, including but not limited to those listed in Tables 2 and 3 or others disclosed herein, including the formulas disclosed herein, that are not parent INGAP-PP or HIP peptides. The peptides and analogs of the inventioin exhibit unexpected and beneficial properties over the parent INGAP-PP or HIP peptides.

As used herein, the term "peptide" refers to a polymer of two or more amino acids. The peptide can be modified to include analogs, derivatives, functional mimetics, pseudopeptides, and the like, so long as the peptide comprises a polymer of at least two amino acids. The meaning of the term "peptide" is well known to those skilled in the art. In general, a peptide includes two or more amino acids joined by an amide bond between the carboxyl group of one amino acid residue and the amino group of the adjacent amino acid residue. As described herein, a peptide can comprise naturally occurring amino acids or non-naturally occurring amino acids.

As used herein, the term "analog" refers to a variant of a parent molecule, for example, a parent peptide. For example, an analog of a parent peptide can include a variant, where one or more amino acids are substituted relative to the parent peptide. An analog can also include a modification of a parent peptide, including but not limited to, non-naturally occurring amino acids, D amino acids, modified amino- and/or carboxy-terminal (N- or C-terminal) amino acids, in particular modifications of the amino group on the N-terminus and/or modification of the carboxyl group in the C-terminus, fatty acid modifications, esterification, peptidomimetics, pseudopeptides, and the like, as disclosed herein. Exemplary modifications are described in more details below.

As used herein, the phrase "impaired pancreatic function" refers to a disease or condition associated with the pancreas, where the pancreas exhibits a decreased function compared to that of a normal or healthy individual. Exemplary diseases or conditions associated with impaired pancreatic function include, but are not limited to, type 1 diabetes, type 2 diabetes, latent autoimmune diabetes in adults (LADA), impaired fasting glucose, impaired glucose tolerance, insulin deficiency, fasting hyperinsulinemia, insulin resistance, impaired fasting insulin levels, partial pancreatomy due to injury or inflammation, or a combination thereof. Such diseases and conditions are discussed in more details below.

As described herein, the invention provides peptide analogs of INGAP-PP and HIP peptides. Table 1 shows the sequence of INGAP-PP and HIP peptides, as well as various scrambled versions of the peptides that are used as negative controls in experiments described herein or can be used as negative controls in comparative studies with INGAP-PP, HIP or the peptides analogs of the invention.

TABLE 1

INGAP-PP and HIP Peptides and Control Scrambled Peptides.

| Peptide ID/SEQ ID NO | Sequence |
| --- | --- |
| 1 | H-IGLHDPSHGTLPNGS-OH |
| 2 | H-IGLHDPTQGTEPNGE-OH |
| 3 | H-SHPNG SGTIG LHDPL-OH |
| 4 | H-SSTGG GDIPP HLLHN-OH |
| 5 | H-DGGTP QPGNW IELTH-OH |

As described herein, various analogs of INGAP-PP are provided as peptides or analogs of the invention. Exemplary INGAP-PP peptide analogs of the invention are provided in Table 2.

TABLE 2

Exemplary INGAP-PP Analogs.

| Peptide ID/SEQ ID NO | Sequence |
| --- | --- |
| 1 | H-IGLHDPSHGTLPNGS-OH |
| 6 | H-IGLHAPSHGTLPNGS-OH |
| 7 | H-IGLHDPSHGTLPAGS-OH |
| 8 | H-IGLHAPSHGTLPAGS-OH |
| 9 | H-IGLHDPSHGTLPAGSK-OH |
| 10 | H-IGLHDPSHGTLP(Aib)GS-OH |
| 11 | H-IGLHDPSHGTLP(N-methyl-L-Alanine)GS-OH |
| 12 | Ac-IGLHDPSHGTLPAGS-OH |
| 13 | H-(D-Isoleucine)GLHDPSHGTLPAGS-OH |
| 14 | H-(L-NorValine)GLHDPSHGTLPAGS-OH |
| 15 | H-(L-NorLeucine)GLHDPSHGTLPAGS-OH |
| 16 | Ac-IGLHDPSHGTLPNGS-OH |
| 17 | H-(D-Isoleucine)GLHDPSHGTLPNGS-OH |
| 18 | H-IGLHDPSHGTEPNGS-OH |
| 19 | H-IGLHDPSQGTLPNGS-OH |
| 20 | H-IGLHDPTHGTLPNGS-OH |
| 21 | H-IGLHDPSHGTLPNGE-OH |
| 22 | H-IGLHDPSHGTLPNGK-OH |
| 23 | H-IGLHDPSHGTLPAGK-OH |
| 24 | H-IGLHDPSHGTEPAGS-OH |
| 25 | H-IGLHDPSQGTLPAGS-OH |
| 26 | H-IGLHDPTHGTLPAGS-OH |
| 27 | H-IGLHDPSHGTLPAGE-OH |
| 28 | H-IGLHDPSHGTLPAG-NH2 |

TABLE 2-continued

Exemplary INGAP-PP Analogs.

| Peptide ID/SEQ ID NO | Sequence |
| --- | --- |
| 29 | Ac-IGLHDPSHGTLPAGS-NH2 |
| 30 | Ac-IGLHDPSHGTLPAG-NH2 |
| 31 | Ac-IGLHDPSHGTLPNGS-NH2 |
| 32 | H-IGLHDPSHGTLPNGS-NH2 |
| 33 | H-IGLHDPSHGTLPNGSC-OH |
| 34 | Ac-IGLHDPSHGTLPNGSC-OH |
| 35 | H-IGLHDPSHGTLPNGSC-NH2 |
| 36 | Ac-IGLHDPSHGTLPNGSC-NH2 |
| 37 | H-IGLHDPSHGTLPNGC-OH |
| 38 | Ac-IGLHDPSHGTLPNGC-OH |
| 39 | H-IGLHDPSHGTLPNGC-NH2 |
| 40 | Ac-IGLHDPSHGTLPNGC-NH2 |
| 41 | H-IGLHDPSHGTLPAGS-NH2 |
| 42 | H-IGLHDPSHGTLPAGSC-OH |
| 43 | Ac-IGLHDPSHGTLPAGSC-OH |
| 44 | H-IGLHDPSHGTLPAGSC-NH2 |
| 45 | Ac-IGLHDPSHGTLPAGSC-NH2 |
| 46 | H-IGLHDPSHGTLPAGC-OH |
| 47 | Ac-IGLHDPSHGTLPAGC-OH |
| 48 | H-IGLHDPSHGTLPAGC-NH2 |
| 49 | Ac-IGLHDPSHGTLPAGC-NH2 |
| 73 | IGLHDPSHGTLPAG |
| 74 | IGLHDPSHGTLPNG |
| 75 | Ac-IGLHDPSHGTLPNG |
| 76 | IGLHDPSHGTLPNG-NH2 |
| 77 | Ac-IGLHDPSHGTLPNG-NH2 |
| 78 | H-IGLHDPSHGTLPQGS-OH |
| 79 | H-IGLHDPSHGTLPDGS-OH |
| 80 | H-IGLHDPSHGTLPEGS-OH |
| 81 | H-IGLHEPSHGTLPNGS-OH |
| 82 | H-IGLHQPSHGTLPNGS-OH |
| 83 | H-IGLHNPSHGTLPNGS-OH |
| 84 | H-IGLHEPSHGTLPAGS-OH |
| 85 | H-IGLHQPSHGTLPAGS-OH |
| 86 | H-IGLHNPSHGTLPAGS-OH |
| 87 | H-IGLHDPSHGTLPQGSC-OH |
| 88 | H-IGLHDPSHGTLPDGSC-OH |

TABLE 2-continued
Exemplary INGAP-PP Analogs.

| Peptide ID/SEQ ID NO | Sequence |
| --- | --- |
| 89 | H-IGLHDPSHGTLPEGSC-OH |
| 90 | H-IGLHEPSHGTLPNGSC-OH |
| 91 | H-IGLHQPSHGTLPNGSC-OH |
| 92 | H-IGLHNPSHGTLPNGSC-OH |
| 93 | H-IGLHDPSHGTLPQG-OH |
| 94 | H-IGLHDPSHGTLPDG-OH |
| 95 | H-IGLHDPSHGTLPEG-OH |
| 96 | H-IGLHEPSHGTLPNG-OH |
| 97 | H-IGLHQPSHGTLPNG-OH |
| 98 | H-IGLHNPSHGTLPNG-OH |
| 99 | H-IGLHEPSHGTLPAG-OH |
| 100 | H-IGLHQPSHGTLPAG-OH |
| 101 | H-IGLHNPSHGTLPAG-OH |
| 102 | H-IGLHDPSHGTLPQGE-OH |
| 103 | H-IGLHDPSHGTLPDGE-OH |
| 104 | H-IGLHDPSHGTLPEGE-OH |
| 105 | H-IGLHEPSHGTLPNGE-OH |
| 106 | H-IGLHQPSHGTLPNGE-OH |
| 107 | H-IGLHNPSHGTLPNGE-OH |
| 108 | H-IGLHEPSHGTLPAGE-OH |
| 109 | H-IGLHQPSHGTLPAGE-OH |
| 110 | H-IGLHNPSHGTLPAGE-OH |

As described herein, various analogs of HIP are provided as peptides or analogs of the invention. Exemplary HIP peptide analogs of the invention are provided in Table 3.

TABLE 3
Exemplary HIP Analogs.

| Peptide ID/SEQ ID NO | Sequence |
| --- | --- |
| 2 | H-IGLHDPTQGTEPNGE-OH |
| 50 | H-IGLHDPTQGTEPAGE-OH |
| 51 | H-IGLHDPTQGTEP(Aib)GE-OH |
| 52 | Ac-IGLHDPTQGTEPAGE-OH |
| 53 | H-(D-Isoleucine)GLHDPTQGTEPAGE-OH |
| 54 | Ac-IGLHDPTQGTEPNGE-OH |
| 55 | H-(D-Isoleucine)GLHDPTQGTEPNGE-OH |
| 56 | H-IGLHDPTQGTEPNGS-OH |

TABLE 3-continued
Exemplary HIP Analogs.

| Peptide ID/SEQ ID NO | Sequence |
| --- | --- |
| 57 | H-IGLHDPTQGTEPAGS-OH |
| 58 | H-IGLHDPTQGTLPNGE-OH |
| 59 | H-IGLHDPTQGTLPAGE-OH |
| 60 | Ac-IGLHDPTQGTEPAG-NH2 |
| 61 | Ac-IGLHDPTQGTEPNGE-NH2 |
| 62 | Ac-IGLHDPTQGTEPAGE-NH2 |
| 63 | H-IGLHDPTQGTEPNGE-NH2 |
| 64 | H-IGLHDPTQGTEPNGC-OH |
| 65 | Ac-IGLHDPTQGTEPNGC-OH |
| 66 | H-IGLHDPTQGTEPNGC-NH2 |
| 67 | Ac-IGLHDPTQGTEPNGC-NH2 |
| 68 | H-IGLHDPTQGTEPAGE-NH2 |
| 69 | H-IGLHDPTQGTEPAGC-OH |
| 70 | Ac-IGLHDPTQGTEPAGC-OH |
| 71 | H-IGLHDPTQGTEPAGC-NH2 |
| 72 | Ac-IGLHDPTQGTEPAGC-NH2 |

The invention provides peptides or analogs thereof that are analogs of INGAP-PP. In one embodiment, the invention provides a peptide or analog thereof comprising a sequence selected from the group consisting of IGLHDPSHGTLPAGS (SEQ ID NO:7); and IGLHDPSHGTLPAG (SEQ ID NO:73). For example, the peptide or analog can comprise a peptide or analog selected from: IGLHDPSHGTLPAGS (SEQ ID NO:7); IGLHDPSHGTLPAG (SEQ ID NO:73); IGLHDPSHGTLPAGSK (SEQ ID NO:9); IGLHDPSHGTLP(Aib)GS (SEQ ID NO:10); IGLHDPSHGTLP(N-methyl-L-Ala)GS (SEQ ID NO:11); Ac-IGLHDPSHGTLPAGS (SEQ ID NO:12); (D-Ile)GLHDPSHGTLPAGS (SEQ ID NO:13); (L-NorVal)GLHDPSHGTLPAGS (SEQ ID NO:14); (L-NorLeu)GLHDPSHGTLPAGS (SEQ ID NO:15); IGLHDPSHGTLPAG-NH2 (SEQ ID NO:28); Ac-IGLHDPSHGTLPAGS-NH2 (SEQ ID NO:29); Ac-IGLHDPSHGTLPAG-NH2 (SEQ ID NO:30); IGLHDPSHGTLPAGS-NH2 (SEQ ID NO:41); IGLHDPSHGTLPAGSC (SEQ ID NO:42); Ac-IGLHDPSHGTLPAGSC (SEQ ID NO:43); IGLHDPSHGTLPAGSC-NH2 (SEQ ID NO:44); Ac-IGLHDPSHGTLPAGSC-NH2 (SEQ ID NO:45); IGLHDPSHGTLPAGC (SEQ ID NO:46); Ac-IGLHDPSHGTLPAGC (SEQ ID NO:47); IGLHDPSHGTLPAGC-NH2 (SEQ ID NO:48); and Ac-IGLHDPSHGTLPAGC-NH2 (SEQ ID NO:49).

In a particular embodiment of the invention, the peptide or analog thereof can consist of: IGLHDPSHGTLPAGS (SEQ ID NO:7); IGLHDPSHGTLPAG (SEQ ID NO:73); IGLHDPSHGTLPAGSK (SEQ ID NO:9); IGLHDPSHGTLP(Aib)GS (SEQ ID NO:10); IGLHDPSHGTLP(N-methyl-L-Ala)GS (SEQ ID NO:11); Ac-IGLHDPSHGTLPAGS (SEQ ID NO:12); (D-Ile)GLHDPSHGTLPAGS (SEQ ID NO:13); (L-NorVal)GLHDPSHGTLPAGS (SEQ ID NO:14); (L-NorLeu)GLHDPSHGTLPAGS (SEQ ID NO:15); IGLHDPSHGTLPAG-NH2 (SEQ ID NO:28); Ac-IGLHDPSHGTLPAGS-NH2 (SEQ ID NO:29); Ac-IGLHDPSHGTLPAG-NH2 (SEQ ID NO:30); IGLHDPSHGTLPAGS (SEQ ID NO:41); IGLHDPSHGTLPAGSC (SEQ ID NO:42); Ac-IGLHDPSHGTLPAGSC (SEQ ID NO:43); IGLHDPSHGTLPAGSC-NH2 (SEQ ID NO:44); Ac-IGLHDPSHGTLPAGSC-NH2 (SEQ ID NO:45); IGLHDPSHGTLPAGC (SEQ ID NO:46); Ac-IGLHDPSHGTLPAGC (SEQ ID NO:47); IGLHDPSHGTLPAGC-NH2 (SEQ ID NO:48); or Ac-IGLHDPSHGTLPAGC-NH2 (SEQ ID NO:49).

In another embodiment of the invention, additional INGAP-PP analogs are provided. An embodiment of the invention provided herein includes a peptide or analog thereof comprising a peptide or analog selected from the group consisting of: Ac-IGLHDPSHGTLPNGS (SEQ ID NO:16); (D-Ile)GLHDPSHGTLPNGS (SEQ ID NO:17); Ac-IGLHD PSHGT LPNGS-NH2 (SEQ ID NO:31); IGLHDPSHGTLPNGS-NH2 (SEQ ID NO:32); IGLHDPSHGTLPNGSC (SEQ ID NO:33); Ac-IGLHDPSHGTLPNGSC (SEQ ID NO:34); IGLHDPSHGTLPNGSC-NH2 (SEQ ID NO:35); Ac-IGLHDPSHGTLPNGSC-NH2 (SEQ ID NO:36); IGLHDPSHGTLPNGC (SEQ ID NO:37); Ac-IGLHDPSHGTLPNGC (SEQ ID NO:38); IGLHDPSHGTLPNGC-NH2 (SEQ ID NO:39); Ac-IGLHDPSHGTLPNGC-NH2 (SEQ ID NO:40); IGLHDPSHGTLPNG (SEQ ID NO:74); Ac-IGLHDPSHGTLPNG (SEQ ID NO:75); IGLHDPSHGTLPNG-NH2 (SEQ ID NO:76); Ac-IGLHDPSHGTLPNG-NH2 (SEQ ID NO:77); H-IGLHDPSHGTLPQGS-OH (SEQ ID NO:78); H-IGLHDPSHGTLPDGS-OH (SEQ ID NO:79); H-IGLHDPSHGTLPEGS-OH (SEQ ID NO:80); H-IGLHEPSHGTLPNGS-OH (SEQ ID NO:81); H-IGLHQPSHGTLPNGS-OH (SEQ ID NO:82); H-IGLHNPSHGTLPNGS-OH (SEQ ID NO:83); H-IGLHEPSHGTLPAGS-OH (SEQ ID NO:84); H-IGLHQPSHGTLPAGS-OH (SEQ ID NO:85); H-IGLHNPSHGTLPAGS-OH (SEQ ID NO:86); H-IGLHDPSHGTLPQGSC-OH (SEQ ID NO:87); H-IGLHDPSHGTLPDGSC-OH (SEQ ID NO:88); H-IGLHDPSHGTLPEGSC-OH (SEQ ID NO:89); H-IGLHEPSHGTLPNGSC-OH (SEQ ID NO:90); H-IGLHQPSHGTLPNGSC-OH (SEQ ID NO:91); H-IGLHNPSHGTLPNGSC-OH (SEQ ID NO:92); H-IGLHDPSHGTLPQG-OH (SEQ ID NO:93); H-IGLHDPSHGTLPDG-OH (SEQ ID NO:94); H-IGLHDPSHGTLPEG-OH (SEQ ID NO:95); H-IGLHEPSHGTLPNG-OH (SEQ ID NO:96); H-IGLHQPSHGTLPNG-OH (SEQ ID NO:97); H-IGLHNPSHGTLPNG-OH (SEQ ID NO:98); H-IGLHEPSHGTLPAG-OH (SEQ ID NO:99); H-IGLHQPSHGTLPAG-OH (SEQ ID NO:100); H-IGLHNPSHGTLPAG-OH (SEQ ID NO:101); H-IGLHDPSHGTLPQGE-OH (SEQ ID NO:102); H-IGLHDPSHGTLPDGE-OH (SEQ ID NO:103); H-IGLHDPSHGTLPEGE-OH (SEQ ID NO:104); H-IGLHEPSHGTLPNGE-OH (SEQ ID NO:105); H-IGLHQPSHGTLPNGE-OH (SEQ ID NO:106); H-IGLHNPSHGTLPNGE-OH (SEQ ID NO:107); H-IGLHEPSHGTLPAGE-OH (SEQ ID NO:108); H-IGLHQPSHGTLPAGE-OH (SEQ ID NO:109); or H-IGLHNPSHGTLPAGE-OH (SEQ ID NO:110).

In a particular embodiment of the invention, the peptide or analog thereof consists of: Ac-IGLHDPSHGTLPNGS (SEQ ID NO:16); (D-Ile)GLHDPSHGTLPNGS (SEQ ID NO:17); Ac-IGLHD PSHGT LPNGS-NH2 (SEQ ID NO:31); IGLHDPSHGTLPNGS-NH2 (SEQ ID NO:32); IGLHDPSHGTLPNGSC (SEQ ID NO:33); Ac-IGLHDPSHGTLPNGSC (SEQ ID NO:34); IGLHDPSHGTLPNGSC-NH2 (SEQ ID NO:35); Ac-IGLHDPSHGTLPNGSC-NH2 (SEQ ID NO:36); IGLHDPSHGTLPNGC (SEQ ID NO:37); Ac-IGLHDPSHGTLPNGC (SEQ ID NO:38); IGLHDPSHGTLPNGC-NH2 (SEQ ID NO:39); Ac-IGLHDPSHGTLPNGC-NH2 (SEQ ID NO:40); IGLHDPSHGTLPNG (SEQ ID NO:74); Ac-IGLHDPSHGTLPNG (SEQ ID NO:75); IGLHDPSHGTLPNG-NH2 (SEQ ID NO:76); Ac-IGLHDPSHGTLPNG-NH2 (SEQ ID NO:77); H-IGLHDPSHGTLPQGS-OH (SEQ ID NO:78); H-IGLHDPSHGTLPDGS-OH (SEQ ID NO:79); H-IGLHDPSHGTLPEGS-OH (SEQ ID NO:80); H-IGLHEPSHGTLPNGS-OH (SEQ ID NO:81); H-IGLHQPSHGTLPNGS-OH (SEQ ID NO:82); H-IGLHNPSHGTLPNGS-OH (SEQ ID NO:83); H-IGLHEPSHGTLPAGS-OH (SEQ ID NO:84); H-IGLHQPSHGTLPAGS-OH (SEQ ID NO:85); H-IGLHNPSHGTLPAGS-OH (SEQ ID NO:86); H-IGLHDPSHGTLPQGSC-OH (SEQ ID NO:87); H-IGLHDPSHGTLPDGSC-OH (SEQ ID NO:88); H-IGLHDPSHGTLPEGSC-OH (SEQ ID NO:89); H-IGLHEPSHGTLPNGSC-OH (SEQ ID NO:90); H-IGLHQPSHGTLPNGSC-OH (SEQ ID NO:91); H-IGLHNPSHGTLPNGSC-OH (SEQ ID NO:92); H-IGLHDPSHGTLPQG-OH (SEQ ID NO:93); H-IGLHDPSHGTLPDG-OH (SEQ ID NO:94); H-IGLHDPSHGTLPEG-OH (SEQ ID NO:95); H-IGLHEPSHGTLPNG-OH (SEQ ID NO:96); H-IGLHQPSHGTLPNG-OH (SEQ ID NO:97); H-IGLHNPSHGTLPNG-OH (SEQ ID NO:98); H-IGLHEPSHGTLPAG-OH (SEQ ID NO:99); H-IGLHQPSHGTLPAG-OH (SEQ ID NO:100); H-IGLHNPSHGTLPAG-OH (SEQ ID NO:101); H-IGLHDPSHGTLPQGE-OH (SEQ ID NO:102); H-IGLHDPSHGTLPDGE-OH (SEQ ID NO:103); H-IGLHDPSHGTLPEGE-OH (SEQ ID NO:104); H-IGLHEPSHGTLPNGE-OH (SEQ ID NO:105); H-IGLHQPSHGTLPNGE-OH (SEQ ID NO:106); H-IGLHNPSHGTLPNGE-OH (SEQ ID NO:107); H-IGLHEPSHGTLPAGE-OH (SEQ ID NO:108); H-IGLHQPSHGTLPAGE-OH (SEQ ID NO:109); or H-IGLHNPSHGTLPAGE-OH (SEQ ID NO:110).

Further INGAP-PP peptide analogs are provided herein. In still another embodiment, the invention provides a peptide or analog thereof comprising a sequence selected from the group consisting of: IGLHAPSHGTLPNGS (SEQ ID NO:6); IGLHAPSHGTLPAGS (SEQ ID NO:8); IGLHDPSHGTEPNGS (SEQ ID NO:18); IGLHDPSQGTLPNGS (SEQ ID NO:19); IGLHDPTHGTLPNGS (SEQ ID NO:20); IGLHDPSHGTLPNGE (SEQ ID NO:21); IGLHDPSHGTLPNGK (SEQ ID NO:22); IGLHDPSHGTLPAGK (SEQ ID NO:23); IGLHDPSHGTEPAGS (SEQ ID NO:24); IGLHDPSQGTLPAGS (SEQ ID NO:25); and IGLHDPTHGTLPAGS (SEQ ID NO:26); IGLHDPSHGTLPAGE (SEQ ID NO:27).

For example, the invention provides a peptide or analog thereof comprising a peptide or analog selected from: IGLHAPSHGTLPNGS (SEQ ID NO:6); IGLHAPSHGTLPAGS (SEQ ID NO:8); IGLHDPSHGTEPNGS (SEQ ID NO:18); IGLHDPSQGTLPNGS (SEQ ID NO:19); IGLHDPTHGTLPNGS (SEQ ID NO:20); IGLHDPSHGTLPNGE (SEQ ID NO:21); IGLHDPSHGTLPNGK (SEQ ID NO:22); IGLHDPSHGTLPAGK (SEQ ID NO:23); IGLHDPSHGTEPAGS (SEQ ID NO:24); IGLHDPSQGTLPAGS (SEQ ID NO:25); IGLHDPTHGTLPAGS (SEQ ID NO:26); and IGLHDPSHGTLPAGE (SEQ ID NO:27). In another embodiment, the invention provides a peptide or analog thereof consisting of: IGLHAPSHGTLPNGS (SEQ ID NO:6); IGLHAPSHGTLPAGS (SEQ ID NO:8); IGLHDPSHGTEPNGS (SEQ ID NO:18); IGLHDPSQGTLPNGS (SEQ ID NO:19); IGLHDPTHGTLPNGS (SEQ ID NO:20); IGLHDPSHGTLPNGE (SEQ ID NO:21); IGLHDPSH- GTLPNGK (SEQ ID NO:22); IGLHDPSHGTLPAGK (SEQ ID NO:23); IGLHDPSHGTEPAGS (SEQ ID NO:24); IGLHDPSQGTLPAGS (SEQ ID NO:25); IGLHDPTHGTLPAGS (SEQ ID NO:26); or IGLHDPSHGTLPAGE (SEQ ID NO:27).

The invention additionally provides HIP analogs. In an embodiment of the invention, the invention provides a peptide or analog thereof comprising the sequence IGLHDPTQGTEPAGE (SEQ ID NO:50). In an embodiment of the invention, the peptide or analog can comprise a peptide or analog selected from: IGLHDPTQGTEPAGE (SEQ ID NO:50); IGLHDPTQGTEP(Aib)GE (SEQ ID NO:51); Ac-IGLHDPTQGTEPAGE (SEQ ID NO:52); (D-Ile)GLHDPTQGTEPAGE (SEQ ID NO:53); Ac-IGLHDPTQGTEPAG-NH2 (SEQ ID NO:60); Ac-IGLHD PTQGT EPAGE-NH2 (SEQ ID NO:62); IGLHDPTQGTEPAGE-NH2 (SEQ ID NO:68); IGLHDPTQGTEPAGC (SEQ ID NO:69); Ac-IGLHDPTQGTEPAGC (SEQ ID NO:70); IGLHDPTQGTEPAGC-NH2 (SEQ ID NO:71); and Ac-IGLHDPTQGTEPAGC-NH2 (SEQ ID NO:72). In a particular embodiment, the peptide or analog thereof consists of: IGLHDPTQGTEPAGE (SEQ ID NO:50); IGLHDPTQGTEP(Aib)GE (SEQ ID NO:51); Ac-IGLHDPTQGTEPAGE (SEQ ID NO:52); (D-Ile)GLHDPTQGTEPAGE (SEQ ID NO:53); and Ac-IGLHDPTQGTEPAG-NH2 (SEQ ID NO:60); Ac-IGLHD PTQGT EPAGE-NH2 (SEQ ID NO:62); IGLHDPTQGTEPAGE-NH2 (SEQ ID NO:68); IGLHDPTQGTEPAGC (SEQ ID NO:69); Ac-IGLHD PTQGT EPAGC (SEQ ID NO:70); IGLHD PTQGT EPAGC-NH2 (SEQ ID NO:71); or Ac-IGLHD PTQGT EPAGC-NH2 (SEQ ID NO:72).

In another embodiment, the invention provides additional HIP peptide analogs. For example, the invention provides a peptide or analog thereof comprising a peptide or analog selected from the group consisting of: Ac-IGLHDPTQGTEPNGE (SEQ ID NO:54); (D-Ile)GLHDPTQGTEPNGE (SEQ ID NO:55); Ac-IGLHDPTQGTEPNGE-NH2 (SEQ ID NO:61); IGLHDPTQGTEPNGE-NH2 (SEQ ID NO:63); IGLHDPTQGTEPNGC (SEQ ID NO:64); Ac-IGLHDPTQGTEPNGC (SEQ ID NO:65); IGLHDPTQGTEPNGC-NH2 (SEQ ID NO:66); and Ac-IGLHDPTQGTEPNGC-NH2 (SEQ ID NO:67). In a particular embodiment, the peptide or analog thereof can consist of: Ac-IGLHDPTQGTEPNGE (SEQ ID NO:54); (D-Ile)GLHDPTQGTEPNGE (SEQ ID NO:55); Ac-IGLHDPTQGTEPNGE-NH2 (SEQ ID NO:61); IGLHDPTQGTEPNGE-NH2 (SEQ ID NO:63); IGLHDPTQGTEPNGC (SEQ ID NO:64); Ac-IGLHDPTQGTEPNGC (SEQ ID NO:65); IGLHDPTQGTEPNGC-NH2 (SEQ ID NO:66); or Ac-IGLHDPTQGTEPNGC-NH2 (SEQ ID NO:67).

In another embodiment of the invention, a peptide or analog thereof can comprise a sequence selected from the group consisting of: IGLHDPTQGTEPNGS (SEQ ID NO:56); IGLHDPTQGTEPAGS (SEQ ID NO:57); IGLHDPTQGTLPNGE (SEQ ID NO:58); and IGLHDPTQGTLPAGE (SEQ ID NO:59). For example, the peptide or analog thereof can comprise a peptide or analog selected from: IGLHDPTQGTEPNGS (SEQ ID NO:56); IGLHDPTQGTEPAGS (SEQ ID NO:57); IGLHDPTQGTLPNGE (SEQ ID NO:58); and IGLHDPTQGTLPAGE (SEQ ID NO:59). In a particular embodiment, peptide or analog thereof can consist of: IGLHDPTQGTEPNGS (SEQ ID NO:56); IGLHDPTQGTEPAGS (SEQ ID NO:57); IGLHDPTQGTLPNGE (SEQ ID NO:58); or IGLHDPTQGTLPAGE (SEQ ID NO:59).

In a particular embodiment, the invention provides a peptide or analog thereof comprising Ac-IGLHDPSHGTLPAGS (SEQ ID NO:12). In another particular embodiment, the invention provides a peptide or analog thereof consisting of Ac-IGLHDPSHGTLPAGS (SEQ ID NO:12). In still a further embodiment, the invention provides a peptide or analog thereof comprising Ac-IGLHDPSHGTLPNGS-NH2 (SEQ ID NO:31). In yet another further embodiment, the invention provides a peptide or analog thereof consisting of Ac-IGLHDPSHGTLPNGS-NH2 (SEQ ID NO:31). In comparison to the parent INGAP-PP peptide, the peptides of SEQ ID NO:12 and SEQ ID NO:31 have significantly improved stability in plasma and culture medium, significantly improved pharmacokinetic properties, significantly stronger effect on glucose stimulated insulin secretion, significantly more effective induction of islet cells, and significantly stronger islet neogenesis effect. As disclosed herein, the peptides of SEQ ID NO:12 and SEQ ID NO:31 exhibited higher efficacy relative to the parent INGAP-PP peptide (see Example VIII). A shift towards small islet size was achieved with the peptides of SEQ ID NO:12 and SEQ ID NO:31 at 1/100 the dose of the parent INGAP-PP peptide (see Example IX). The peptides of SEQ ID NO:12 and SEQ ID NO:31 additionally exhibited improved pharmacokinetic properties as evidenced by a significant increase in AUC and Cmax and by an increased plasma and pancreas concentration relative to the parent INGAP-PP peptide (see Example X). The peptides of SEQ ID NO:12 and SEQ ID NO:31 also exhibited increased stability in culture medium and in rat, mouse and human plasma (see Example XI). Therefore, the peptides of SEQ ID NO:12 and SEQ ID NO:31 have significant advantages over the parent INGAP-PP peptide. The peptide or analog of this invention is useful for a variety of applications, including but not limited to, stimulating pancreatic islet cell growth, producing a population of pancreatic islet cells ex vivo or in vivo, increasing the number of pancreatic islet cells in a human, and treating diseases or conditions with impaired pancreatic function such as diabetes mellitus. More specifically, diseases or conditions with impaired pancreatic function include but are not limited to type 1 diabetes, type 2 diabetes, latent autoimmune diabetes in adults (LADA), impaired fasting glucose, impaired glucose tolerance, insulin deficiency, fasting hyperinsulinemia, insulin resistance, impaired fasting insulin levels, and partial pancreatomy due to injury or inflammation. The peptide or analog of this invention can be administered to a patient at a much lower dosage level than the parent INGAP-PP peptide, resulting in improved efficacy and/or reduced side effects over the course of treatment. In preferred embodiments, the peptide or analog of this invention is administered to a patient each time no more than 10 mg/kg, no more than 5 mg/kg, no more than 1 mg/kg, no more than 0.5 mg/kg, or no more than 0.1 mg/kg. In other preferred embodiments, the peptide or analog of this invention is administered to a patient in a dose range of 0.1-100 mg per day, 1-50 mg per day, 5-100 mg per day, 5-50 mg per day, 0.1-10 mg per day, or 0.1-1 mg per day.

In another embodiment, the invention provides a peptide or analog having the following formula: $X^1GLHX^2PX^3X^4GTX^5PX^6GS$ (SEQ ID NO: 111), wherein $X^1$ is selected from Isoleucine(I), D-Isoleucine, L-NorValine, or L-NorLeucine; $X^2$ is selected from Alanine(A), or Aspartic Acid(D); $X^3$ is selected from Serine(S), or Threonine(T); $X^4$ is selected from Histidine(H), or Glutamine(Q);

$X^5$ is selected from Leucine(L), or Glutamic acid(E); and when $X^1$ is Isoleucine(I), $X^2$ is Aspartic Acid(D), $X^3$ is Serine(S), $X^4$ is Histidine(H), and $X^5$ is Leucine(L), $X^6$ is selected from Alanine(A), α-Amino-isobutyric acid, or N-methyl-L-Alanine; otherwise, $X^6$ is selected from Alanine (A), Asparagine(N), α-Amino-isobutyric acid, or N-methyl-L-Alanine. In a particular embodiment, the peptide or analog of the formula can be selected from H-IGLHAPSH-GTLPNGS-OH(SEQ ID NO: 6), H-IGLHDPSHGTLP(Aib)GS-OH (SEQ ID NO: 10), H-IGLHDPSHGTLP(N-methyl-L-Alanine)GS-OH (SEQ ID NO: 11), H-(D-Isoleucine)GLHDPSHGTLPNGS-OH (SEQ ID NO: 17), H-IGLHDPSHGTEPNGS-OH (SEQ ID NO: 18), H-IGLH-DPSQGTLPNGS-OH (SEQ ID NO: 19), and H-IGLH-DPTHGTLPNGS-OH (SEQ ID NO: 20). In another particular embodiment, the peptide or analog of the formula can be selected from H-IGLHDPSHGTLPAGS-OH (SEQ ID NO: 7), H-IGLHAPSHGTLPAGS-OH (SEQ ID NO: 8), H-(D-Isoleucine)GLHDPSHGTLPAGS-OH (SEQ ID NO: 13), H-(L-NorValine)GLHDPSHGTLPAGS-OH (SEQ ID NO: 14), H-(L-NorLeucine)GLHDPSHGTLPAGS-OH (SEQ ID NO: 15), H-IGLHDPSHGTEPAGS-OH (SEQ ID NO: 24), H-IGLHDPSQGTLPAGS-OH (SEQ ID NO: 25), and H-IG-LHDPTHGTLPAGS-OH (SEQ ID NO: 26).

In yet another embodiment, the invention provides a peptide or analog having the following formula: $R^1$-IGLH-DPSHGTLPNGX$^1$(C)$_m$—$R^2$ (SEQ ID NO: 112), wherein, m is 0 or 1; $R^1$ is selected from —H or —Ac; $R^2$ is selected from —OH or —NH$_2$; and when $R^1$ is —H, $R^2$ is —OH, and m is 0, $X^1$ is selected from Glutamic acid(E), Cysteine(C), or Lysine(K); otherwise, $X^1$ is selected from Serine(S), Glutamic acid(E), Cysteine(C), or Lysine(K). In particular embodiment, the peptide or analog of the formula can be selected from H-IGLHDPSHGTLPNGE-OH (SEQ ID NO: 21), and H-IGLHDPSHGTLPNGK-OH (SEQ ID NO: 22). In another particular embodiment, the peptide or analog of the formula can be selected from Ac-IGLHDPSH-GTLPNGS-NH$_2$ (SEQ ID NO: 31), H-IGLHDPSH-GTLPNGS-NH$_2$ (SEQ ID NO: 32), and Ac-IGLHDPSH-GTLPNGS-OH (SEQ ID NO: 16). In still another particular embodiment, the peptide or analog of the formula can be selected from H-IGLHDPSHGTLPNGC-OH (SEQ ID NO: 37), Ac-IGLHDPSHGTLPNGC-OH (SEQ ID NO: 38), H-IGLHDPSHGTLPNGC-NH$_2$ (SEQ ID NO: 39), and Ac-IGLHDPSHGTLPNGC-NH$_2$ (SEQ ID NO: 40). In still a further particular embodiment, the peptide or analog of the formula can be selected from H-IGLHDPSHGTLPNGSC-OH (SEQ ID NO: 33), Ac-IGLHDPSHGTLPNGSC-OH (SEQ ID NO: 34), H-IGLHDPSHGTLPNGSC-NH$_2$ (SEQ ID NO: 35), and Ac-IGLHDPSHGTLPNGSC-NH$_2$ (SEQ ID NO: 36). In yet another particular embodiment, the peptide or analog of the formula can be selected from H-IGLHDP-SHGTLPNG-OH (SEQ ID NO: 74), Ac-IGLHDPSH-GTLPNG-OH (SEQ ID NO: 75), H-IGLHDPSHGTLPNG-NH$_2$ (SEQ ID NO: 76), and Ac-IGLHDPSHGTLPNG-NH$_2$ (SEQ ID NO: 77).

In yet another embodiment, the invention provides a peptide or analog having the following formula: $R^1$-IGLH-DPSHGTLPAG(X$^1$)$_m$—$R^2$ (SEQ ID NO: 113); wherein, m is 0 or 1; $R^1$ is selected from —H or —Ac; $R^2$ is selected from —OH or —NH$_2$; when $R^1$ is —H, $R^2$ is —OH, and m is 1, $X^1$ is selected from Glutamic acid(E), Cysteine(C), or Lysine(K); otherwise, $X^1$ is selected from Serine(S), Glutamic acid(E), Cysteine(C), or Lysine(K). In a particular embodiment, the peptide or analog of the formula can be selected from H-IGLHDPSHGTLPAGE-OH (SEQ ID NO: 27), and H-IGLHDPSHGTLPAGK-OH (SEQ ID NO: 23). In another particular embodiment, the peptide or analog of the formula can be selected from Ac-IGLHDPSHGTL-PAGS-NH$_2$ (SEQ ID NO: 29), H-IGLHDPSHGTLPAGS-NH$_2$ (SEQ ID NO: 41), and Ac-IGLHDPSHGTLPAGS-OH (SEQ ID NO: 12). In still another particular embodiment, the peptide or analog of the formula can be selected from H-IGLHDPSHGTLPAGC-OH (SEQ ID NO: 46), Ac-IGL-HDPSHGTLPAGC-OH (SEQ ID NO: 47), H-IGLHDPSH-GTLPAGC-NH$_2$ (SEQ ID NO: 48), and Ac-IGLHDPSH-GTLPAGC-NH$_2$ (SEQ ID NO: 49). In yet another particular embodiment, the peptide or analog of the formula can be selected from H-IGLHDPSHGTLPAG-OH (SEQ ID NO: 73), H-IGLHDPSHGTLPAG-NH$_2$ (SEQ ID NO: 28), and Ac-IGLHDPSHGTLPAG-NH$_2$ (SEQ ID NO: 30).

In another embodiment, the invention provides a peptide or analog having the following formula: $R^1$-IGLHDPSH-GTLPAGSX$^2$-$R^2$ (SEQ ID NO: 114), wherein, $X^2$ is selected from Lysine(K) or Cysteine(C), $R^1$ is selected from —H or —Ac, $R^2$ is selected from —OH or —NH$_2$. In a particular embodiment, the peptide or analog of the formula can be selected from H-IGLHDPSHGTLPAGSK-OH (SEQ ID NO: 9), H-IGLHDPSHGTLPAGSC-OH (SEQ ID NO: 42), Ac-IGLHDPSHGTLPAGSC-OH (SEQ ID NO: 43), H-IG-LHDPSHGTLPAGSC-NH$_2$ (SEQ ID NO: 44), and Ac-IGLHDPSHGTLPAGSC-NH$_2$ (SEQ ID NO: 45).

In another embodiment, the invention provides a peptide or analog having the following formula: $X^1$GLHDPTQGTX$^2$PX$^3$GE (SEQ ID NO: 115), $X^1$ is selected from Isoleucine(I) or D-Isoleucine; $X^2$ is selected from Glutamic acid(E) or Leucine(L); and when $X^1$ is Isoleucine(I) and $X^2$ is Glutamic acid(E), $X^3$ is selected from Alanine(A), or α-Amino-isobutyric acid; otherwise, $X^3$ is selected from Alanine(A), Asparagine(N), or α-Amino-isobutyric acid. In a particular embodiment, the peptide or analog of the formula can be selected from H-IGLH-DPTQGTEP(Aib)GE-OH (SEQ ID NO: 51), H-(D-Isoleucine)GLHDPTQGTEPNGE-OH (SEQ ID NO: 55), and H-IGLHDPTQGTLPNGE-OH (SEQ ID NO: 58). In another particular embodiment, the peptide or analog of the formula can be selected from H-IGLHDPTQGTEPAGE-OH (SEQ ID NO: 50), H-(D-Isoleucine)GLHDPTQGTEPAGE-OH (SEQ ID NO: 53), and H-IGLHDPTQGTLPAGE-OH (SEQ ID NO: 59).

In another embodiment, the invention provides a peptide or analog having the following formula: $R^1$-IGLH-DPTQGTEPNGX$^1$-$R^2$ (SEQ ID NO: 116), wherein, $R^1$ is selected from —H or —Ac; $R^2$ is selected from —OH or —NH$_2$; when $R^1$ is —H and $R^2$ is —OH, $X^1$ is selected from Serine(S), or Cysteine(C); otherwise, $X^1$ is selected from Serine(S), Glutamic acid(E), or Cysteine(C). In a particular embodiment, the peptide or analog of the formula can be selected from Ac-IGLHDPTQGTEPNGE-OH (SEQ ID NO: 54), Ac-IGLHDPTQGTEPNGE-NH$_2$(SEQ ID NO: 61), and H-IGLHDPTQGTEPNGE-NH$_2$ (SEQ ID NO: 63). In another particular embodiment, the peptide or analog of the formula can be selected from H-IGLHDPTQGTEPNGS-OH (SEQ ID NO: 56), H-IGLHDPTQGTEPNGC-OH (SEQ ID NO: 64), Ac-IGLHDPTQGTEPNGC-OH(SEQ ID NO: 65), H-IGLHDPTQGTEPNGC-NH$_2$ (SEQ ID NO: 66), and Ac-IGLHDPTQGTEPNGC-NH$_2$ (SEQ ID NO: 67).

In another embodiment, the invention provides a peptide or analog having the following formula: $R^1$-IGLH-DPTQGTEPAG(X$^1$)$_n$—$R^2$ (SEQ ID NO: 117), wherein, $R^1$ is selected from —H or —Ac; $R^2$ is selected from —OH or —NH$_2$; n is 0, or 1; $X^1$ is selected from Serine(S), or Cysteine(C). In a particular embodiment, the peptide or analog of the formula can be selected from H-IGLH- DPTQGTEPAGS-OH (SEQ ID NO: 57), Ac-IGLH-DPTQGTEPAG-NH₂ (SEQ ID NO: 60), H-IGLH-DPTQGTEPAGC-OH (SEQ ID NO: 69), Ac-IGLHDPTQGTEPAGC-OH (SEQ ID NO: 70), H-IGLH-DPTQGTEPAGC-NH₂ (SEQ ID NO: 71), and Ac-IGLH-DPTQGTEPAGC-NH₂ (SEQ ID NO: 72). In another particular embodiment, the peptide or analog of the formula can be selected from Ac-IGLHDPTQGTEPAGE-OH (SEQ ID NO: 52), Ac-IGLHDPTQGTEPAGE-NH₂ (SEQ ID NO: 62), and H-IGLHDPTQGTEPAGE-NH₂ (SEQ ID NO: 68).

As described herein, the peptides or analogs of the invention include analogs of INGAP-PP and HIP that can be peptides having the standard 20 naturally occurring amino acids, as well as other naturally and/or non-naturally occurring amino acids. The peptides as described herein generally use conventional nomenclature. For example, some peptides are designated H-XXX-OH, and it is understood by those skilled in the art that these can designate unmodified amino- (H—) or carboxy- (—OH) termini. The amino acid sequence can also be represented without an indication of a modification on the amino- or carboxy-terminus. It is understood by those skilled in the art that peptides described herein, unless a specific modification is indicated on the N- or C-terminus, can include unmodified and modified amino- and/or carboxy-termini on a peptide comprising a specified amino acid sequence or peptide analog. Thus, a peptide or analog comprising a designated amino acid sequence can include additional amino acids on the N- and/or C-terminus as well as modified amino acids of the designated sequence. A peptide or analog comprising a designated peptide or analog similarly can include modified amino acids and/or additional amino acids, unless the N- and/or C-terminus comprises a modification that precludes the addition of an amino acid, for example through a peptide bond. Such modifications can include, for example, an acetylated N-terminus and/or amidated C-terminus.

As described herein, the peptides or analogs of the invention can comprise a modification. It is understood by those skilled in the art that a number of modifications can be made to a peptide or analog. Exemplary modifications include, but are not limited to, an acetylated N-terminus, an amidated C-terminus, a D amino acid, a modified amino acid, a fatty acid modification, esterification, or a combination thereof. Any of a number of well known modifications of a peptide or amino acid can be included in a peptide or analog of the invention. For example, derivatives can include chemical modifications of the polypeptide such as esterification, alkylation, acylation, carbamylation, iodination, or any modification which derivatizes the polypeptide. Modifications of a peptide or analog can include modified amino acids, for example, hydroxyproline or carboxyglutamate, and can include amino acids that are not linked by peptide bonds.

It is understood by those skilled in the art that any of a number of well known methods can be employed to produce peptides or analogs of the invention (see, for example, *Protein Engineering: A practical approach* (IRL Press 1992); Bodanszky, *Principles of Peptide Synthesis* (Springer-Verlag 1984), Lloyd-Williams et al., *Tetrahedron* 49:11065-11133 (1993); Kent, *Ann. Rev. Biochem.* 57:957-989 (1988); Merrifield, *J. Am. Chem. Soc.,* 85:2149-2154 (1963); Merrifield, *Methods Enzymol.* 289:3-13 (1997)). A particularly useful method to produce peptides or analogs of the invention is via chemical synthesis using well known methods of peptide synthesis. Chemical synthesis is particularly useful for introducing non-naturally occurring amino acids, modified amino acids and/or a modified N- and/or C-terminus. For example, an advantage of using chemical synthesis to prepare a peptide or analog of the invention is that (D)-amino acids can be substituted for (L)-amino acids, if desired. The incorporation of one or more (D)-amino acids can confer, for example, additional stability of the peptide in vitro or, particularly, in vivo, since endogenous endoproteases generally are ineffective against peptides containing (D)-amino acids. Peptides having D amino acids can also be designated herein using the well known nomenclature of a small letter for the corresponding single letter code for an amino acid.

If desired, the reactive side group of one or more amino acids in a peptide or analog of the invention can be modified or amino acid derivatives can be incorporated into the peptide. Selective modification of a reactive group of a peptide or analog can impart desirable characteristics upon a peptide or analog. The choice of including such a modification is determined, in part, by the characteristics required of the peptide. For example, a peptide or analog can have a free carboxyl terminus or can be modified so that the C-terminus is amidated (see Tables 2 and 3). Similarly, a peptide or analog can have a free amino terminus or can be modified so that the N-terminus is acetylated (Tables 2 and 3). In addition, the peptides or analogs of the invention can optionally be amidated on the C-terminus and acetylated on the N-terminus. Other modifications of the N- and/or C-terminus of a peptide or analog can also be included within the meaning of a modification.

Other modifications of a peptide or analog of the invention can include, but are not limited to, 2-Aminoadipic acid (Aad); 3-Aminoadipic acid (bAad); beta-Alanine, beta-Aminopropionic acid (bAla); 2-Aminobutyric acid (Abu); 4-Aminobutyric acid, piperidinic acid (4Abu); 6-Aminocaproic acid (Acp); 2-Aminoheptanoic acid (Ahe); 2-Aminoisobutyric acid (Aib); 3-Aminoisobutyric acid (bAib); 2-Aminopimelic acid (Apm); 2,4 Diaminobutyric acid (Dbu); Desmosine (Des); 2,2'-Diaminopimelic acid (Dpm); 2,3-Diaminopropionic acid (Dpr); N-Ethylglycine (EtGly); N-Ethylasparagine (EtAsn); Hydroxylysine (Hyl); allo-Hydroxylysine (aHyl); 3-Hydroxyproline (3Hyp); 4-Hydroxyproline (4Hyp); Isodesmosine (Ide); allo-Isoleucine (aIle); N-Methylglycine (MeGly; sarcosine); N-Methylisoleucine (MeIle); 6-N-Methyllysine (MeLys); N-Methylvaline (Me-Val); Norvaline (Nva); Norleucine (Nle); and Ornithine (Orn). It is understood that all modified alpha-amino acids can be substituted with the corresponding beta-, gamma- or omega-amino acids.

Another modification of a peptide or analog of the invention includes fatty acid modification. Thus, a peptide or analog of the invention can be modified by acylation with aliphatic groups, including C2, C4, C6, C8, C10, C12, C14, C16, C18, C20 or longer chains. The peptide or analog can also be modified by isoprenylation and/or phosphatidylinositol (PI). Additional modications of a peptide or analog of the invention includes esterification. For example, a carboxyl group can be modified by acid catalyzed esterification or condensation with an alcohol. Conversely, an alcohol group can be modified by condensation with a carboxylic acid or other acid. Additional modifications of a peptide or analog of the invention can include cyclization. For example, by introduction of conformational restraint through head-to-tail cyclization improves the peptide stability than their linear counterparts, therefore prolongs the duration of peptide action. By restricting conformational flexibility, cyclic peptide is thought to adopt a conformation which more closely mimics that of active sequence as presented in the native protein (see, for example, Dutta *Chem. Br.* 25:159(1989); Kopple, *J. Am. Chem. Soc.* 94-973-

981 (1972); Brugghe et al., *Int. J. Peptide Protein Res.* 43:166-170 (1994)). These and other amino acid, peptide or protein modifications are well known to those skilled in the art (see, for example, Glazer et al., *Chemical modification of proteins: Selected methods and analytical procedures*, Elsevier Biomedical Press, Amsterdam (1975)). It is understood that such modications can be included in a peptide or analog of the invention as single modifications or combinations of one or more modifications in a peptide or analog molecule.

The invention also includes mimetics of the peptides or analogs disclosed herein, also referred to as peptidomimetics. Mimetics encompass chemicals containing chemical moieties that mimic the function of the peptide. For example, if a peptide contains two charged chemical moieties having functional activity, a mimetic places two charged chemical moieties in a spatial orientation and constrained structure so that the charged chemical function is maintained in three-dimensional space. Thus, a mimetic orients functional groups of a peptide or analog of the invention such that the functional activity of a peptide or analog is retained.

Mimetics or peptidomimetics can include chemically modified peptides, peptide-like molecules containing non-naturally occurring amino acids, peptoids and the like, and have the functional activity of the peptide or analog upon which the peptidomimetic is derived (see, for example, *Burger's Medicinal Chemistry and Drug Discovery* 5th ed., vols. 1 to 3 (ed. M. E. Wolff; Wiley Interscience 1995)). Methods for identifying a peptidomimetic are well known in the art and include, for example, the screening of databases that contain libraries of potential peptidomimetics (Allen et al., *Acta Crystallogr.* Section B, 35:2331 (1979)) or using molecular modeling (Rusinko et al., *J. Chem. Inf. Comput. Sci.* 29:251 (1989)). Mimetics or peptidomimetics can provide desirable properties such as greater stability, for example, when administered to a subject, such as during passage through the digestive tract and, therefore, can be useful for oral administration.

A variety of mimetics or peptidomimetics are known in the art including, but not limited to, peptide-like molecules which contain a constrained amino acid, a non-peptide component that mimics peptide secondary structure, or an amide bond isostere. A mimetic or peptidomimetic that contains a constrained, non-naturally occurring amino acid can include, without limitation, an α-methylated amino acid; α-,α-dialkylglycine or α-aminocycloalkane carboxylic acid; an $^N\alpha$-$^C\alpha$-cyclized amino acid; an $^N\alpha$-methylated amino acid; a β- or γ-amino cycloalkane carboxylic acid; an α,β-unsaturated amino acid; a β,β-dimethyl or β-methyl amino acid; a β-substituted-2,3-methano amino acid; an N—Cδ or $^C\alpha$-$^C\delta$ cyclized amino acid; a substituted proline or another amino acid mimetic. A mimetic or peptidomimetic which mimics peptide secondary structure can contain, without limitation, a nonpeptidic β-turn mimic; γ-turn mimic; or mimic of helical structure, each of which is well known in the art. As non-limiting examples, a peptidomimetic also can be a peptide-like molecule which contains an amide bond isostere such as a retro-inverso modification; reduced amide bond; methylenethioether or methylene-sulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other mimetics or peptidomimetics of a peptide or analog of the invention can be used.

The invention also provides pseudopeptide derivatives of peptides or analogs of the invention. Pseudopeptides are known in the art as peptides in which a peptide bond (amide bond) in a peptide is modified to an amide bond surrogate (see, for example, Cudic and Stawikowski, *Mini-Rev Organic Chem.* 4:268-280 (2007); Anderson, in *Neuropeptide Protocols*, Brent and Carvell, eds. 73:49-60 (1996)). Exemplary amide bond surrogates include, but are not limited to, peptidosulfonamides, phosphonopeptides, depsides and depsipeptides, oliogureas, azapeptides and peptoids (see Cudic and Stawikowski, supra, 2007) as well as methylene amino, thioether and hydroxyethylene derivatives, and the like (Anderson, supra, 1996).

The peptides or analogs of the invention can be produced using methods well known to those skilled in the art, including chemical synthesis of the peptides or analogs using well known methods of peptide synthesis, as described herein. Thus, when the peptides or analogs include one or more non-standard amino acids, it is more likely that they will be produced by a chemical synthetic method. In addition to using chemical synthesis of peptides or analogs, the peptides or analogs can be produced by expression from encoding nucleic acids. This is particularly useful for peptides or analogs that include only naturally occurring amino acids. In such a case, a nucleic acid encoding the peptide sequence can be prepared using well known methods (see Sambrook et al., *Molecular Cloning: A Laboratory Manual*, Third Ed., Cold Spring Harbor Laboratory, New York (2001); Ausubel et al., *Current Protocols in Molecular Biology*, John Wiley and Sons, Baltimore, Md. (1999)). Generally such a nucleic acid will be expressed recombinantly in a suitable host organism such as a bacterium, yeast, mammalian or insect cell, and the like. Production in bacteria can be particularly useful for large scale production of a peptide or analog of the invention. The peptide can be expressed in the organism and purified using well known purification techniques.

A nucleic acid molecule encoding the peptide or analog of the invention can be cloned into an appropriate vector, particularly an expression vector, and the encoded peptide or analog can be expressed in a host cell or using an in vitro transcription/translation reaction, thereby providing a means to obtain large amounts of the peptide or analog. Optionally, the recombinant peptide can be produced as a fusion with a tag, such as a His tag, to facilitate identification and purification. Suitable vectors, host cells, in vitro transcription/translation systems, and tag sequences are well known in the art and commercially available.

The peptide or analog can be expressed as a single copy, in a polycistronic expression vector, or optionally can be expressed as a single open reading frame with multiple copies of the peptide sequence. In such a case, the peptide can be obtained by expressing an open reading frame containing multiple copies of the peptide sequence, resulting in expression of a polypeptide with multiple copies of the peptide. The polypeptide can be post-translationally processed into a peptide or analog of the invention, for example, by engineering appropriate proteolytic cleavage sites between the copies of the peptide and cleaving the polypeptide into the peptide or analog of the invention. Although such a recombinant method will generally be used when the peptide or analog of the invention is a peptide containing only naturally occurring amino acids, it is also understood that such a method can be employed with expression hosts suitably engineered to express non-naturally occurring amino acids. Additionally, it is understood that a peptide or analog expressed recombinantly can optionally be chemically modified to introduce a desired amino acid modification or N- and/or C-terminal modification using well know chemical modification methods (see Glazer et al., supra, 1975).

Thus, the invention additionally provides nucleic acids encoding peptides or analogs of the invention. Such nucleic acids include, for example, nucleic acids encoding any of the amino acid sequences of SEQ ID NOS:6-73. Thus, when the analogs include only one or more substitutions with standard amino acids, the analogs can be expressed from an expression vector using well known methods, as disclosed herein.

The peptides or analogs of the invention can comprise a sequence or peptide or analog as disclosed herein. In the case of a peptide or analog comprising an amino acid sequence or peptide, the peptide will generally have a length of 20 amino acids or less. For example, the peptide or analog can have a length of 19 amino acids or less, 18 amino acids or less, 17 amino acids or less. Thus, a peptide or analog of the invention, as disclosed herein, can have a length of 10 amino acids, 11 amino acids, 12 amino acids, 13 amino acids 14 amino acids (see Peptide 73, Peptide 74), 15 amino acids, 16 amino acids, 17 amino acids, 18 amino acids, 19 amino acids, or 20 amino acids. In the case of shorter peptides, it is understood by those skilled in the art that the shorter peptide includes a fragment of a disclosed peptide or analog, for example, by deletion of one or more amino acids on the N- and/or C-terminus of a disclosed peptide or analog, that retains functional activity, including but not limited to one or more of the biological activities of peptides and analogs of the invention, as disclosed herein. Nevertheless, it is understood that a peptide can also comprise longer amino acid lengths, so long as the functional activity of the peptide or analog is retained. Thus, a peptide or analog can have a length of less than 150 residues, less than 130 residues, less than 120 residues, less than 110 residues, less than 100 residues, less than 90 residues, less than 80 residues, less than 70 residues, less than 60 residues, less than 50 residues, less than 45 residues, less than 40 residues, less than 35 residues, less than 30 residues, less than 25 residues, less than 24 residues, less than 23 residues, less than 22 residues, less than 21 residues, less than 20 residues, less than 19 residues, less than 18 residues, or less than 17 residues. It is understood by those skilled in the art that, where a peptide or analog of the invention comprises a sequence found within a known longer sequence such as a wild type full length protein, the peptide or analog of the invention specifically excludes such a full length sequence.

The invention also provides peptides and analogs of the invention in a pharmaceutically acceptable salt form that is well known to those skilled in the art. A particularly useful salt form is acetate or hydrochloride salt form. Nevertheless, it is understood by those skilled in the art that any of a number of suitable salt forms are available. When the peptide or analog of the invention contains an acidic or basic moiety, it can be provided as a pharmaceutically acceptable salt (see, for example, Berge et al., *J. Pharm. Sci.* 1977, 66, 1-19; and *Handbook of Pharmaceutical Salts, Properties, and Use;* Stahl and Wermuth, Ed.; Wiley-VCH and VHCA: Zurich, Switzerland, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexane-sulfamic acid, deoxycholic acid, dodecylsulfuric acid, docosahexaenoic acid, eicosapntemacnioc acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, ursolic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The invention also provides peptides and analogs of the invention in a composition. For example, the peptides or analogs of Tables 2 or 3, or other peptides or analogs disclosed herein or the formulas disclosed herein, can be provided in a composition, as disclosed herein. In a particular embodiment, the composition can comprise the peptide or analog of SEQ ID NO:12 or SEQ ID NO:31. The composition can optionally be formulated with a pharmaceutically acceptable carrier to produce a pharmaceutical composition, which can be administered to the individual, which can be a human or other mammal. A pharmaceutically acceptable carrier can be, for example, water, sodium phosphate buffer, phosphate buffered saline, normal saline or Ringer's solution or other physiologically buffered saline, or other solvent or vehicle such as a glycol, glycerol, an oil such as olive oil or an injectable organic ester.

A pharmaceutically acceptable carrier can contain physiologically acceptable compounds that act, for example, to stabilize or increase the absorption of the peptide or analog of the invention. Such physiologically acceptable compounds include, for example, carbohydrates such as glucose, sucrose or dextrans; antioxidants such as ascorbic acid or glutathione; chelating agents such as ethylenediamine tetraacetic acid (EDTA), which disrupts microbial membranes; divalent metal ions such as calcium or magnesium; low molecular weight proteins; or other stabilizers or excipients. One skilled in the art would know that the choice of a pharmaceutically acceptable carrier, including a physiologically acceptable compound, depends, for example, on the route of administration of the composition. Suitable carriers and their formulations are well known in the art (see, for example, *Remington: The Science and Practice of Pharmacy,* 19th ed., ed. A. R. Gennaro, Mack Publishing Company, Easton, Pa. (1995); and *Remington's Pharmaceutical Sciences,* 18th ed., Mack Publishing Company, Easton Pa. (1990)). Typically, an appropriate amount of a pharmaceutically-acceptable salt is used in the formulation to render the formulation isotonic. The pH of the solution is generally from about 4 to about 8.5, for example, from about 4 to about 5, from about 5 to about 6, from about 6 to about 7, from about 4.5 to about 8, from about 5 to about 8, from about 5 to about 7.5, from about 5.5, to about 8, from about 5.5 to about 7.5, from about 6 to about 8, from about 6.5 to about 8, from about 7 to about 8, from about 7.5 to about 8, or from about 7 to about 7.5.

Pharmaceutical carriers are known to those skilled in the art. These most typically would be standard carriers for administration of drugs to humans, including solutions such as sterile water, saline, and buffered solutions at physiological pH, as described above. Pharmaceutical compositions can include carriers, thickeners, diluents, buffers, preservatives, surface active agents and the like in addition to the molecule of choice such as the peptides or analogs of the invention. Pharmaceutical compositions can also include one or more active ingredients such as antimicrobial agents, anti-inflammatory agents, anesthetics, and the like.

Further carriers include sustained or controlled release preparations such as semipermeable matrices of solid hydrophobic polymers covalently or non-covalently bound to the peptide or analog, which matrices are in the form of shaped articles, for example, films, liposomes, non-liposome lipid complex or microparticles, and the like, or other biocompatible polymers well known to those skilled in the art (see, for example, U.S. Pat. Nos. 6,824,822 and 8,329,648). Liposomes, which consist of phospholipids or other lipids, are nontoxic, physiologically acceptable and metabolizable carriers that are relatively simple to make and administer (Gregoriadis, *Liposome Technology*, Vol. 1 (CRC Press, Boca Raton Fla., 1984). Various drug delivery methods are well known to those skilled in the art (Langer, *Nature* 392(Suppl):5-10 (1998); Langer et al., *Nature* 428:487-492 (2004)). It will be apparent to those persons skilled in the art that certain carriers can be selected depending upon, for instance, the route of administration and concentration of composition being administered.

As disclosed herein, the peptides or analogs of the invention can be prepared as sustained or controlled release formulations. As described in Example XII, various sustained release compositions can be generated that demonstrated the feasibility of long acting release dosage forms of the peptides or analogs of the invention. Exemplary formulations include biocompatible polymers, including but not limited to polymers containing poly (ethylene glycol) (PEG), nonionic, surfactant polyols, also known as poloxamers, which are copolymers of polyoxypropylene and polyoxyethylene (poly(ethylene oxide)), polyetheramines, which can be based on ethylene oxide (EO), propylene oxide (PO), an EO/PO mix, or polytetramethylene glycol (PT-MEG), polyether diamines based on a predominantly PEG backbone, and the like. Exemplary poloxomers include, but are not limited to, Pluronic® F127, Pluronic® F38, Pluronic® F68, Pluronic® F87, Pluronic® F108, Pluronic® 10R5, Pluronic® 17R2, Pluronic® 17R4, Pluronic® 25R2, Pluronic® 25R4, Pluronic® 31R1, Pluronic® F 108 Cast Solid Surfacta, Pluronic® F 108 NF, Pluronic® F 108 Pastille, Pluronic® F 108NF Prill Poloxamer 338, Pluronic® F 127 NF, Pluronic® F 127 NF 500 BHT Prill, Pluronic® F 127 NF Prill Poloxamer 407, Pluronic® F 38 Pastille, Pluronic® F 68 LF Pastille, Pluronic® F 68 NF, Pluronic® F 68 NF Prill Poloxamer 188, Pluronic® F 68 Pastille, Pluronic® F 77, Pluronic® F 77 Micropastille, Pluronic® F 87 NF, Pluronic® F 87 NF Prill Poloxamer 237, Pluronic® F 88, Pluronic® F 88 Pastille, Pluronic® F 98, Pluronic® FT L 61, Pluronic® L 10, Pluronic® L 101, Pluronic® L 121, Pluronic® L 31, Pluronic® L 35, Pluronic® L 43, Pluronic® L 61, Pluronic® L 62, Pluronic® L 62 LF, Pluronic® L 62D, Pluronic® L 64, Pluronic® L 81, Pluronic® L 92, Pluronic® L44 NF INH surfactant Poloxamer 124, Pluronic® N 3, Pluronic® P 103, Pluronic® P 104, Pluronic® P 105, Pluronic® P 123 Surfactant, Pluronic® P 65, Pluronic® P 84, Pluronic® P 85, and the like. Exemplary polyetheramines include, but are not limited to, Jeffamine® ED-2003, Jeffamine® D-2000 Jeffamine® D-230, Jeffamine® D-400, Jeffamine® EDR-176, Jeffamine® SD-2001, Jeffamine® T-403, Jeffamine® T-5000. Additional components can include, for example, cyclodextrins such as alpha-, beta- and gamma-cyclodextrins. Methods well known in the art can be used to generate sustained release formulations. The components can be formulated at desired concentrations and ratios, including but not limited to, a concentration of 0.1% to 30%, for example, 0.5% w/w to 20%, 1%, 2%, 3%, 4%, 5%, 6%, 7%, 8%, 9%, 10%, 11%, 12%, 13%, 14%, 15%, 16%, 17%, 18%, 19%, 20%, and the like, w/w of the final weight of the composition. Other sustained release peptide delivery systems known in the art include, for example, the nanoparticle formulation comprising poly(lactic-co-glycolic acid) (PLGA), polylactide (PLA), PEG/PLGA, and liposomes, which can also be used to generate a sustained release formulation. Sustained release formulations are well known in the art (see, for example, *Remington's Pharmaceutical Sciences,* 18th ed., Mack Publishing Company, Easton Pa. (1990)). Sustained release formulations are useful for providing steady and/or continuous dosage of a peptide or analog of the invention and/or to avoid repeat administration.

The pharmaceutical composition can be administered in a number of ways depending on whether local or systemic treatment is desired, and on the area to be treated. It is understood that a variety of routes of administration are useful for the peptides, analogs and methods of the invention. Such routes encompass systemic and local administration and include, without limitation, intravenous injection, intraperitoneal injection, intramuscular injection, subcutaneous injection, transdermal delivery, transdermal diffusion or electrophoresis, inhalable administration, oral administration, local injection, intracavity, and extended release delivery devices including locally implanted extended release devices such as bioerodible or reservoir-based implants. Administration can be topically (including ophthalmically, vaginally, rectally, intranasally), orally, by inhalation, or parenterally, for example by intravenous drip, subcutaneous, intraperitoneal or intramuscular injection. Sustained release formulations can be delivered via in situ forming implants. Furthermore, it is understood that the peptides or analogs of the invention can be administered daily in a single adminstration, in multiple daily administrations, in sustained release formulations, either with continuous or intermittent, non-continuous adminstration, intermittently on non-consecutive days, and so forth so as to achieve a desired effect.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like. Insulin is a well known peptide therapeutic, so methods used for delivery of insulin are particularly amenable as a delivery method for peptides or analogs of the invention, including but not limited to syringes, pens, infusion pumps, inhalers, mouth sprays, pills, and the like.

Guidance on appropriate doses for the peptides or analogs of the invention is provided in Dungan et al., *Diabetes Metab. Res. Rev.*, 25:558-565 (2009). In particular, human clinical trials with INGAP peptide provide an indication of suitable possible doses for the peptides or analogs of the invention. Since the peptides or analogs of the invention exhibit improved efficacy over the parent INGAP peptide (see Examples), the peptides or analogs of the invention can be administered at effective doses that are lower than that used for INGAP. Exemplary doses for peptides or analogs of the invention include, but are not limited to, 0.01-1000 mg per day, for example, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990 or 1000 mg per day. In a particular embodiment, the peptide doses are about 1-100 mg per day, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 mg per day. Exemplary dose ranges include, but are not limited to, 0.01-1000, 0.1-1000, 1-1000, 10-1000, 100-1000, 0.01-500, 0.1-500, 1-500, 10-500, 100-500, 0.01-400, 0.1-400, 1-400, 10-400, 100-400, 0.01-300, 0.1-300, 1-300, 10-300, 100-300, 0.01-200, 0.1-200, 1-200, 10-200, 100-200, 0.01-100, 0.1-100, 1-100, 10-100, 1-90, 1-80, 1-70, 1-60, 1-50, 1-40, 1-30, 1-20, 1-10, 5-100, 5-90, 5-80, 5-70, 5-60, 5-50, 5-40, 5-30, 5-20, 5-10, 10-100, 10-90, 10-80, 10-70, 10-60, 10-50, 10-40, 10-30, 10-20, 15-100, 15-90, 15-80, 15-70, 15-60, 15-50, 15-40, 15-30, 15-20, 20-100, 20-90, 20-80, 20-70, 20-60, 20-50, 20-40, 20-30, 25-100, 25-90, 25-80, 25-70, 25-60, 25-50, 25-40, 25-30, 30-100, 30-90, 30-80, 30-70, 30-60, 30-50, 30-40, 35-100, 35-90, 35-80, 35-70, 35-60, 35-50, 35-40, 35-30, 40-100, 40-90, 40-80, 40-70, 40-60, 40-50, 45-100, 45-90, 45-80, 45-70, 45-60, 45-50, 50-100, 50-90, 50-80, 50-70, 50-60, 55-100, 55-90, 55-80, 55-70, 55-60, 60-100, 60-90, 60-80, 60-70, 65-100, 65-90, 65-80, 65-70, 70-100, 70-90, 70-80, 75-100, 75-90, 75-80, 80-100, 80-90, 90-100, and the like, or any dose increments of the doses listed above. It is understood by those skilled in the art that the doses of the peptides and analogs of the invention are generally provided as a dose to be administered to a subject per day. It is further understood by those skilled in the art that a dose can be adjusted by increasing or decreasing the dose depending on the responsivenes of the subject, the weight of the subject, and so forth, as well known by a physician or clinician skilled in the art. The peptides or analogs of Tables 2 or 3, or other peptides or analogs disclosed herein or the formulas disclosed herein, can be provided in a composition at the indicated doses, as disclosed herein. In a particular embodiment, the composition can comprise the peptide or analog of SEQ ID NO:12 or SEQ ID NO:31 at the indicated doses.

As described herein, the peptides and analogs of the invention are particularly useful for treating certain diseases and disorders. For example, the peptides or analogs of the invention can be used for treating impaired pancreatic function, treating a metabolic disease, promoting neuroprotection or nerve regeneration, promoting liver regeneration or inhibiting inflammation. Thus, the invention additionally provides compositions of the invention for treating impaired pancreatic function, treating a metabolic disease, promoting neuroprotection or nerve regeneration, promoting liver regeneration or inhibiting inflammation. Such compositions can comprise a peptide or analog such as those disclosed herein in Tables 2 or 3, or other peptides or analogs disclosed herein or the formulas disclosed herein. In a particular embodiment, the composition can comprise the peptide or analog of SEQ ID NO:12 or SEQ ID NO:31. The use of the peptides and analogs of the invention in such therapeutic applications are described below in more detail.

If desired, the peptides or analogs of the invention can be administered in combination. For example, a combination of two or more peptides or analogs of the invention, including those disclosed herein and shown in Tables 2 and 3, or other peptides or analogs disclosed herein or the formulas disclosed herein, for example, the peptide or analog of SEQ ID NO:12 or SEQ ID NO:31, can be administered for a method of treatment as disclosed herein. Such a combination can be administered concurrently, either in separate formulations or combined into the same formulation, depending on the peptides being administered and the compatibility of the formulations for the peptides or analogs of the invention. Alternatively, the two or more peptides or analogs of the invention can be administered sequentially, including on the same day or staggered on separate days.

Furthermore, it is understood by those skilled in the art that the peptide and analogs of the invention can optionally be administered with drugs or therapeutic agents for treating a condition. For example, in the case of treating diabetes or related conditions, other anti-diabetic drugs can be administered with the peptides or analogs of the invention. It is understood that such a co-administration can occur concurrently, either in separate formulations or combined into the same formulation, depending on the drugs being administered and the compatibility of the formulations for the peptides or analogs of the invention. Alternatively, the co-administration can occur sequentially, including on the same day or staggered on separate days. One skilled in the art will understand appropriate administration regimens suitable for effective deliver of a peptide or analog of the invention with another drug or therapeutic agent. It is further understood that the administration of peptide or analog can be intermittent.

In the case of treating insulin or related disorders, suitable anti-diabetic drugs include, but are not limited to, insulin, pramlintide, GLP-1 receptor agonists, oral anti-diabetic agents, and the like. Exemplary anti-diabetic drugs include, but are not limited to, insulin, meglitinides, for example, repaglinide (Prandin™) and nateglinide (Starlix™); sulfonylureas, for example, glipizide (Glucotrol™), glimepiride (Amaryl™), and glyburide (DiaBeta™, Glynase™); dipeptidy peptidase-4 (DPP-4) inhibitors, for example, saxagliptin (Onglyza™), sitagliptin (Januvia™), and linagliptin (Tradjenta™); biguanides, for example, metformin (Fortamet™, Glucophage™); thiazolidinediones, for example, rosiglitazone (Avandia™) and pioglitazone (Actos™); alpha-glucosidase inhibitors, for example, acarbose (Precose™) and miglitol (Glyset™); amylin mimetics, for example, pramlintide (Symlin™); and incretin mimetics, for example, exenatide (Byetta™) and liraglutide (Victoza™). Thus, in methods and uses of the invention for treating diabetes or related conditions, an anti-diabetic drug can be administered with a peptide or analog of the invention. For type 2 diabetes, islet neogenic agents such as the peptides or analogs of the invention can be utilized in patients with a good level of glucose control via life style modification or with a combination of anti-diabetic agents such as metformin, thiazolidinediones, GLP-1, insulin, and the like as described above, to allow the maturation of newly formed islets.

Type 1 diabetes and latent autoimmune diabetes in adults (LADA) are both autoimmune diseases. Therefore, in the case of a subject having type 1 diabetes or LADA, another therapeutic agent that can be administered with a peptide or analog of the invention can be, for example, an immune modulatory agent. The immunomodulatory agent can be used to block or reduce the destruction of neogenic islet or beta cells associated with autoimmunity. Exemplary immunodulatory agents include, but are not limited to, sirolimus (rapamycin, Rapamune™), tacrolimus (FK 506, Prograf™), lisofylline, antithymocyte globulin, basiliximab (Simulect™), DiaPep277™, and the like. It is known that islets are subject to glucose toxicity, lipotoxicity, and immune attack (for T1D). For type 1 diabetes, islet neogenic agents such as the peptides or analogs of the invention can be utilized in patients with good glycemic control and a combination of immune modulating agents to protect the newly developed islets from immune attack.

As described herein, the peptides and analogs of the invention exhibit unexpected properties over that of the parent INGAP-PP and HIP peptides, including the peptides and analogs of Tables 2 and 3 that are not the parent INGAP-PP or HIP peptides. As disclosed herein, peptides and analogs of the invention exhibit improved stability in culture medium and plasma over that of the parent peptide (see Example III and XI). The peptide analogs of the invention also were effective at significantly improving blood glucose, fasting insulin and oral glucose tolerance (see Example IV). The peptide analogs of the invention also exhibit a significantly increased islet neogenic effect than the parent peptide (see Example V, Example VIII and Example IX). Further, the peptide analogs of the invention exhibit a significantly increased ability to stimulate insulin secretion in primary pancreatic islet cells (see Example VI). Additionally, peptide analogs of the invention exhibited superior pharmacokinetic properties (see Examples VII and X). The numerous unexpected and superior properties of the peptides and analogs of the invention indicate that the peptides and analogs of the invention, including the peptides and analogs of Tables 2 and 3, including other peptides or analogs disclosed herein or formulas disclosed herein, that are not the parent INGAP-PP or HIP peptides, for example, SEQ ID NO:12 or SEQ ID NO:31, can be utilized for therapeutic applications.

In addition, the peptides and analogs of the invention were found to induce extra islet insulin positive β-cell clusters (see Example VIII). The peptide analogs were effective at $\frac{1}{10}$ the dose of the parent INGAP-PP peptide. Also, the islet neogenesis effects of peptide analogs were determined as reflected by pancreatic islet size distribution (see Example IX). The peptide analogs were effective at $\frac{1}{100}$ the dose of the parent INGAP-PP peptide. Thus, the peptides and analogs of the invetion can exhibit greater potency than the parent INGAP-PP or HIP peptide. It is known in the art that neogenic islets can be derived from pancreatic ductal or acinar cells (see Yatoh et al., *Diabetes* 56:1802-1809 (2007); Lipsett and Finegood, *Diabetes* 51:1834-1841 (2002)). Thus, the peptides and analogs of the invention can be used to produce neogenic islets from pancreatic ductal and/or acinar cells.

In a further embodiment, the invention provides a method for ameliorating a sign or symptom associated with impaired pancreatic function comprising administering a peptide or analog of the invention. Such peptides or analogs of the invention can be, for example, a peptide or analog of Tables 2 or 3, including other peptides or analogs disclosed herein or formulas disclosed herein. In a particular embodiment, the invention provides a method for ameliorating a sign or symptom associated with impaired pancreatic function comprising administering a peptide or analog of SEQ ID NO:12 or SEQ ID NO:31. A disease or condition associated with impaired pancreatic function includes, but is not limited to, type 1 diabetes, type 2 diabetes, latent autoimmune diabetes in adults (LADA), impaired fasting glucose, impaired glucose tolerance, insulin deficiency, fasting hyperinsulinemia, insulin resistance, or impaired fasting insulin levels, or a combination thereof. The pancreas produces insulin for regulation of blood glucose. In conditions such as type 1 and type 2 diabetes and LADA, the body cannot respond normally to glucose production, leading to a number of related conditions (see *Cecil Textbook of Medicine*, Bennett and Plum, eds., 20th ed., W. B. Saunders, Philadelphia (1996); *Harrison's Principles of Internal Medicine*, Fauci et al., eds., 14th ed., McGraw-Hill, New York (1998)). It is understood by those skilled in the art that such conditions, which are correlated with decreased function of the pancreas, are included within the meaning of impaired pancreatic function.

Diabetes mellitus is a serious metabolic disease that is defined by the presence of chronically elevated levels of blood glucose (hyperglycemia). This state of hyperglycemia is the result of a relative or absolute lack of activity of the peptide hormone, insulin. Insulin is produced and secreted by the β-cells of the pancreas. Insulin promotes glucose utilization, protein synthesis, and the formation and storage of carbohydrate energy as glycogen. Glucose is stored in the body as glycogen, a form of polymerized glucose, which may be converted back into glucose to meet metabolism requirements. Under normal conditions, insulin is secreted at both a basal rate and at enhanced rates following glucose stimulation, all to maintain metabolic homeostasis by the conversion of glucose into glycogen.

The term diabetes mellitus encompasses several different hyperglycemic states. These states include type 1 (insulin-dependent diabetes mellitus or IDDM) and type 2 (non-insulin dependent diabetes mellitus or NIDDM) diabetes. The hyperglycemia present in individuals with type 1 diabetes is associated with deficient, reduced, or nonexistent levels of insulin which are insufficient to maintain blood glucose levels within the physiological range. Treatment of type 1 diabetes involves administration of replacement doses of insulin, generally by a parenteral route. The hyperglycemia present in individuals with type 2 diabetes is initially associated with normal or elevated levels of insulin; however, these individuals are unable to maintain metabolic homeostasis due to a state of insulin resistance in peripheral tissues and liver and, as the disease advances, due to a progressive deterioration of the pancreatic β cells which are responsible for the secretion of insulin. Thus, initial therapy of type 2 diabetes may be based on diet and lifestyle changes augmented by therapy with oral hypoglycemic agents such as sulfonylureas. Insulin therapy is often required, however, especially in the latter states of the disease, in order to produce some control of hyperglycemia and minimize complications of the disease. It is known that, in type 2 diabetes, beta cells are susceptible to glucose toxicity, lipotoxicity, chronic oxidative stress, and combinations thereof; in type 1 diabetes, β cells are primarily subject to immune attack and glucose toxicity. A relatively stable blood glucose and lipid level can provide a healthier environment for neogenic islets to develop into mature and functional islets for type 2 diabetic patients; for type 1 diabetes, additional immune modulating agents can provide a desirable physiological environment for the development of neogenic islets.

The invention additionally provides a method for ameliorating a sign or symptom associated with a metabolic disease in a subject comprising administering a peptide or analog of the invention to the subject. Such a metabolic disease includes, but is not limited to, diabetes, pre-diabetes or metabolic syndrome. Such peptides or analogs of the invention can be, for example, a peptide or analog of Tables 2 or 3, including other peptides or analogs disclosed herein or formulas disclosed herein. In a particular embodiment, the invention provides a method for ameliorating a sign or symptom associated with a metabolic disease in a subject comprising administering a peptide or analog of SEQ ID NO:12 or SEQ ID NO:31.

Prediabetes is a condition where blood sugar level is higher than normal but not yet high enough to be classified as type 2 diabetes. Metabolic syndrome is a name for a group of risk factors that occur together and increase the risk for coronary artery disease, stroke, and type 2 diabetes. The two most important risk factors for metabolic syndrome are extra weight around the middle and upper parts of the body (central obesity, so-called "apple-shaped") and insulin resistance, where the body uses insulin less effectively than normal. Insulin is needed to help control the amount of sugar in the body. As a result, blood sugar and fat levels rise. Metabolic syndrome is considered to be present if a subject has three or more of the following signs: blood pressure equal to or higher than 130/85 mmHg; fasting blood sugar (glucose) equal to or higher than 100 mg/dL; large waist circumference (length around the waist)(men, 40 inches or more; women, 35 inches or more); low HDL cholesterol (men, under 40 mg/dL; women, under 50 mg/dL); triglycerides equal to or higher than 150 mg/dL.

One skilled in the art will readily understand and can readily determine appropriate indicators of the effectiveness of the peptides or analogs of the invention at ameliorating a sign or symptom associated with a condition or disease associated with impaired pancreatic function and/or metabolic disease. For example, both type 1 and type 2 diabetes are well characterized diseases with a number of known parameters for diagnosing and/or monitoring the progression of the disease and/or to monitor the effectiveness of a therapy. Such parameters include, but are not limited to, plasma glucose levels, fasting glucose levels, oral glucose tolerance test (OGTT), insulin levels, fasting insulin levels, glycosylated hemoglobin levels, and the like.

The peptides or analogs of the invention can therefore be used to ameliorate any one or more of the signs or symptoms associated with impaired pancreatic function and/or metabolic disease. In the case of diabetes, such signs or symptoms include, but are not limited to, impaired glucose tolerance, increased blood glucose (in particular above 200 mg/dl), increased fasting blood glucose (in particular above 140 mg/dl), increased postprandial (after eating) blood glucose, insulin deficiency, fasting hyperinsulinemia, insulin resistance, impaired fasting insulin levels, increased glycosylated hemoglobin (HbA1c), and the like. Such signs or symptoms are well known to those skilled in the art and can be routinely determined by those skilled in the art, including tests available through medical testing laboratories. In an embodiment of the invention, the invention provides a method of reducing a sign or symptom associated with a condition such as diabetes, for example, a method of reducing impaired glucose tolerance, blood glucose, in particular daily average blood glucose concentration, fasting blood glucose, postprandial (after eating) blood glucose, insulin deficiency, fasting hyperinsulinemia, insulin resistance, impaired fasting insulin levels, glycosylated hemoglobin (HbA1c), arginine-stimulated C-peptide, advanced glycation end products (AGE), or a combination thereof, by administering a peptide or analog of the invention. The method utilizes peptides or analogs of the invention. Such peptides or analogs of the invention can be, for example, a peptide or analog of Tables 2 or 3, including other peptides or analogs disclosed herein or formulas disclosed herein. In a particular embodiment, the invention provides a method of reducing a sign or symptom associated with a condition such as diabetes, for example, a method of reducing impaired glucose tolerance, blood glucose, in particular daily average blood glucose concentration, fasting blood glucose, postprandial (after eating) blood glucose, insulin deficiency, fasting hyperinsulinemia, insulin resistance, impaired fasting insulin levels, glycosylated hemoglobin (HbA1c), arginine-stimulated C-peptide, advanced glycation end products (AGE), or a combination thereof, by administering a peptide or analog of SEQ ID NO:12 or SEQ ID NO:31. Methods of monitoring the effectiveness of a drug for treating diabetes are well known to those skilled in the art (see, for example, *Cecil Textbook of Medicine*, supra; *Harrison's Principles of Internal Medicine* supra, Dungan et al., *Diabetes/Metabolism Res. Rev.* 25:558-565 (2009); U.S. Pat. No. 8,329,648). Thus, the invention provides a method of reducing in a diabetic subject impaired glucose tolerance, blood glucose, fasting blood glucose, postprandial blood glucose, insulin deficiency, fasting hyperinsulinemia, insulin resistance, impaired fasting insulin levels, glycosylated hemoglobin (HbA1c), arginine-stimulated C-peptide, advanced glycation end products (AGE), or a combination thereof, by administering a peptide or analog of the invention to the subject. Such peptides or analogs of the invention can be, for example, a peptide or analog of Tables 2 or 3, including other peptides or analogs disclosed herein or formulas disclosed herein. In a particular embodiment, the invention provides a method of reducing in a diabetic subject impaired glucose tolerance, blood glucose, fasting blood glucose, postprandial blood glucose, insulin deficiency, fasting hyperinsulinemia, insulin resistance, impaired fasting insulin levels, glycosylated hemoglobin (HbA1c), arginine-stimulated C-peptide, advanced glycation end products (AGE), or a combination thereof, by administering a peptide or analog of SEQ ID NO:12 or SEQ ID NO:31.

As disclosed herein, the peptides and analogs of the invention were particularly effective at stimulating pancreatic islet cell growth and induction of β-cell clusters (see Example V, Example VIII and Example IX). Exemplary peptides and analogs of the invention exhibited improved islet neogenic effect over parent peptide (Example V, Example VIII and Example IX).

Thus, the invention additionally provides a method for stimulating pancreatic islet cell growth by contacting a pancreatic islet cell in vitro with a peptide or analog of the invention, whereby proliferation of the pancreatic islet cell is stimulated. Such peptides or analogs of the invention can be, for example, a peptide or analog of Tables 2 or 3, including other peptides or analogs disclosed herein or formulas disclosed herein. In a particular embodiment, the invention provides a method for stimulating pancreatic islet cell growth by contacting a pancreatic islet cell in vitro with a peptide or analog of SEQ ID NO:12 or SEQ ID NO:31. In another embodiment, the invention provides a method of producing a population of pancreatic islet cells, comprising contacting one or more pancreatic islet cells in vitro with a peptide or analog of the invention, whereby proliferation of the one or more pancreatic islet cells is stimulated and a population of pancreatic islet cells is produced. Such peptides or analogs of the invention can be, for example, a peptide or analog of Tables 2 or 3, including other peptides or analogs disclosed herein or formulas disclosed herein. In a particular embodiment, the invention provides a method of producing a population of pancreatic islet cells, comprising contacting one or more pancreatic islet cells in vitro with a peptide or analog of SEQ ID NO:12 or SEQ ID NO:31. The methods of the invention can be used for ex vivo islet induction, expansion and proliferation for transplantation and for increasing the survival of transplanted islets in vivo utilizing peptides or analogs of the invention. Such peptides or analogs of the invention can be, for example, a peptide or analog of Tables 2 or 3, including other peptides or analogs disclosed herein or formulas disclosed herein. In a particular embodiment, the invention provides a method for ex vivo islet induction, expansion and proliferation for transplantation and for increasing the survival of transplanted islets in vivo ameliorating using a peptide or analog of SEQ ID NO:12 or SEQ ID NO:31.

The methods of the invention can additionally be used to preserve isolated islet cells using peptides or analogs of the invention. Such peptides or analogs of the invention can be, for example, a peptide or analog of Tables 2 or 3, including other peptides or analogs disclosed herein or formulas disclosed herein. In a particular embodiment, the invention provides a method to preserve isolated islet cells using a peptide or analog of SEQ ID NO:12 or SEQ ID NO:31. Thus, the invention provides methods of ex vivo islet expansion and proliferation for transplantation using the peptides or analogs of the invention by contacting islet cells in vitro, increasing the islet cell numbers and optionally using the cells for transplantation. Such peptides or analogs of the invention can be, for example, a peptide or analog of Tables 2 or 3, including other peptides or analogs disclosed herein or formulas disclosed herein. In a particular embodiment, the invention provides a method of ex vivo islet expansion and proliferation for transplantation using the peptides or analogs of the invention by contacting islet cells in vitro, increasing the islet cell numbers and optionally using the cells for transplantation by contacting the cells with a peptide or analog of SEQ ID NO:12 or SEQ ID NO:31. The invention also provides a method of increasing the survival of transplanted islets in vivo by administering to a subject a peptide or analog of the invention, wherein the subject is the recipient of transplanted islet cells. Such peptides or analogs of the invention can be, for example, a peptide or analog of Tables 2 or 3, including other peptides or analogs disclosed herein or formulas disclosed herein. In a particular embodiment, the invention provides a method of increasing the survival of transplanted islets in vivo by administering to a subject by administering a peptide or analog of SEQ ID NO:12 or SEQ ID NO:31. The peptides or analogs of the invention can thus be used to generate cells for transplantation using in vitro and ex vivo methods as well as to increase survival of transplanted islet cells. Such transplanted cells can be obtained from the in vitro methods using the peptides or analogs of the invention or from traditional transplant sources of islet cells such as cadavers. The methods of the invention can further be used to treat a patient with a loss or impaired pancreatic function by administering a peptide or analog of the invention. Such a loss or impairment of pancreatic function can occur, for example, from partial pancreatectomy, such as due to injury, inflammation, neoplasms, hyperinsulinemic hypoglycemia, and the like, or from conditions that affect pancreas function such as cystic fibrosis. Such peptides or analogs of the invention can be, for example, a peptide or analog of Tables 2 or 3, including other peptides or analogs disclosed herein or formulas disclosed herein. In a particular embodiment, the invention provides a method of treating a patient with a loss or impaired pancreatic function by administering a peptide or analog of SEQ ID NO:12 or SEQ ID NO:31.

In a particular embodiment, the one or more pancreatic islet cells can be obtained from a subject. The population of pancreatic islet cells produced by stimulating proliferation of the pancreatic islet cells can be used, for example, for transplantation into a subject and restoration of pancreatic islet cell function. Thus, a method of the invention can further comprise the step of transplanting the population of pancreatic islet cells into a subject. In a particular embodiment, the one or more pancreatic cells are obtained from the subject into which the population of pancreatic islet cells is to be transplanted. Alternatively, the pancreatic islet cells to be transplanted are obtained from a suitable donor having a compatible blood type.

Transplantation of pancreatic islets has been described previously (see, for example, Shapiro et al., *N. Engl. J. Med.* 343:230-238 (2000)). Pancreatic islet cells can be obtained from the subject or, alternatively, from a suitable donor, including islet cells harvested from a cadaver. Generally, the transplant recipient is administered immunosuppressive drugs to decrease rejection of the islet cells (see, for example, immunosuppressive drugs described herein). The use of suitable immunosuppressive drugs are well known in the field of organ or cell transplantation. Thus, in methods of the invention in which pancreatic islet cells are stimulated to proliferate in vitro to produce a population of pancreatic islet cells, such a population can be transplanted into a subject using well known methods of pancreatic islet cell transplantation. In addition, peptides or analogs of the invention can be used to induce differentiation of pancreatic ductal cells into islet cells, in particular beta-cells (see Yatoh et al., *Diabetes* 56:1802-1809 (2007)). Thus, the invention further provides a method of differentiating pancreatic ductal cells into islet cells by contacting a pancreatic ductal cell with a peptide or analog of the invention. Such peptides or analogs of the invention can be, for example, a peptide or analog of Tables 2 or 3, including other peptides or analogs disclosed herein or formulas disclosed herein. In a particular embodiment, the invention provides a method of differentiating pancreatic ductal cells into islet cells by contacting a pancreatic ductal cell with a peptide or analog of SEQ ID NO:12 or SEQ ID NO:31. When the method is performed where the pancreatic ductal cell is contacted in vitro, a population of differentiated pancreatic ductal cells can be generated and used for transplantation, as described herein.

The invention further provides a method for increasing the number of pancreatic islet cells in a subject comprising administering a peptide or analog of the invention to the subject. Such peptides or analogs of the invention can be, for example, a peptide or analog of Tables 2 or 3, including other peptides or analogs disclosed herein or formulas disclosed herein. In a particular embodiment, the invention provides a method for increasing the number of pancreatic islet cells in a subject comprising administering a peptide or analog of SEQ ID NO:12 or SEQ ID NO:31. Such a method of therapeutic treatment using peptides or analogs of the invention can be used to increase pancreatic islet cells in an individual, without the need to harvest pancreatic cells from the individual or identify a suitable donor and without the need to put the subject through complex transplantation procedures and the frequently required use of immunosuppressive agents if using donor cells not obtained from the patient.

As described previously, INGAP peptide has been shown to improve nerve function and enhance nerve regeneration in a diabetic mouse model (Tam et al., *FASEB J.* 18:1767-1769 (2004)). INGAP peptide was also shown to enhance neurite outgrowth in dorsal root ganglia neurons (Tam et al., *Biochem. Biophys. Res. Communic.* 291:649-654 (2002; Tam et al., *NeuroReport* 17:189-193 (2006)). As described herein, the peptides and analogs of the invention are significantly more active than the INGAP parent peptide and are expected to have a similar but more potent activity than INGAP. Thus, the invention provides a method for promoting neuroprotection or nerve regeneration by contacting a nerve cell with a peptide or analog the invention, thereby stimulating neuroprotection and/or nerve regeneration. Such peptides or analogs of the invention can be, for example, a peptide or analog of Tables 2 or 3, including other peptides or analogs disclosed herein or formulas disclosed herein. In a particular embodiment, the invention provides a method for promoting neuroprotection or nerve regeneration by contacting a nerve cell with a peptide or analog of SEQ ID NO:12 or SEQ ID NO:31. The contacting with a nerve cell can occur in vivo or in vitro. In the case where the nerve cell is contacted in vivo, the peptide or analog of the invention is administered to a subject as with other therapeutic methods disclosed herein. In the case where the nerve cell is contacted in vitro, the neuroprotected cell can be used in an ex vivo application and the cell administered to the subject. Such methods of introducing nerve cells by way of transplantation are well known to those skilled in the art (see, for example, Dunnett et al., *Brit. Med. Bulletin* 53:757-776 (1997)). Such transplantations have been performed to treat neurological conditions such as Parkinson's disease and Huntington's disease.

The HIP peptide has been described as accelerating liver regeneration (Lieu et al., *Hepatol.* 42:618-626 (2005). As described herein, the peptides and analogs of the invention are significantly more active than the HIP parent peptide and are expected to have a similar but more potent activity than HIP. Thus, the invention also provides a method for promoting liver regeneration by contacting a liver cell with a peptide or analog of the invention, thereby promoting liver regeneration. Such peptides or analogs of the invention can be, for example, a peptide or analog of Tables 2 or 3, including other peptides or analogs disclosed herein or formulas disclosed herein. In a particular embodiment, the invention provides a method for promoting liver regeneration by contacting a liver cell with a peptide or analog of SEQ ID NO:12 or SEQ ID NO:31. The contacting with a liver cell can occur in vivo or in vitro. In the case where the liver cell is contacted in vivo, the peptide or analog of the invention is administered to a subject as with other therapeutic methods disclosed herein. In the case where the liver cell is contacted in vitro, the liver cells can be induced to proliferate, for example, to produce a population of liver cells. The population of liver cells can be used in an ex vivo application and the cells administered to the subject. Methods for transplanting or grafting liver cells onto the liver of a subject are well known to those skilled in the art. The transplanted cells can be used to reconstitute injured, or metabolically defective, liver tissue. Liver cells can be infused into the portal vein or spleen from where cells migrate to the liver and take up permanence residence and perform the normal liver metabolic functions (see, for example, Khan et al., *Cell Transplant.* 19:409-418 (2010)).

The HIP protein (also referred to as Pancreatitis-associated protein (PAP)) has been found to exhibit anti-inflammatory activity in vivo and in vitro (Closa et al., *World J. Gastroenterol.* 13:170-174 (2007)). Therefore, the peptides and analogs of the invention are expected to exhibit anti-inflammatory activity. Therefore, the invention further provides a method for inhibiting inflammation by administering a peptide or analog of the invention. Such peptides or analogs of the invention can be, for example, a peptide or analog of Tables 2 or 3, including other peptides or analogs disclosed herein or formulas disclosed herein. In a particular embodiment, the invention provides a method for inhibiting inflammation by administering a peptide or analog of SEQ ID NO:12 or SEQ ID NO:31.

The invention also provides the use of a peptide or analog of the invention for preparation of a medicament for treating impaired pancreatic function, treating a metabolic disease, promoting neuroprotection or nerve regeneration, promoting liver regeneration or inhibiting inflammation in a subject. Such peptides or analogs of the invention can be, for example, a peptide or analog of Tables 2 or 3, including other peptides or analogs disclosed herein or formulas disclosed herein. In a particular embodiment, the invention provides use of a peptide or analog of the SEQ ID NO:12 or SEQ ID NO:31 for preparation of a medicament for treating impaired pancreatic function, treating a metabolic disease, promoting neuroprotection or nerve regeneration, promoting liver regeneration or inhibiting inflammation in a subject.

The invention additionally provides use of a peptide or analog of the invention for preparation of a medicament for treating impaired pancreatic function, treating a metabolic disease, promoting neuroprotection or nerve regeneration, promoting liver regeneration or inhibiting inflammation in a subject. Such uses can be, for example, to carry out the methods of the invention disclosed herein. Such peptides or analogs of the invention can be, for example, a peptide or analog of Tables 2 or 3, including other peptides or analogs disclosed herein or formulas disclosed herein. In a particular embodiment, the invention provides use of a peptide or analog of SEQ ID NO:12 or SEQ ID NO:31 for preparation of a medicament for treating impaired pancreatic function, treating a metabolic disease, promoting neuroprotection or nerve regeneration, promoting liver regeneration or inhibiting inflammation in a subject.

As described herein, the peptides and analogs of the invention can be used in a variety of methods. Such methods include, but not limited to, treating impaired pancreatic function, treating a metabolic disease, promoting neuroprotection or nerve regeneration, promoting liver regeneration or inhibiting inflammation. In many applications of the invention for a therapeutic application, the peptides or analogs of the invention are administered. However, it is understood that an alternative mode is to use gene therapy to express a peptide of the invention by administering a suitable gene therapy vector containing a nucleic acid encoding the peptide to a subject. Such gene therapy methods are described below in more detail and are well known to those skilled in the art (see, for example, Anderson, *Nature* 392 (Supp.):25-30 (1998)).

A gene delivery vehicle refers to a molecule that can carry inserted polynucleotides into a host cell. Examples of gene delivery vehicles are liposomes, micells biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

A peptide or analog of the invention can be delivered to a cell or tissue using a gene delivery vehicle. Gene delivery, gene transfer, transducing, and the like as used herein, are terms referring to the introduction of an exogenous polynucleotide (sometimes referred to as a transgene) into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide can be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art.

A viral vector refers to a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors, alphavirus vectors and the like. Alphavirus vectors, such as Semliki Forest virus-based vectors and Sindbis virus-based vectors, have also been developed for use in gene therapy and immunotherapy (see Schlesinger and Dubensky *Curr. Opin. Biotechnol.* 5:434-439 (1999) and Ying, et al. *Nat. Med.* 5(7):823-827 (1999)).

In aspects where gene transfer is mediated by a retroviral vector, a vector construct refers to the polynucleotide comprising the retroviral genome or part thereof, and a therapeutic gene. As used herein, retroviral mediated gene transfer or retroviral transduction carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism. Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes (see, for example, WO 95/27071). Ads do not require integration into the host cell genome. Recombinant Ad derived vectors, particularly those that reduce the potential for recombination and generation of wild-type virus, have also been constructed (see, for example, WO 95/00655 and WO 95/11984). Wild-type AAV has high infectivity and specificity integrating into the host cell's genome (see, for example, Hermonat and Muzyczka, *Proc. Natl. Acad. Sci. USA* 81:6466-6470 (1984) and Lebkowski et al., *Mol. Cell. Biol.* 8:3988-3996 (1988)).

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include DNA/liposome complexes, micelles and targeted viral protein-DNA complexes. Liposomes that also comprise a targeting antibody or fragment thereof can be used in the methods of this invention. To enhance delivery to a cell, the nucleic acid or proteins of this invention can be conjugated to antibodies or binding fragments thereof which bind cell surface antigens, for example, a cell surface marker found on pancreatic islet cells.

In yet another embodiment, the invention provides a method of introducing a peptide or analog of the invention into a subject by contacting a cell with a nucleic acid encoding a peptide or analog of the invention. The contacting of a cell with the nucleic acid can occur in vitro, for ex vivo applications, or in vivo. Such methods are often referred to as gene therapy methods. When the cell is contacted in vitro, the cells expressing the polynucleotide can be administered to the subject. Such methods permit the expression of a therapeutic protein or peptide, such as the peptides or analogs of the invention, for therapeutic applications. Such therapeutic applications can be used for treating various diseases and conditions, including but not limited to treating impaired pancreatic function, treating a metabolic disease, promoting neuroprotection or nerve regeneration, promoting liver regeneration or inhibiting inflammation, as disclosed herein.

It is understood that modifications which do not substantially affect the activity of the various embodiments of this invention are also provided within the definition of the invention provided herein. Accordingly, the following examples are intended to illustrate but not limit the present invention.

EXAMPLE I

Production of Peptides and Peptide Analogs

This example describes the production of peptides and peptide analogs.

All the peptides used in the studies were synthesized by solid phase peptide synthesis using 9-fluorenylmethoxy carbonyl (Fmoc) chemistry. In brief, a pre-weighed amount of 2-chlorotrityl chloride resin (1.6 mmol/g) was swelled in dichloromethane (DCM). For peptides with an amidated C-terminus, Rink amide resin was used instead of 2-chlorotrityl chloride resin. Fmoc-preactivated amino acids were used for the coupling reactions in the presence of hydroxybenzotriazole (Sigma Chemical Co., St. Louis, Mo., USA) in dimethylformamide (DMF). Excess amino acids were used throughout the synthesis. Chain elongation reaction was performed followed by Fmoc deprotection in 20% piperidine in DMF. When the chain elongation reaction was finished, the Fmoc protecting groups were removed from the N terminus of the peptides by 25% piperidine in DMF followed by washing with DMF for four times. For peptides with an acetylated N-terminus, before trifluoroacetic acid (TFA) cleavage, a solution of 20% acetic anhydride dissolved in DMF was added at a ratio of 7 mL/g resin, reacted for 30 mins, followed by 4 times washes with DMF and DCM. Following washing for four times with DMF and DCM, the resin was dried under vacuum. Subsequently, the prepared peptides were cleaved from the resin using standard TFA cleavage procedures in TFA with 5% $H_2O$ followed by multiple ether extractions. All synthetic peptides were purified to >95% by reverse-phase high-pressure liquid chromatography performed with a liquid chromatograph. Peptides were analyzed by mass spectrometry to confirm the identity and purity.

For in vitro and ex-vivo studies, the above prepared peptides were dissolved in double distilled water to make a stock solution, and in the in vivo efficacy study they were reconstituted in sterile normal saline to reach the desired concentration. The final peptide solution was filtered through a 0.22 µm membrane to make it sterile.

The peptides and analogs can also be produced using other well known methods, including manufacturing the peptides using a method of peptide synthesis or expressing nucleic acids that code for the desired peptides or peptide analogs. Thus, when the analogs include one or more non-standard amino acids, it is more likely that they will be produced by a chemical synthetic method. When the peptides include only one or more substitutions with standard amino acids, the peptides can be expressed from an expression vector using well known expression methods.

The particular peptides used in the experiments below can be found in Tables 1-3.

EXAMPLE II

Stimulatory Effect of Peptides on Cell Proliferation

This example describes the effect of peptides and analogs on pancreatic cell growth.

To measure cell proliferation, a bromodeoxyuridine (BrdU) ELISA assay was performed. Briefly, ARIP cells (ATCC (American Type Culture Collection), Manassas Va. USA), a rat pancreatic ductal cell line, were cultured in F-12K medium (Gibco-BRL, Gaithersburg, Md., USA) containing 10% fetal bovine serum (FBS; HyClone, Thermo Fisher Scientific Inc.; Waltham Mass. USA), 100 µg/ml streptomycin and 100 µg/ml penicillin in a cell incubator. ARIP cells were seeded into 96-well culture plates at 8000 or 0 (as blank control) cells/well in a volume of 50 µl cell culture medium and incubated overnight for the following experiments. On the second day, after replacing the medium with medium without serum, 50 µl serum-free cell culture medium containing test peptides at a series concentrations (final concentrations were 10 µM, 5 µM, 1 µM, 500 nM, 100 nM, 50 nM, 10 nM and 1 nM) were added to seeded cells. Medium without compound was added to negative control and background control wells. The medium was replaced at 24 h and 48 h respectively with fresh medium. At 69 hours, the medium was supplemented with 10 µl bromodeoxyuridine (BrdU) labeling solution (except the background control wells) from a BrdU cell proliferation ELISA kit (Roche Applied Science; Indianapolis Ind. USA), and incubated for an additional 3 hours. At 72 hours, labeling medium was removed, and 200 µl/well of FixDenat solution was added. After 30 minutes of incubation time, FixDenat solution was removed thoroughly and 100 µl/well of anti-BrdU antibody working solution was added and incubated at room temperature (RT) for 90 minutes. Antibody conjugate was removed and wells were rinsed three times with 250 µl/well Washing solution (1× PBS). After removing washing solution, 100 µl/well of Substrate solution was added and incubated at RT for 15 min, then 25 µl/well of 1 M $H_2SO_4$ was added, and the plate was incubated for about 1 min on the shaker to mix thoroughly. The absorbance at 450 nm (reference wavelength 690 nm) on an EnVision™ plate reader (Perkin Elmer, Boston Mass.) within 5 min after adding the stop solution was measured.

To test for cell viability, a CellTiter-Glo™ (CTG) assay (Promega, Madison Wis.) was performed. Briefly, ARIP cells (ATCC, cat#CRL-1674) were cultured in F-12K medium (Gibco-BRL) containing 10% fetal bovine serum (FBS; HyClone), 100 µg/ml streptomycin and 100 µg/ml penicillin in a cell incubator. ARIP cells were seeded into 96-well culture plates at 8000 and 0 (as blank control) cells/well in the volume of 50 µl cell culture medium and incubated overnight for the following experiments. On the second day, after replacing the medium with medium without serum, 50 µl serum-free cell culture medium containing test peptides at a series of concentrations (final concentrations were 10 µM, 5 µM, 1 µM, 500 nM, 100 nM, 50 nM, 10 nM and 1 nM) were added to seeded cells. Medium without compound was added to negative control and background control wells. The medium was replaced at 24 h and 48 h respectively with fresh medum. At 72 hours, 25 µl of CellTiter-Glo® reagent was added to each well and mixed on an orbital shaker for 2 mins. Luminescence signal was quantified on an EnVision™ plate reader after a 10 minute incubation at room temperature.

FIG. 1 shows the comparison of ARIP cell proliferation in the presence of 100 nM of INGAP Scrambled PP 1 (Peptide 3), INGAP-PP (Peptide 1), and Peptide 7 (peptides shown in Table 2). FIG. 1 shows that there was an increase in cell number at a peptide concentration of 100 nM. Peptide 7 showed a significantly higher percentage increase in cell number compared to the INGAP scrambled peptide, a negative control, and INGAP-PP peptide.

EXAMPLE III

Peptide Stability Studies

This example describes stability studies of peptides in various conditions.

To determine the stability of peptides in culture medium, a certain amount of selected peptides was accurately weighed and dissolved in distilled water to 5 mg/mL as a stock solution. The stock solution was diluted to 0.25 mg/mL with F-12K medium (Gibco-BRL, Gaithersburg, Md., USA) as working solution. A volume of 100 µL of each working solution was transferred into individual sample vials. The sample vials were incubated in a 37° C. incubator for 0, 24, 48 and 72 hours before being analyzed and quantitated by HPLC.

Figure 2:
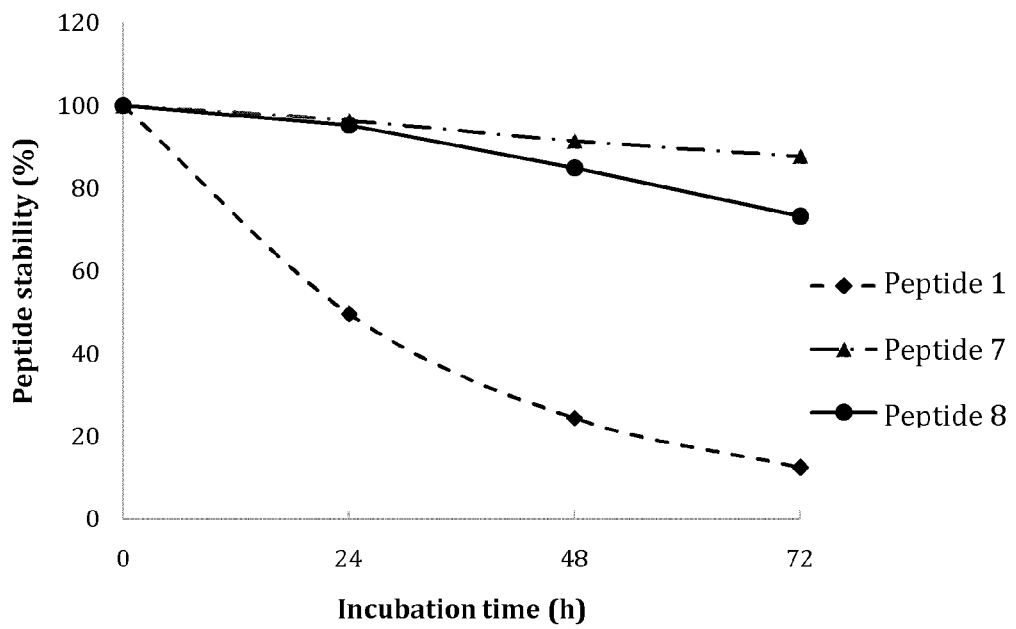
FIG. 2 shows a stability comparison in culture medium of INGAP-PP (Peptide 1) and selected peptide analogs, Peptide 7 and Peptide 8 (see Table 2).

FIG. 2 shows the stability of compounds in culture medium. In particular, FIG. 2 shows a stability comparison in culture medium of INGAP-PP (Peptide 1) and selected peptide analogs, Peptide 7 and Peptide 8 (see Table 2). As shown in FIG. 2, peptide analogs Peptide 7 and Peptide 8 were significantly more stable than INGAP-PP peptide in culture medium.

The stability of peptides was also tested in mouse and human plasma. Briefly, a certain amount of peptides and eucatropine powder (positive control) was accurately weighed. Test compounds were dissolved in 50% methanol-water solution and diluted to 20 mg/mL, and eucatropine was dissolved in dimethylsulfoxide (DMSO) and diluted to 10 mM, as a stock solution. Eucatropine stock solution was diluted to 0.2 mM with DMSO as a working solution. A stop reagent was prepared containing 200 ng/mL midazolam and tolbutamide in acetonitrile. A volume of 300 µL of stop solution was added to each well of a 96-well deep-well plate placed on ice beforehand.

For the stability studies, peptides and eucatropine were spiked into plasma respectively, mixed well, and then 100 µL of each mixture solution was transferred into the pre-cooled stop reagent as 0 time point sample. The remaining mixtures were incubated in a 37° C. water bath with shaking at 100 rpm (n=2). The final incubation concentration was 1 µM for eucatropine and 100 µg/mL for all test compounds.

At desired time points, 100 µL of incubation mixture was transferred to the stop reagent to precipitate proteins. Samples were vortexed and centrifuged at RCF 5000×g for 10 minutes, and supernatant was transferred to a test plate. The samples were analyzed by LC-MS/MS.

Slope was calculated by plotting the natural logarithm of the percentage of remaining amount of test compounds and time, and $T_{1/2}$ was calculated in accordance with the following formula.

$$T_{1/2} = \frac{0.693}{-\text{slope}}$$

Figure 3:
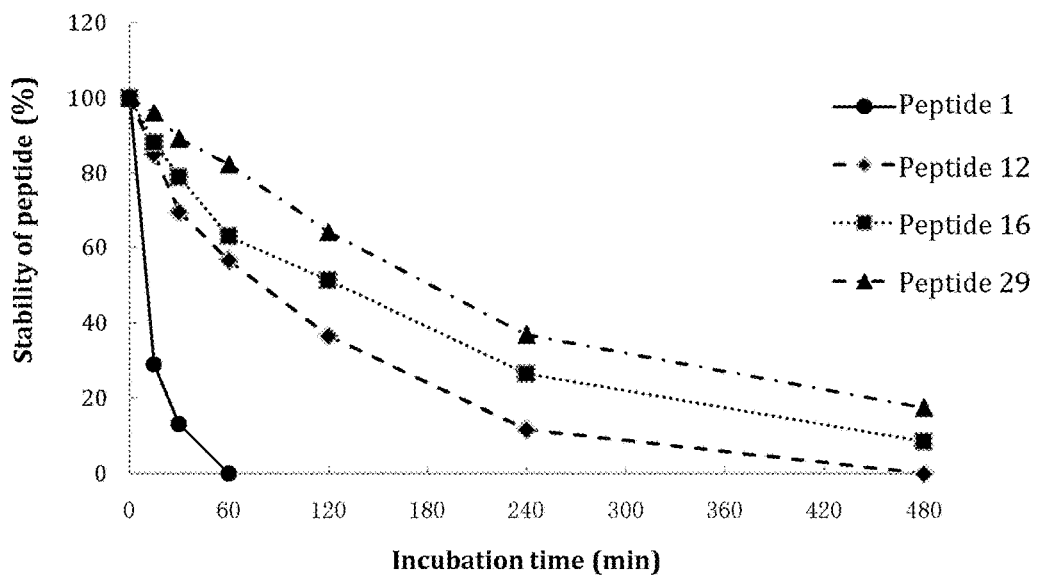
FIG. 3 shows a stability comparison in mouse plasma of INGAP-PP (Peptide 1) and selected peptide analogs, Peptide 12, Peptide 16 and Peptide 29 (see Table 2).

For stability in mouse plasma, the incubation time was 0, 5, 15, 30 and 60 min for Peptide 1 and eucatropine; 0, 15, 30, 60, 120, 240 and 480 min for Peptide 12, Peptide 16 and Peptide 29. FIG. 3 shows stability of compounds in mouse plasma. In particular, FIG. 3 shows a stability comparison in mouse plasma of INGAP-PP (Peptide 1) and selected peptide analogs, Peptide 12, Peptide 16 and Peptide 29 (see Table 2). As shown in FIG. 3, peptide analogs Peptide 12, Peptide 16 and Peptide 29 exhibited good stability in mouse plasma and were more stable than INGAP-PP (Peptide 1).

Figure 5:
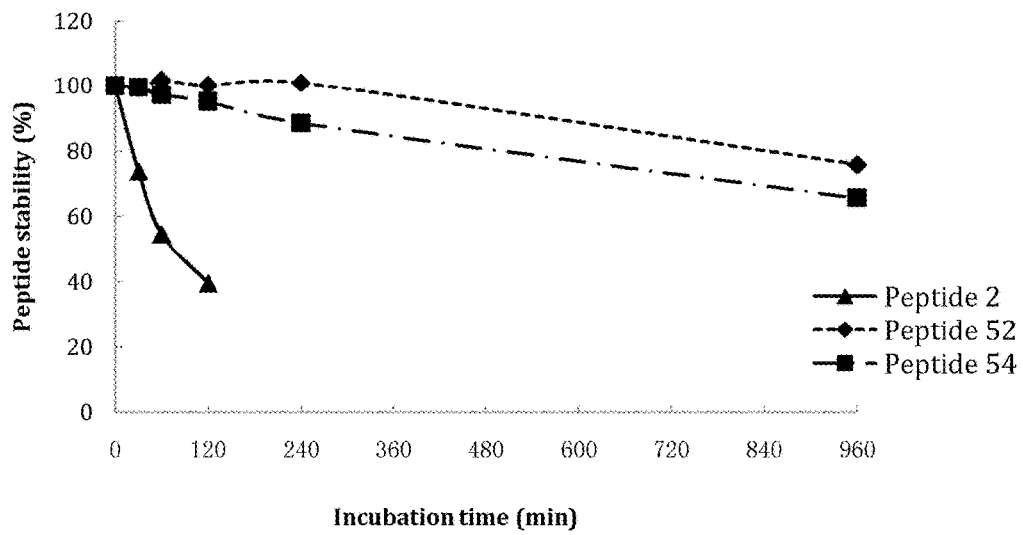
FIG. 5 shows a stability comparison in mouse plasma of HIP (Peptide 2) and selected peptide analogs, Peptide 52 and Peptide 54 (see Table 3).

In another stability study in mouse plasma, the incubation time was 0, 30, 60 and 120 min for Peptide 2 and eucatropine; 0, 30, 60, 120, 240 and 960 min for Peptide 52 and Peptide 54. FIG. 5 shows stability of compounds in mouse plasma. In particular, FIG. 5 shows a stability comparison in mouse plasma of HIP (Peptide 2) and selected peptide analogs, Peptide 52 and Peptide 54 (see Table 3). As shown in FIG. 5, peptide analogs Peptide 52 and Peptide 54 exhibited good stability in mouse plasma and were significantly more stable than HIP (Peptide 2).

Figure 4:
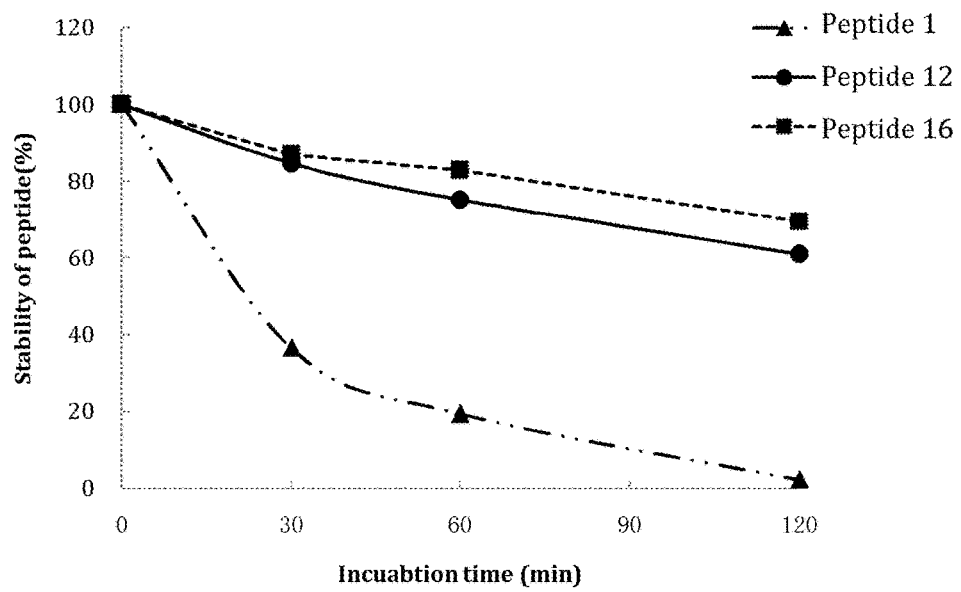
FIG. 4 shows a stability comparison in human plasma of INGAP-PP (Peptide 1) and selected peptide analogs, Peptide 12 and Peptide 16 (see Table 2).

For stability in human plasma, the incubation time was 0, 30, 60 and 120 min for Peptide 1, Peptide 12, Peptide 16 and eucatropine. FIG. 4 shows the stability of compounds in human plasma. In particular, FIG. 4 shows a stability comparison in human plasma of INGAP-PP (Peptide 1) and selected peptide analogs, Peptide 12 and Peptide 16 (see Table 2). As shown in FIG. 4, peptide analogs Peptide 12 and Peptide 16 exhibited good stability in human plasma and were significantly more stable than INGAP-PP (Peptide 1).

These results demonstrate that various peptide analogs exhibit good stability under various conditions, including culture medium and mouse and human plasma, and exhibit superior stability over INGAP-PP and HIP peptides.

EXAMPLE IV

Efficacy of Peptide Analogs in a Diabetic Mouse Model

This example describes an in vivo efficacy study using a streptozotocin (STZ) induced diabetic mice model.

After acclimatization in the animal facility for one week, 6-8 weeks old C57BL/6J mice were administered low dose STZ at 40 mg/kg in citrate buffer for 5 consecutive days to establish a T1D animal model. Mice with blood glucose greater than 16.7 mmol/L at 5 days post last STZ injection were included in the study. These mice were then treated with INGAP-PP (Peptide 1) or Peptide 7 at the doses of 5 mg/kg (2.5 mg/kg, bid (twice a day)) or 25 mg/kg (12.5 mg/kg, bid) for 20 days before sacrifices. Two additional groups of diabetic mice were administered either saline or a peptide (Peptide 3) composed of a scrambled sequence of amino acids from Peptide 1 as control groups. Blood glucose and insulin levels were measured, and 20 days post the last dosing of test agents, an oral glucose tolerance test (OGTT) was performed in 6 hour fasted animals to determine the effect of Peptide 1 and Peptide 7. Blood samples obtained from the tail cut for glucose determination were detected with an ACCU-CHEK™ glucometer (Roche, ACCU-CHEK® Active), and insulin levels were determined with Rat/Mouse Insulin Elisa kit (Millipore, Billerica, Mass. USA). For the OGTT, after the measurement of the basal glucose concentration (T=−30 min), mice received an oral glucose challenge at 2 g/kg and glucose values were determined by glucometer at 0, 15, 30, 60, 90 and 120 min.

Figure 6A:
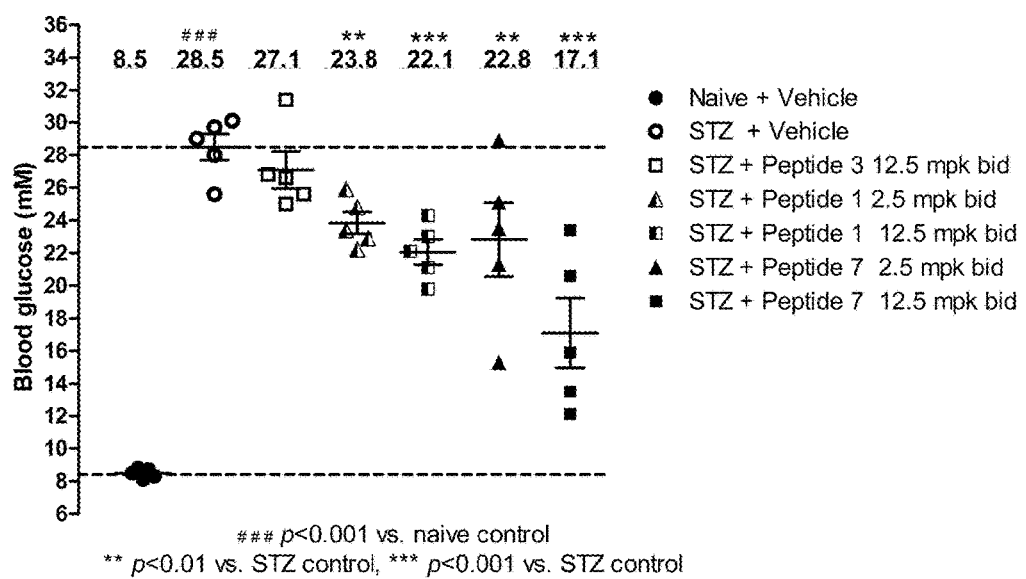
FIGS. 6A-6C show the efficacy comparison of INGAP-PP (Peptide 1), INGAP Scrambled PP 1 (Peptide 3) and a selected peptide analog, Peptide 7 (see Table 2) in STZ induced diabetic mice model.
Figure 6B:
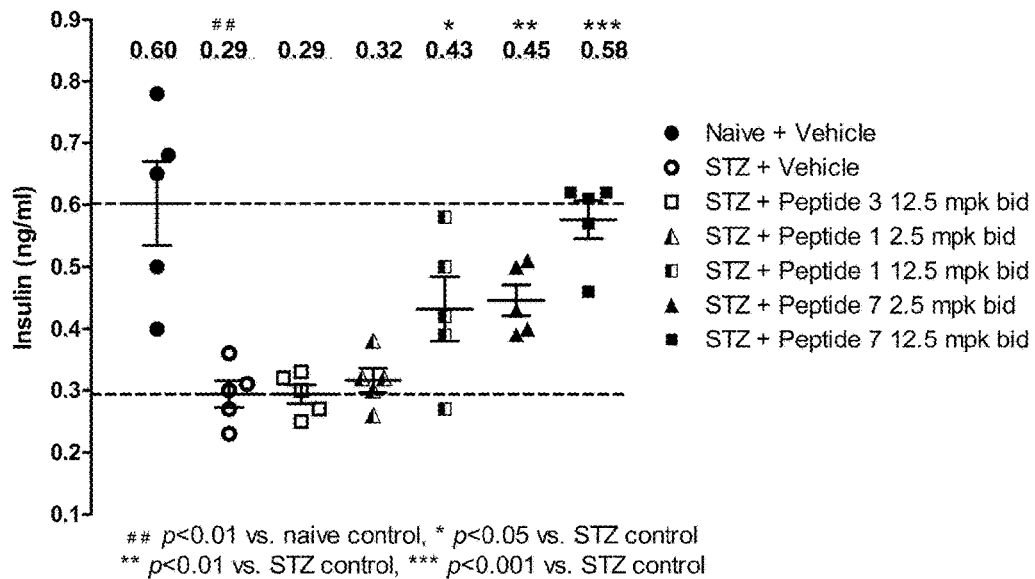
Figure 6C:
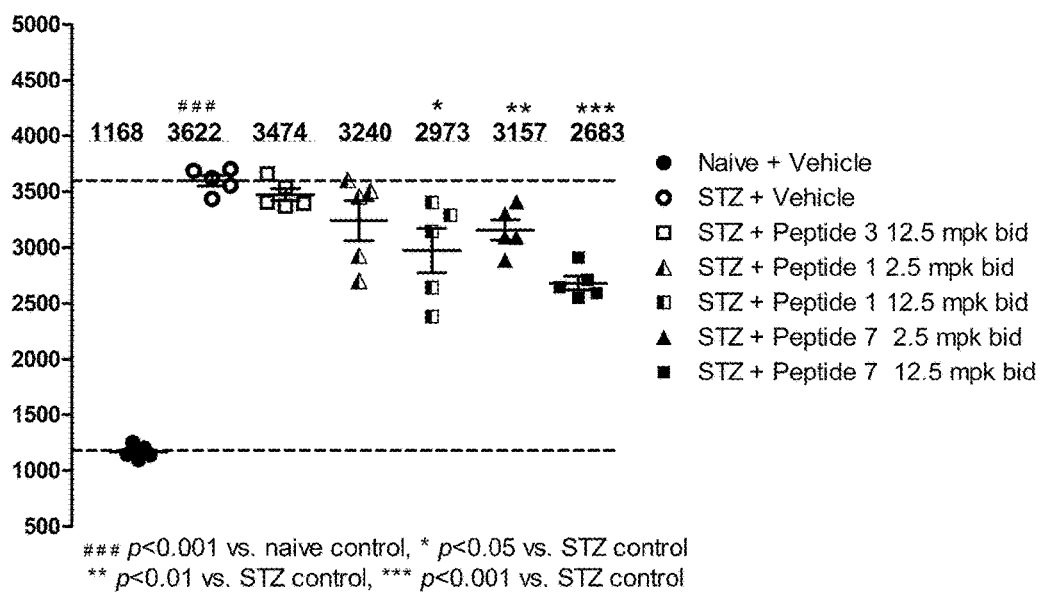

FIG. 6 shows the efficacy comparison of INGAP-PP (Peptide 1), INGAP Scrambled PP 1 (Peptide 3) and Peptide 7 in STZ induced diabetic mice model. FIG. 6A shows the blood glucose (BG, mM) on day 21 of treatment. FIG. 6B shows the fasting insulin levels (ng/ml) on day 21 of treatment. FIG. 6C shows the area under curve (AUC) of glucose ($T_{0-120\ min}$) measured in an oral glucose tolerance test (OGTT) on day 21 of treatment.

Administration of Peptide 1 and Peptide 7 (either 5 mg/kg or 25 mg/kg) for 20 days did not affect body weight or pancreas weight. Significant differences in blood glucose levels were demonstrated between the mouse group administered Peptide 7 and the saline control group (FIG. 6A). Moreover, one of the most striking results was that plasma insulin levels of the Peptide 7 treated animals (25 mg/kg dose group) at the end of the 20-day period were significantly different from saline controls and almost restored to the level of the naive group (FIG. 6B). In addition, the Peptide 7 treated groups also demonstrated improved glucose tolerance (FIG. 6C).

These results demonstrate that a representative peptide analog, peptide 7, was effective at ameliorating signs and symptoms of diabetes in a diabetic mouse model.

EXAMPLE V

The Effect of Peptides on Induction of Small β-Cell Clusters

This example describes the effects of peptides on the induction of small β-cell clusters in normal C57BL/6J mice.

After a 1-week acclimation, C57BL/6J female mice were randomly divided into 4 groups. The two control groups received either 10 mL/kg sterile normal saline (n=4) or scrambled peptide (Peptide 3, 25 mg/kg) (n=5) via subcutaneous injection for 10 days. The other two groups received INGAP-PP (Peptide 1) or INGAP-PP analog Peptide 7 at a dose of 25 mg/kg per day respectively (n=7 per group) for the same period. Body weight and 6 hour fasting blood glucose were measured before treatment and after the last dosing of treatment. Plasma and pancreatic insulin were also measured at the end of the study. On day 11, the pancreas was removed from each animal, cleared of fat and lymph nodes, weighed, and fixed in 10% neutral buffered formalin (NBF) for no longer than 24 hours before processing for morphometric analysis.

Figure 7:
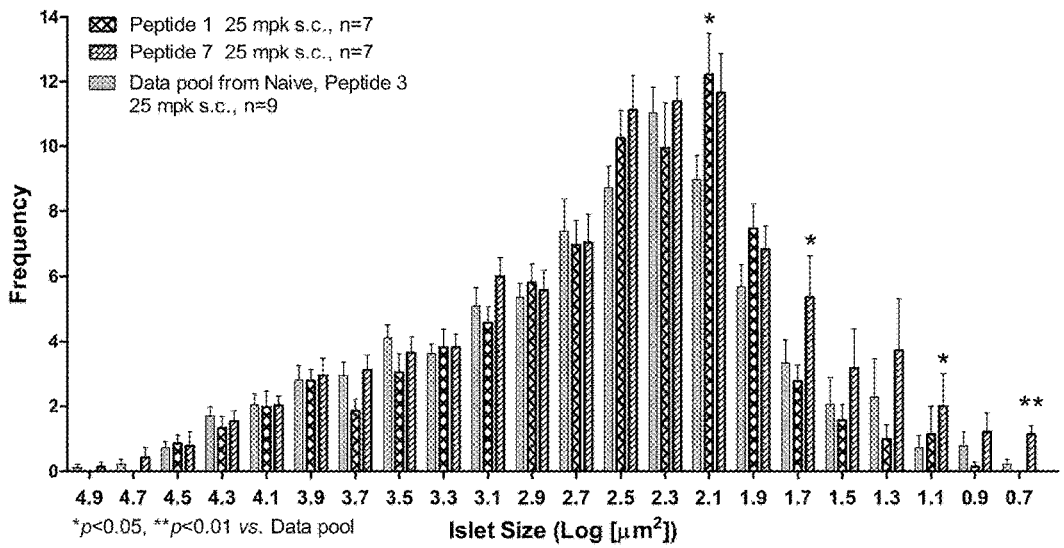
FIG. 7 shows the number of islets defined by area ranges (arbitrary morphometric units) for equal randomly selected fields (n≥7) for animals treated with naive and Peptide 3, Peptide 1 or Peptide 7.

Compared to the saline group, administration of Peptide 3, Peptide 1, or Peptide 7 to normal mice for 10 days did not affect body weight, blood glucose, plasma insulin, pancreas insulin, or pancreas weight. Immunohistochemistry analysis was used to determine pancreatic islet size distribution. FIG. 7 shows pancreatic islet size distribution in female C57BL/6J mice at 10 days of peptide treatment. For the islet size (expressed as Log [$\mu m^2$]) ranging from 4.9 to 2.3, there was no difference for each group, whereas for the islet size ranging from 2.1 to 0.7, the numbers increased significantly in the mice treated with Peptide 7 ($p<0.05$ or $0.01$ versus the naive/control group)(Figure 7). The increase in the Peptide 1 treated mice was only observed in islet size of 2.1 ($p<0.05$ versus the naive/control group).

These results indicated the improved islet neogenic effect of designed INGAP-PP analogs. It is of note that among all parameters measured, there was no difference for mice treated with normal saline or scrambled peptide.

EXAMPLE VI

The Effect of Peptides on Glucose-Stimulated Insulin Secretion

This example describes the effect of peptides on glucose-stimulated insulin secretion (GSIS).

The pancreases were procured from male adult Sprague-Dawley (SD) rats. After 7 days acclimation, the animals were sacrificed by cervical dislocation and the entire pancreas was removed and digested with collagenase to isolate islets. After digestion, islets were maintained at 37° C. in RPMI 1640 (Carlsbad Calif., USA) pH 7.4, containing 10% (v/v) fetal calf serum, 1% penicillin/streptomycin, and 10 mM glucose in a humid atmosphere (5% $CO_2$/95% $O_2$), without the addition of any compound (control), or with the addition of 100 nM glucagon like peptide-1 (GLP-1); or 10 μm/mL Peptide 1, Peptide 12, or Peptide 16, as summarized in Table 4 below.

TABLE 4

| | Parameters for Various Groups Tested for Glucose-stimulated Insulin Secretion (GSIS) | | | | | |
|---|---|---|---|---|---|---|
| | 1 | 2 | 3 | 4 | 5 | 6 |
| A | 1.5 mM Glucose | 12 mM Glucose | 12 mM Glucose; 100 nM GLP-1 | 12 mM Glucose; 10 μg/ml Peptide 1 | 12 mM Glucose; 10 μg/ml Peptide 12 | 12 mM Glucose; 10 μg/ml Peptide 16 |
| B | 1.5 mM Glucose | 12 mM Glucose | 12 mM Glucose; 100 nM GLP-1 | 12 mM Glucose; 10 μg/ml Peptide 1 | 12 mM Glucose; 10 μg/ml Peptide 12 | 12 mM Glucose; 10 μg/ml Peptide 16 |
| C | 1.5 mM Glucose | 12 mM Glucose | 12 mM Glucose; 100 nM GLP-1 | 12 mM Glucose; 10 μg/ml Peptide 1 | 12 mM Glucose; 10 μg/ml Peptide 12 | 12 mM Glucose; 10 μg/ml Peptide 16 |
| D | 1.5 mM Glucose | 12 mM Glucose | 12 mM Glucose; 100 nM GLP-1 | 12 mM Glucose; 10 μg/ml Peptide 1 | 12 mM Glucose; 10 μg/ml Peptide 12 | 12 mM Glucose; 10 μg/ml Peptide 16 |

Cultured islets were rinsed in Krebs-Ringer bicarbonate buffer (KRB), pH 7.4, previously gassed with a mixture of $CO_2/O_2$ (5/95%), and pre-incubated in 1.0 ml of KRB containing 0.5% (w/v) BSA and 1.5 mM glucose at 37° C. for 45 min. After this period, groups of 5 islets were incubated in 0.6 ml KRB with the addition of 1.5 or 12.0 mM glucose, with or without the addition of peptides for 60 min. At the end of the incubation period, aliquots of the medium were collected for insulin quantitation.

Figure 8:
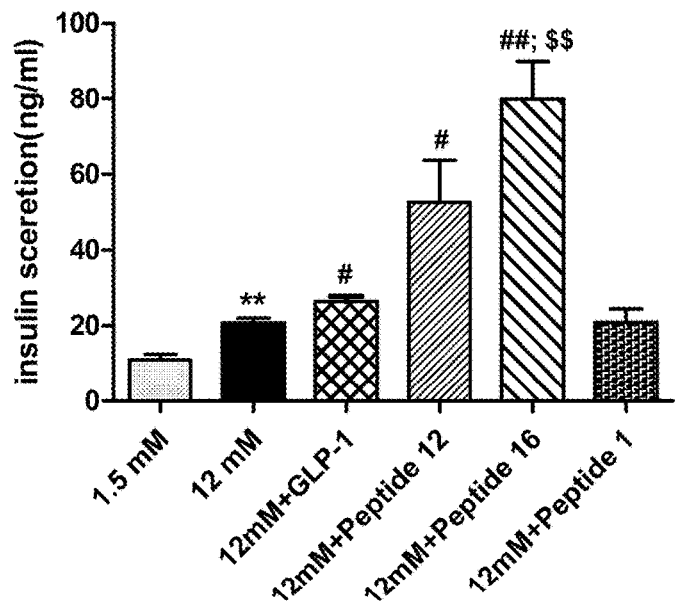
FIG. 8 shows the increase of glucose-stimulated insulin secretion of islets with or without the co-incubation of selected peptides (10 μg/mL), Peptide 12, Peptide 16 and Peptide 1 (see Table 2). Co-incubation with 100 nM Glucagon like peptide—1 (GLP-1) was included as a positive control.

The results of the insulin quantitation are shown in FIG. 8. FIG. 8 shows the increase of glucose-stimulated insulin secretion of islets with or without the co-incubation of selected peptides (10 μg/mL), Peptide 12, Peptide 16 and Peptide 1. Co-incubation with 100 nM Glucagon like peptide-1 (GLP-1) was included as a positive control. At 12.0 mM glucose concentration, pancreatic islets cultured with peptides GLP-1, Peptide 12 and Peptide 16 released significantly more insulin than those cultured without the addition of peptides. In particular, INGAP-PP analogs Peptide 12 and Peptide 16 showed 2-3 fold higher stimulation of insulin secretion than GLP-1. In contrast, no stimulation was observed with the addition of INGAP-PP (Peptide 1) (FIG. 8).

These results demonstrate that INGAP-PP analogs stimulated insulin secretion from pancreatic islet cells.

EXAMPLE VII

Pharmacokinetic Properties of Peptides in Rat and Mouse

This example describes in vivo pharmacokinetic (PK) properties of peptides in rat and mouse.

After 7 days acclimation, male Sprague-Dawley (SD) rats weighing 210-250 g, or male C57BL/6 mice, weighing 19-24 g, in good health were used in the study. Peptide 1, Peptide 12 and Peptide 16 were dissolved in sterile normal saline and then they were injected via subcutaneous (sc) bolus or intravenous (iv) bolus at the dose level of 25 mg/kg. Three animals in each group were used for blood collection at the time point of 5 min, 15 min, 30 min, 1 h, 2 h, 4 h, 6 h, 8 h and 24 h post-dose. Blood samples (approximately 400 μL) were collected and placed into tubes containing EDTA-K2 and centrifuged at 8000 rpm for 6 minutes at 4° C. to separate plasma from the samples. The resulting plasma was stored frozen at −80° C. until being analyzed.

Plasma concentrations of peptides were determined using tandem mass spectrometry (LC-MS/MS) analysis. A non-compartmental module of WinNonlin® Professional 5.2 (Pharsight; St. Louis Mo.), was used to calculate PK parameters. Selected PK parameters are presented in Table 5 below. The abbreviation $AUC_{(0-t)}$ represents area under the curve from the time of dosing to the time of the last observation, the $AUC_{(0-\infty)}$ represents area under the curve from the time of dosing to infinity, and the $C_{max}$ represents maximum concentration detected.

TABLE 5

Pharmacokinetic Parameters in Treated Mice and Rats

| | \multicolumn{9}{c}{Study} | | | | | | | | |
|---|---|---|---|---|---|---|---|---|---|
| | MOUSE (SC) | | | RAT (SC) | | | RAT (IV) | | |
| Parameters | $AUC_{(0-t)}$ μg/L * hr | $AUC_{(0-\infty)}$ μg/L * hr | $C_{max}$ μg/L | $AUC_{(0-t)}$ μg/L * hr | $AUC_{(0-\infty)}$ μg/L * hr | $C_{max}$ μg/L | $AUC_{(0-t)}$ μg/L * hr | $AUC_{(0-\infty)}$ μg/L * hr | $C_{max}$ μg/L |
| Peptide 1 | 54.5 | 58.3 | 140.9 | 298.5 | 305.1 | 1238.0 | 21.9 | 27.1 | 48.7 |
| Peptide 12 | 5873.1 | 5888.2 | 11600.7 | 8423.3 | 8480.0 | 14024.2 | 12632.5 | 12633.8 | 44312.7 |
| Peptide 16 | 11350.6 | 11354.4 | 14376.4 | 12127.1 | 12202.7 | 18907.7 | 12191.6 | 12192.7 | 45194.9 |

Compared to INGAP-PP (Peptide 1), the peptide analogs Peptide 12 and Peptide 16 showed marked improved PK properties evidenced by the significant increase in the area under the plasma concentration-time curves (AUC) and the maximum concentration (Cmax) in mouse and rat.

These results demonstrate that the INGAP-PP peptide analogs exhibited significantly improved pharmacokinetic properties over INGAP-PP.

EXAMPLE VIII

Effect of Peptides on Induction of Extra Islet Insulin Positive β Cell Clusters

This example describes the effects of peptides on the induction of extra islet insulin positive β cell clusters in normal C57BL/6J mice.

After a 1-week acclimation, female C57BL/6J mice were randomly divided into 6 groups (n=5 per group). The control group received 10 mL/kg sterile normal saline via subcutaneous injection for 10 consecutive days. The other five groups received INGAP-PP (Peptide 1) or INGAP-PP analogs Peptide 12, Peptide 16, Peptide 29 or Peptide 31 at a dose of 50 mg/kg or 5 mg/kg per day, respectively, for the same period. On day 11, the pancreas was removed from each animal, cleared of fat and lymph nodes, weighed, and fixed in 10% neutral buffered formalin (NBF) for no longer than 24 hours before processing for morphometric analysis.

Immunohistochemistry analysis was used to assess the islet neogenic activities of peptides by measuring the number and area of extra islet insulin positive β cell clusters (EIC) of pancreatic tissues harvested from each individual group post 10 day treatment. EIC is indicative of islet neogenesis, as previously described by Lipsett and Finegood (*Diabetes* 51:1834-1841 (2002)).

Figure 9A:
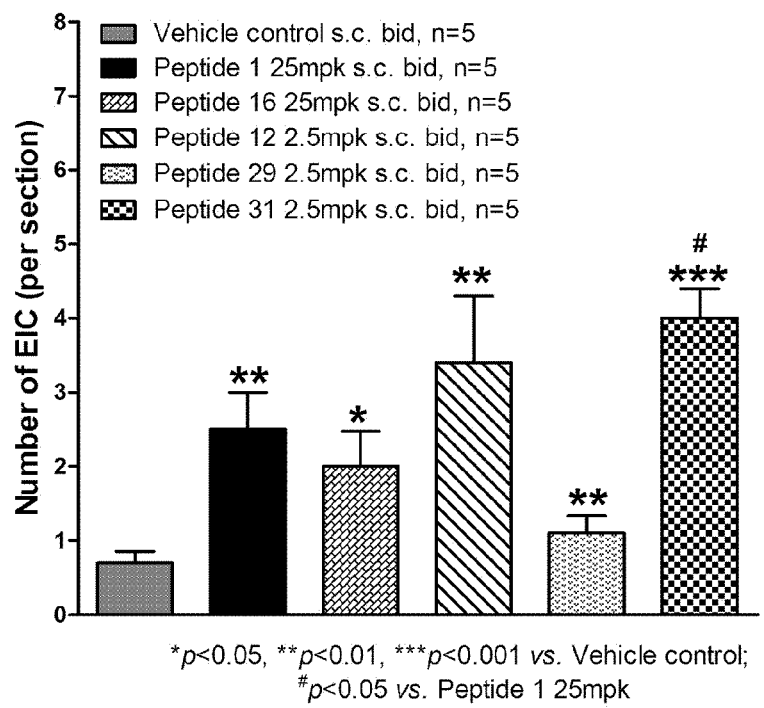
FIGS. 9A-9C show the biological effect of administering INGAP-PP or INGAP-PP analogs.
Figure 9B:
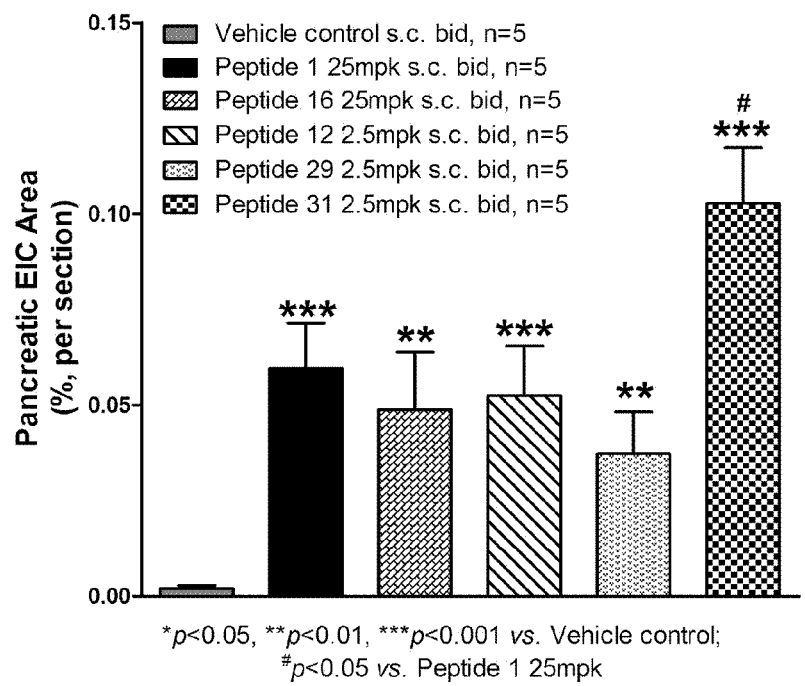
Figure 9C:
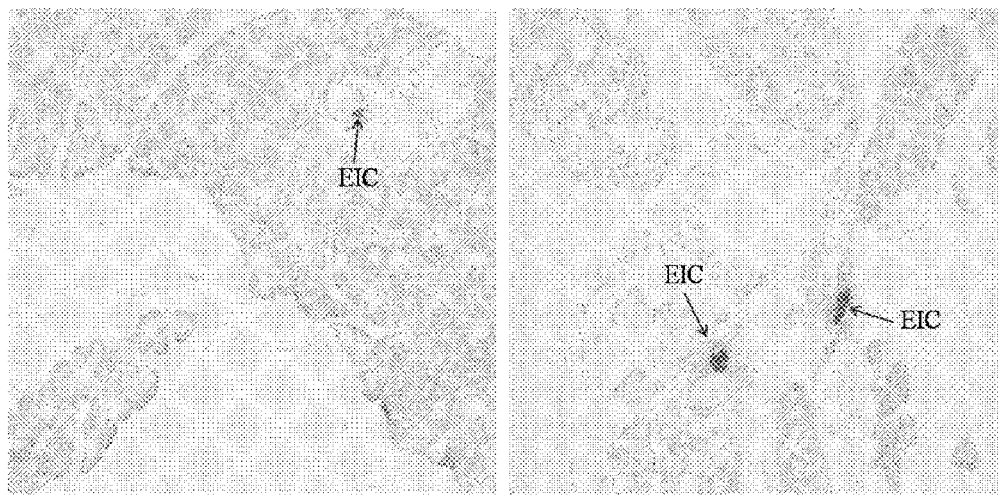

Comparing to the saline treated group, there was a significant increase of number and area of EIC in peptide treated groups. FIG. 9A shows the number of EIC in female C57BL/6J mice after 10 days of treatment. FIG. 9B shows the total area of EIC in female C57BL/6J mice after 10 days of treatment. FIG. 9C shows representative ductal associated EIC in pancreas after administration of INGAP-PP peptide or INGAP-PP analog. The INGAP-PP or INGAP-PP analog treated groups exhibited a significant increase in the EIC number and EIC area compared with saline treated group. Noteworthy is that the EIC number and area in Peptide 31 (5 mg/kg) treated group are statistically greater than that of INGAP-PP (Peptide 1) (50 mg/kg) treated group (p<0.05).

The results demonstrated the biological activities of INGAP-PP and its analogs in stimulating the islet neogenesis in normal mice after 10 days treatment. Importantly, for Peptide 12 or Peptide 31 treated groups, comparable or improved efficacy was achieved at a dose one tenth of INGAP-PP, indicating improved potency of INGAP-PP analogs.

EXAMPLE IX

Effect of Peptides on Islet Neogenesis Reflected by Pancreatic Islet Size Distribution This example describes the islet neogenesis effects of peptides reflected by pancreatic islet size distribution in normal C57BL/6J mice.

After a 1-week acclimation, female C57BL/6J mice were randomly divided into 4 groups (n=6 per group). The control group received 10 mL/kg sterile normal saline via subcutaneous injection for 10 consecutive days. The other three groups received INGAP-PP (Peptide 1) at the dose of 25 mg/kg/day or INGAP-PP analog Peptide 12 or Peptide 31 at the dose of 0.25 mg/kg/day, respectively, for the same period. Different doses of INGAP-PP or INGAP-PP analogs were used in the study based on efficacious dose of INGAP-PP known in the art and the pharmacokinetic properties characterizations of INGAP-PP analogs. On day 11, the pancreas was removed from each animal, cleared of fat and lymph nodes, and fixed in 10% neutral buffered formalin (NBF) for no longer than 24 hours before processing for immunohistochemistry analysis. Insulin stained positive sections were traced and quantitated using image analysis software (Olympus DP70 microscope connected by video camera to a computer equipped with Image-Pro Plus software version 6.0), and the islet size distribution analysis was carried out.

Figure 10:
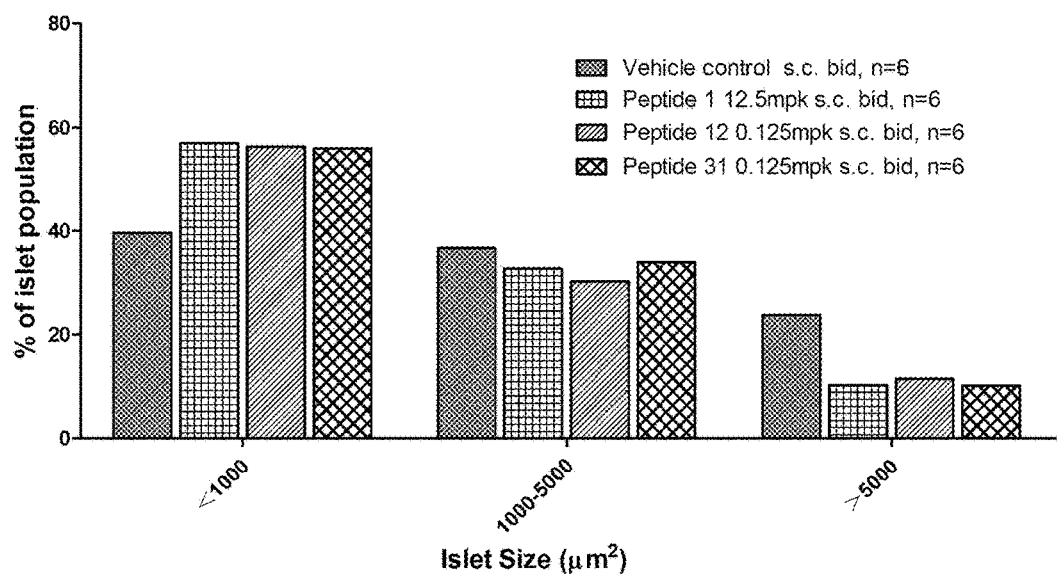
FIG. 10 shows the effect of INGAP-PP peptide and INGAP-PP analogs on islet neogenesis as reflected by pancreatic islet size distribution.

Compared to the saline treated groups, mice treated with INGAP-PP or INGAP-PP analogs for 10 days showed a shift towards to small islet size showed in FIG. 10. In particular, there is about 50% of increase for islet size smaller than 1000 μm$^2$ in peptide treated groups (60% of islet population in peptide treated group versus 40% in saline group), whereas no difference for islet size between 1000 and 5000 μm², and about 50% of decrease for islet size greater than 5000 μm² (about 10% of islet population in peptide treated group versus 20% in saline group).

These results show that INGAP-PP and INGAP-PP analogs exhibited a shift towards small islet size. In addition, the INGAP-PP analogs tested exhibited the activity at 1/100 the dosage of INGAP-PP.

EXAMPLE X

Pharmacokinetics Properties of Peptides in SD Rats

This example describes in vivo pharmacokinetic (PK) properties of peptides after a single subcutaneous (sc) administration to SD rat.

After 7 days acclimation, a total of 15 male Sprague-Dawley (SD) rats (body weight: 230 to 270 g) in good health from Sino-British SIPPR/BK Lab Animal Ltd, Shanghai, were used in the study. All peptides, Peptide 1, Peptide 12, Peptide 16, Peptide 29 or Peptide 31, were dissolved in sterile normal saline respectively to yield the desired final concentrations and were administered via single subcutaneous (sc) dose. Detailed information for the pharmacokinetic studies is presented in Table 6.

TABLE 6

Group and Dosing Information for Pharmacokinetic (PK) Studies

| Group Number | Sex | Number of Animals | Test Article | Dose Level (mg/kg) |
|---|---|---|---|---|
| 1 | Male | 3 | Peptide 1 | 25 |
| 2 | Male | 3 | Peptide 12 | 25 |
| 3 | Male | 3 | Peptide 16 | 25 |
| 4 | Male | 3 | Peptide 29 | 25 |
| 5 | Male | 3 | Peptide 31 | 25 |

Three animals in each group were used for blood collection at the time point of 5 min, 15 min, 30 min, 1 h, 2 h, 4 h, 6 h, 8 h and 24 h post-dose. Blood samples (approximately 400 μL) were collected and placed into tubes containing EDTA-K2 (dipotassium ethylene diamine tetraacetic acid) and centrifuged at 8000 rpm for 6 minutes at 4° C. to separate plasma from the samples. The resulting plasma was stored frozen at −80° C. until being analyzed.

Plasma concentrations of peptides were determined using tandem mass spectrometry (LC-MS/MS) analysis. A non-compartmental module of WinNonlin® Professional 5.2 (Pharsight; St. Louis Mo.) was used to calculate PK parameters. Selected PK parameters are presented in Table 7 below. $AUC_{(0-t)}$ represents area under the curve from the time of dosing to the time of the last observation, the $AUC_{(0-\infty)}$ represents area under the curve from the time of dosing to infinity, and the $C_{max}$ represents maximum concentration detected.

TABLE 7

Selected Pharmacokinetic Parameters in in Sprague-Dawley Rat Following Subcutaneous Administration

| Testing Peptide | Sex Male/Female | Dose Level mg/kg | $AUC_{(0-t)}$ μg/L*hr | $AUC_{(0-\infty)}$ μg/L*hr | $C_{max}$ μg/L |
|---|---|---|---|---|---|
| Peptide 1 | Male | 25 | 294.13 ± 124.80 | 297.86 ± 122.41 | 1188.86 ± 609.56 |
| Peptide 12 | Male | 25 | 11063.21 ± 1366.62 | 11160.28 ± 1211.17 | 21363.99 ± 1354.43 |
| Peptide 16 | Male | 25 | 11177.17 ± 1884.33 | 11179.40 ± 1883.66 | 22055.34 ± 5872.06 |
| Peptide 29 | Male | 25 | 14432.93 ± 1005.09 | 14435.76 ± 1003.61 | 16285.43 ± 2522.07 |
| Peptide 31 | Male | 25 | 15562.38 ± 1529.00 | 15563.32 ± 1528.94 | 25975.89 ± 3098.76 |

Compared to INGAP-PP (Peptide 1), the analogs Peptide 12, Peptide 16, Peptide 29 and Peptide 31 showed improved PK properties as evidenced by the significant increase in AUC and $C_{max}$ in SD rat with the same sex and at the same dose level.

To further characterize the pharmacokinetic (PK) properties of peptides, peptide concentration in pancreas—the target organ, was determined 30 min post dose. Briefly, INGAP-PP (Peptide 1), Peptide 12, or Peptide 31 was dissolved in sterile normal saline and then was administered via subcutaneous (sc) bolus at the dose level of 25 mg/kg to male Sprague-Dawley (SD) rats. Five animals in each group were used for blood and pancreas collection at the time point of 30 min post-dose. Blood samples (approximately 400 μL) were collected and placed into tubes containing EDTA-K2 and centrifuged at 8000 rpm for 6 minutes at 4° C. to separate plasma from the samples. After blood extraction and animal sacrifice, the pancreas was removed immediately from each animal, cleared of fat and lymph nodes, weighed, and placed into 5 fold volume of ice cold sterile normal saline with protease inhibitor cocktail (Merck Millipore, catalogue #539137) to homogenize with a homogenizer.

The peptide concentration of the plasma and pancreatic homogenate was determined immediately using tandem mass spectrometry (LC-MS/MS) analysis and the results are presented in Table 8.

TABLE 8

Peptide Concentration in Plasma and Pancreas

| Sample Type | Peptide concentration (ng/mL) | | |
|---|---|---|---|
| | Peptide 1 | Peptide 12 | Peptide 31 |
| Plasma | 209.81 ± 107.08 | 5374.81 ± 980.67 | 15356.49 ± 3516.52 |
| Pancreas | NA | 877.22 ± 261.07 | 1633.48 ± 339.93 |

NA: Below the lower limit of quantitation (LLOQ) 2.5 ng/mL

Compared to INGAP-PP (Peptide 1), the peptide analogs Peptide 12 and Peptide 31 showed improved PK properties evidenced by the significant increase in the plasma and pancreas concentration.

These results demonstrated that compared to INGAP-PP, the INGAP-PP peptide analogs exhibited significantly improved in vivo pharmacokinetic properties.

EXAMPLE XI

Peptide Stability Studies

This example describes stability studies of peptides in various conditions.

To determine the stability of peptides in culture medium, a certain amount of selected peptides was accurately weighed and dissolved in distilled water to 5 mg/mL as a stock solution. The stock solution was diluted to 0.25 mg/mL with F-12K medium (Gibco-BRL, Gaithersburg, Md., USA) as working solution. A volume of 100 µL of each working solution was transferred into individual sample vials. The sample vials were incubated in a 37° C. incubator for 0, 24, 48 and 72 hours before being analyzed and quantitated by HPLC.

Figure 11:
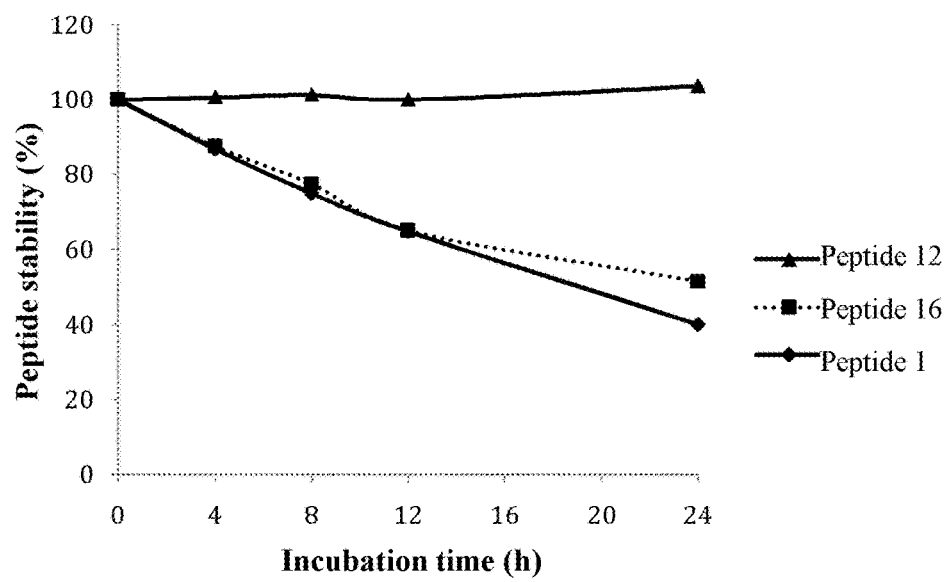
FIG. 11 shows the stability of INGAP-PP and INGAP-PP analogs in culture medium.

FIG. 11 shows the stability of compounds in culture medium. In particular, FIG. 11 shows a stability comparison in culture medium of INGAP-PP (Peptide 1) and selected peptide analogs, Peptide 12 and Peptide 16. As shown in FIG. 11, peptide analogs Peptide 12 and Peptide 16 were significantly more stable than INGAP-PP peptide in culture medium.

The stability of peptides was also tested in rat, mouse and human plasma. Briefly, a certain amount of peptides and eucatropine powder (positive control) was accurately weighed. Test compounds were dissolved in 50% methanol-water solution and diluted to 20 mg/mL, and eucatropine was dissolved in dimethylsulfoxide (DMSO) and diluted to 10 mM, as a stock solution. Eucatropine stock solution was diluted to 0.2 mM with DMSO as a working solution. A stop reagent was prepared containing 200 ng/mL midazolam and tolbutamide in acetonitrile. A volume of 300 µL of stop solution was added to each well of a 96-well deep-well plate placed on ice beforehand.

For the stability studies, peptides and eucatropine were spiked into plasma respectively, mixed well, and then 100 µL of each mixture solution was transferred into the pre-cooled stop reagent as 0 time point sample. The remaining mixtures were incubated in a 37° C. water bath with shaking at 100 rpm (n=2). The final incubation concentration was 1 µM for eucatropine and 100 µg/mL for all test compounds.

At desired time points, 100 µL of incubation mixture was transferred to the stop reagent to precipitate proteins. Samples were vortexed and centrifuged at RCF 5000×g for 10 minutes, and supernatant was transferred to a test plate. The samples were analyzed by LC-MS/MS.

Slope was calculated by plotting the natural logarithm of the percentage of remaining amount of test compounds and time, and $T_{1/2}$ was calculated in accordance with the following formula.

$$T_{1/2} = \frac{0.693}{-\text{slope}}$$

Figure 12:
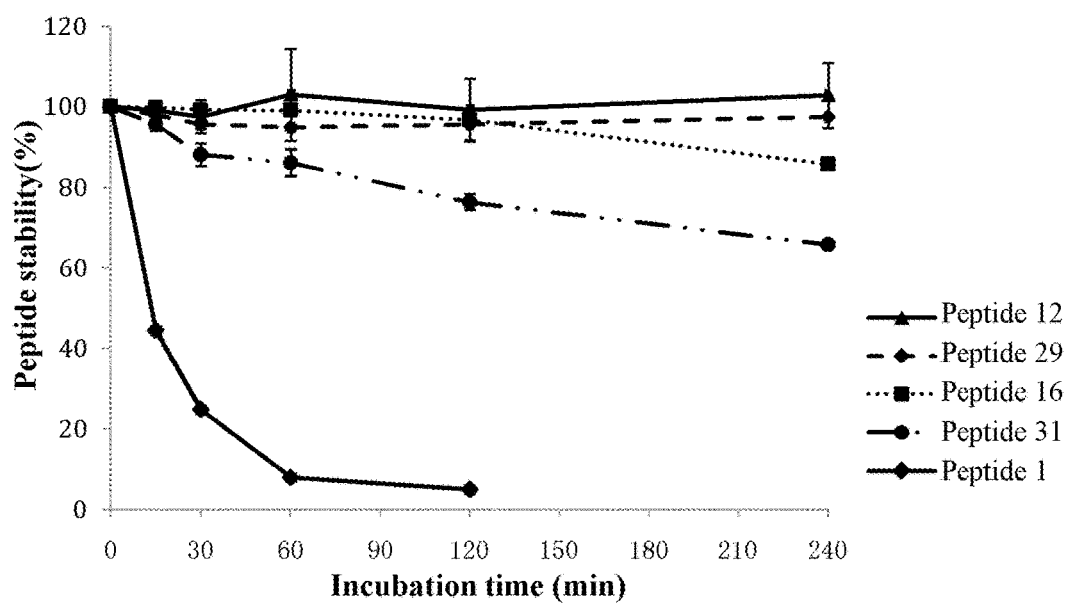
FIG. 12 shows the stability of INGAP-PP and INGAP-PP analogs in rat plasma.

For stability in rat plasma, the incubation time was 0, 15, 30, 60 and 120 min for Peptide 1 and eucatropine, and 0, 15, 30, 60, 120, and 240 min for Peptide 12, Peptide 16, Peptide 29 and Peptide 31. FIG. 12 shows stability of compounds in rat plasma. In particular, FIG. 12 shows a stability comparison in rat plasma of INGAP-PP (Peptide 1) and selected peptide analogs, Peptide 12, Peptide 16, Peptide 29 and Peptide 31. As shown in FIG. 12, peptide analogs Peptide 12, Peptide 16, Peptide 29 and Peptide 31 exhibited good stability in rat plasma and were more stable than INGAP-PP (Peptide 1).

Figure 13:
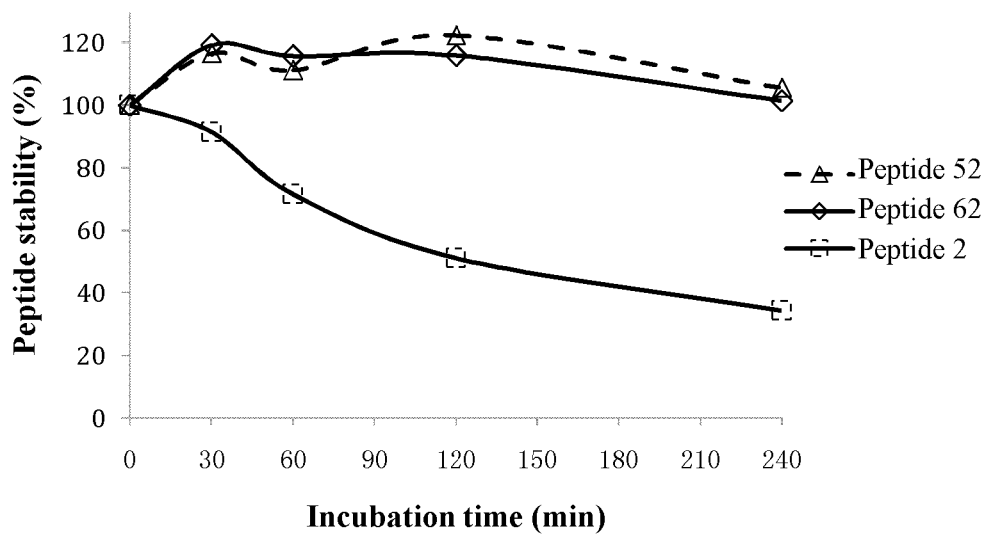
FIG. 13 shows the stability of HIP and HIP analogs in rat plasma.

In another stability study in rat plasma, the incubation time was 0, 30, 60 120 and 240 min for Peptide 2, Peptide 52, Peptide 64 and eucatropine. FIG. 13 shows stability of compounds in rat plasma. In particular, FIG. 13 shows a stability comparison in rat plasma of HIP (Peptide 2) and selected peptide analogs, Peptide 52 and Peptide 62. As shown in FIG. 13, peptide analogs Peptide 52 and Peptide 62 exhibited good stability in rat plasma and were significantly more stable than HIP (Peptide 2).

Figure 14:
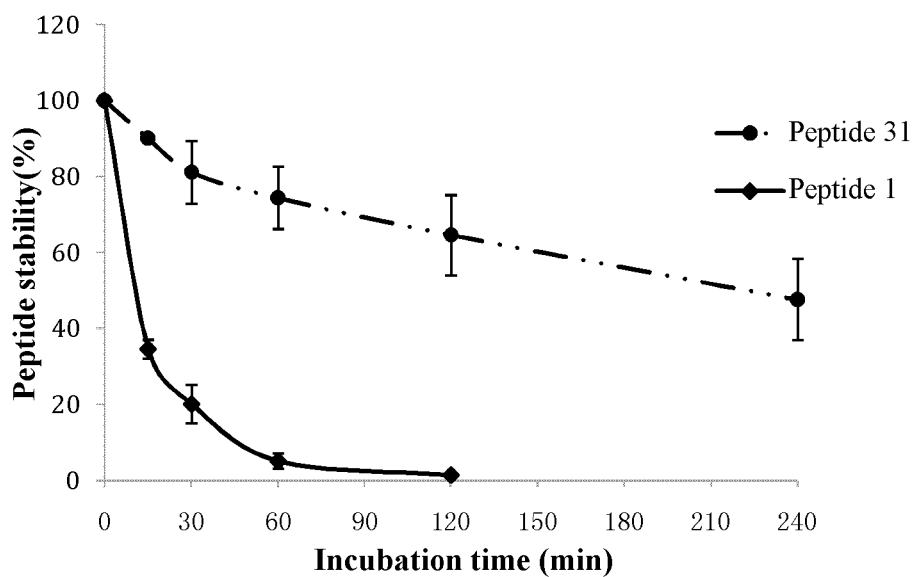
FIG. 14 shows the stability of INGAP-PP and INGAP-PP analog in mouse plasma.

For stability in mouse plasma, the incubation time was 0, 15, 30, 60 and 120 min for Peptide 1 and eucatropine; 0, 15, 30, 60, 120, and 240 min for Peptide 31. FIG. 14 shows stability of compounds in mouse plasma. In particular, FIG. 14 shows a stability comparison in mouse plasma of INGAP-PP (Peptide 1) and Peptide 31. As shown in FIG. 14, Peptide 31 exhibited good stability in mouse plasma and was more stable than INGAP-PP (Peptide 1).

Figure 15:
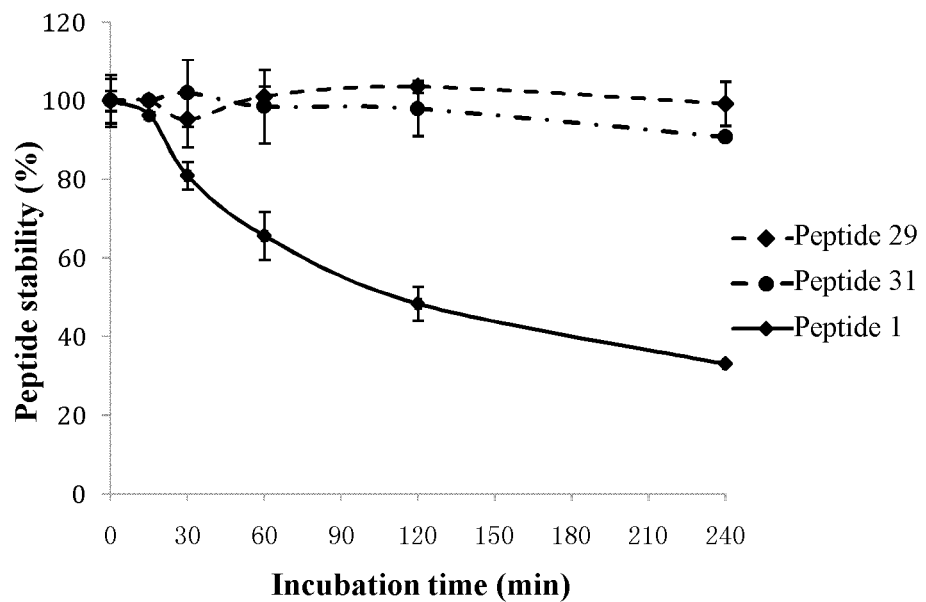
FIG. 15 shows the stability of INGAP-PP and INGAP-PP analogs in human plasma.

For stability in human plasma, the incubation time was 0, 15, 30, 60, 120 and 240 min for Peptide 1, Peptide 29, Peptide 31 and eucatropine. FIG. 15 shows the stability of compounds in human plasma. In particular, FIG. 15 shows a stability comparison in human plasma of INGAP-PP (Peptide 1) and selected peptide analogs, Peptide 29 and Peptide 31. As shown in FIG. 15, peptide analogs Peptide 29 and Peptide 31 exhibited good stability in human plasma and were significantly more stable than INGAP-PP (Peptide 1).

Peptide stability in buffers was tested for INGAP-PP and selected analogs. 10 mg/mL of Peptide 1, Peptide 12, Peptide 16, Peptide 29 or Peptide 31 was dissolved in isotonic buffers with pH ranging from 4.0 to 8.0. Similar to Peptide 1, Peptide 16 and Peptide 31 were found to be more stable in buffers with pH from 4.0 to 6.0, whereas Peptide 12 and Peptide 29 were more stable in buffers with pH from 6.0 to 8.0. A further study to evaluate the peptide stability in buffers found that Peptide 16 and Peptide 31 were stable in an isotonic acetate buffer (pH 5.0) for up to 90 days at 4° C., and less than 7 days at 25° C. Peptide 12 and Peptide 29 were stable in an isotonic phosphate buffer (pH 7.4) for more than 90 days at 4° C. (there was no sign of degradation at 90 days sample check point), and 60 days at 25° C.

These results demonstrate that various peptide analogs exhibit good stability under various conditions, including culture medium, rat, mouse and human plasma, and exhibit superior stability over INGAP-PP and HIP peptides.

EXAMPLE XII

Sustained Release Systems for Long-Acting Delivery

This example describes the usage of various biocompatible and biodegradable materials to develop sustained release systems of INGAP-PP and analogs for clinical applications of INGAP-PP and analogs.

Figure 16:
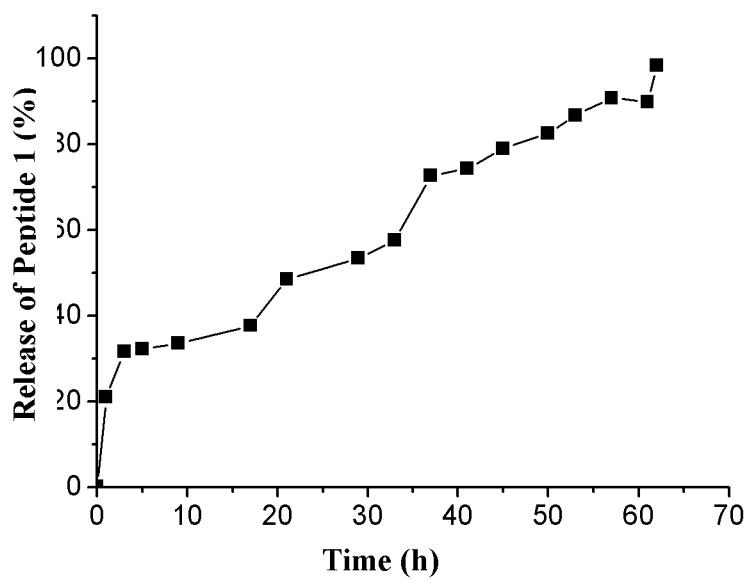
FIG. 16 shows a representative in vitro INGAP-PP (Peptide 1) release curve of hydrogel containing Pluronic F127.
Figure 17:
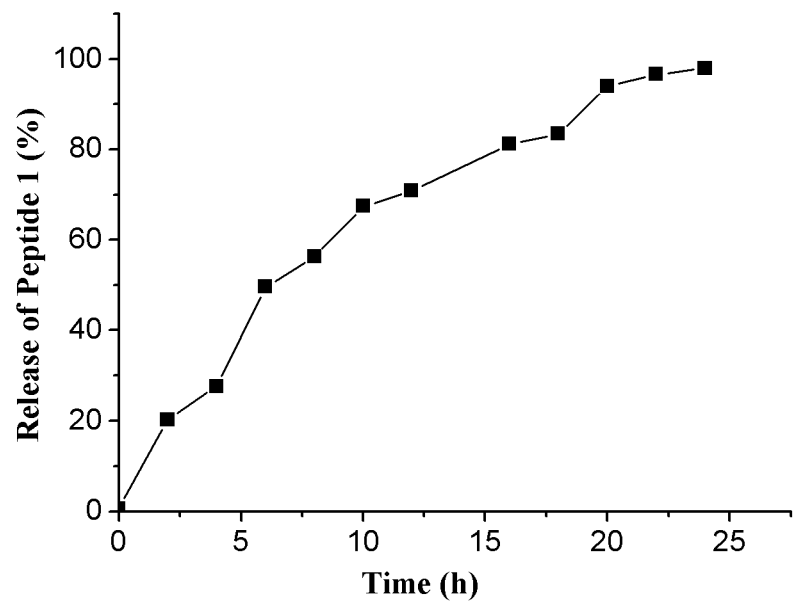
FIG. 17 shows a representative in vitro INGAP-PP (Peptide 1) release curve of hydrogel containing Jeffamine ED-2003.

Biocompatible polymer containing poly (ethylene glycol) (PEG) segment at a concentration of 0.5% w/w to 20% w/w of the final weight of the composition, α-cyclodextrin at a concentration of 5% w/w to 15% w/w of the final weight of the composition, INGAP-PP and/or its analogs at a concentration of 0.1% w/w to 20% w/w of the final weight of the composition and phosphate buffer saline (PBS) was evaluated. Biocompatible polymer containing PEG segment, for example, Pluronic F127, Pluronic F38, Pluronic F68, Pluronic F87, Pluronic F 108, Jeffamine ED-2003, and analogue can also be incorporated to form the supramolecular hydrogel system. The PEG, biocompatible polymer containing PEG segment, and α-cyclodextrin can be dissolved either alone or in a premixed form, INGAP-PP and/or its analogs can be dispersed directly in PBS, then mixed with PEG mixture. The mixed solution is then sonicated to form a hydrogel. FIG. 16 shows a representative in vitro INGAP-PP (Peptide 1) release curve of hydrogel containing Pluronic F127. FIG. 17 shows a representative in vitro INGAP-PP (Peptide 1) release curve of hydrogel containing Jeffamine ED-2003.

Figure 18:
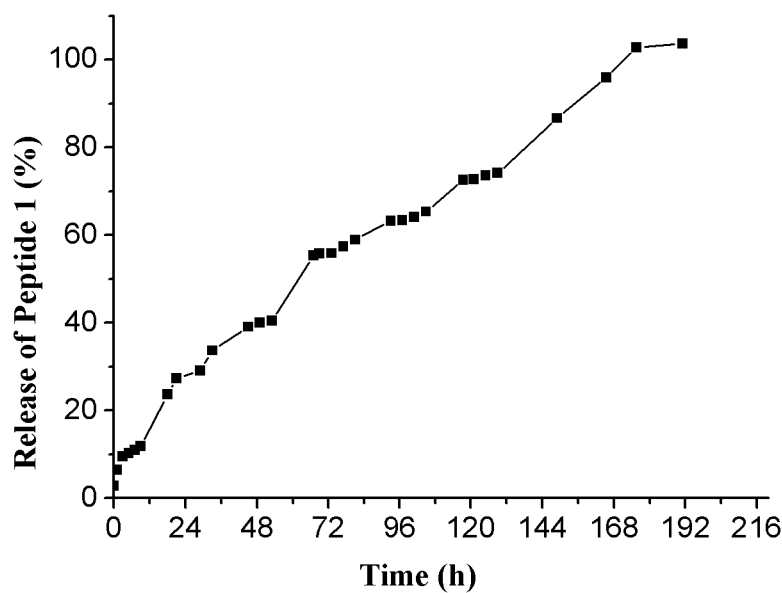
FIG. 18 shows a representative in vitro INGAP-PP (Peptide 1) release curve of SABER gel system.

A sustained release system with the composition of sucrose acetate isobutyrate (SAIB), INGAP-PP and/or its analogs, and a solvent was also evaluated. Useful formulations comprise SAIB at a concentration of 45% w/w to 85% w/w of the final weight of the composition, INGAP-PP and/or its analogs at a concentration of 0.1% w/w to 20% w/w of the final weight of the composition, and the rest is a solvent. The solvent can be selected from ethanol, acetone, ethyl acetate, or any other solvents that can dissolve SAIB. FIG. 18 shows a representative in vitro INGAP-PP (Peptide 1) release curve of SABER gel system.

The sustained release systems described above demonstrated that feasibility of long acting release dosage forms of INGAP-PP or its analogs.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A method for inhibiting inflammation in a subject in need thereof, comprising administering to the subject a composition comprising a peptide comprising an amino acid sequence selected from the group consisting of IGLHDPSHGTLPAG (SEQ ID NO:73) and IGLHDPTQGTEPAG (SEQ ID NO:118), or a peptide analog comprising an amino acid sequence selected from the group consisting of SEQ ID NOs: 10-15, 28-30, 41, 43-45, 47-49, 51-53, 60, 62, 68 and 70-72.

2. The method of claim 1, wherein the peptide or analog thereof further comprises a modification selected from an acetylated N-terminus, an amidated C-terminus, a D amino acid, a non-natural amino acid, a fatty acid modification, esterification, or a combination thereof.

3. The method of claim 1, wherein the peptide or analog thereof has a length of 20 amino acids or less.

4. The method of claim 1, wherein the composition is a pharmaceutical composition further comprising a pharmaceutically acceptable carrier.

5. The method of claim 1, wherein the peptide or analog thereof comprises an amino acid sequence selected from the group consisting of:

| | |
|---|---|
| IGLHDPSHGTLPAGS; | (SEQ ID NO: 7) |
| IGLHDPSHGTLPAGSK; | (SEQ ID NO: 9) |
| IGLHDPSHGTLP(Aib)GS; | (SEQ ID NO: 10) |
| IGLHDPSHGTLP(N-methyl-L-Ala)GS; | (SEQ ID NO: 11) |
| Ac-IGLHDPSHGTLPAGS; | (SEQ ID NO: 12) |
| (D-Ile)GLHDPSHGTLPAGS; | (SEQ ID NO: 13) |
| (L-NorVal)GLHDPSHGTLPAGS; | (SEQ ID NO: 14) |
| (L-NorLeu)GLHDPSHGTLPAGS; | (SEQ ID NO: 15) |
| IGLHDPSHGTLPAGK; | (SEQ ID NO: 23) |
| IGLHDPSHGTLPAGE; | (SEQ ID NO: 27) |
| IGLHDPSHGTLPAG-NH2; | (SEQ ID NO: 28) |
| Ac-IGLHDPSHGTLPAGS-NH2; | (SEQ ID NO: 29) |
| Ac-IGLHDPSHGTLPAG-NH2; | (SEQ ID NO: 30) |
| IGLHDPSHGTLPAGS-NH2; | (SEQ ID NO: 41) |
| IGLHDPSHGTLPAGSC; | (SEQ ID NO: 42) |
| Ac-IGLHDPSHGTLPAGSC; | (SEQ ID NO: 43) |
| IGLHDPSHGTLPAGSC-NH2; | (SEQ ID NO: 44) |
| Ac-IGLHDPSHGTLPAGSC-NH2; | (SEQ ID NO: 45) |
| IGLHDPSHGTLPAGC; | (SEQ ID NO: 46) |
| Ac-IGLHDPSHGTLPAGC; | (SEQ ID NO: 47) |
| IGLHDPSHGTLPAGC-NH2; | (SEQ ID NO: 48) |
| and | |
| Ac-IGLHDPSHGTLPAGC-NH2. | (SEQ ID NO: 49) |

6. The method of claim 5, wherein the peptide or analog thereof further comprises a modification selected from an acetylated N-terminus, an amidated C-terminus, a D amino acid, a non-natural amino acid, a fatty acid modification, esterification, or a combination thereof.

7. The method of claim 5, wherein the peptide or analog thereof has a length of 20 amino acids or less.

8. The method of claim 5, wherein the composition is a pharmaceutical composition further comprising a pharmaceutically acceptable carrier.

9. The method of claim 5, wherein the peptide or analog thereof consists of an amino acid sequence selected from the group consisting of:

| | |
|---|---|
| IGLHDPSHGTLPAGS; | (SEQ ID NO: 7) |
| IGLHDPSHGTLPAGSK; | (SEQ ID NO: 9) |
| IGLHDPSHGTLP(Aib)GS; | (SEQ ID NO: 10) |
| IGLHDPSHGTLP(N-methyl-L-Ala)GS; | (SEQ ID NO: 11) |
| Ac-IGLHDPSHGTLPAGS; | (SEQ ID NO: 12) |
| (D-Ile)GLHDPSHGTLPAGS; | (SEQ ID NO: 13) |
| (L-NorVal)GLHDPSHGTLPAGS; | (SEQ ID NO: 14) |
| (L-NorLeu)GLHDPSHGTLPAGS; | (SEQ ID NO: 15) |
| IGLHDPSHGTLPAGK; | (SEQ ID NO: 23) |
| IGLHDPSHGTLPAGE; | (SEQ ID NO: 27) |
| IGLHDPSHGTLPAG-NH2; | (SEQ ID NO: 28) |
| Ac-IGLHDPSHGTLPAGS-NH2; | (SEQ ID NO: 29) |
| Ac-IGLHDPSHGTLPAG-NH2; | (SEQ ID NO: 30) |
| IGLHDPSHGTLPAGS-NH2; | (SEQ ID NO: 41) |
| IGLHDPSHGTLPAGSC; | (SEQ ID NO: 42) |
| Ac-IGLHDPSHGTLPAGSC; | (SEQ ID NO: 43) |
| IGLHDPSHGTLPAGSC-NH2; | (SEQ ID NO: 44) |
| Ac-IGLHDPSHGTLPAGSC-NH2; | (SEQ ID NO: 45) |
| IGLHDPSHGTLPAGC; | (SEQ ID NO: 46) |
| Ac-IGLHDPSHGTLPAGC; | (SEQ ID NO: 47) |

-continued

| | |
|---|---|
| IGLHDPSHGTLPAGC-NH2; and | (SEQ ID NO: 48) |
| Ac-IGLHDPSHGTLPAGC-NH2. | (SEQ ID NO: 49) |

10. The method of claim 9, wherein the composition is a pharmaceutical composition further comprising a pharmaceutically acceptable carrier.

11. The method of claim 1, wherein the peptide or analog thereof comprises an amino acid sequence selected from the group consisting of:

| | |
|---|---|
| IGLHDPTQGTEPAG; | (SEQ ID NO: 118) |
| IGLHDPTQGTEPAGE; | (SEQ ID NO: 50) |
| IGLHDPTQGTEP(Aib)GE; | (SEQ ID NO: 51) |
| Ac-IGLHDPTQGTEPAGE; | (SEQ ID NO: 52) |
| (D-Ile)GLHDPTQGTEPAGE; | (SEQ ID NO: 53) |
| Ac-IGLHDPTQGTEPAG-NH2; | (SEQ ID NO: 60) |
| Ac-IGLHDPTQGTEPAGE-NH2; | (SEQ ID NO: 62) |
| IGLHDPTQGTEPAGE-NH2; | (SEQ ID NO: 68) |
| IGLHDPTQGTEPAGC; | (SEQ ID NO: 69) |
| Ac-IGLHDPTQGTEPAGC; | (SEQ ID NO: 70) |
| IGLHDPTQGTEPAGC-NH2; and | (SEQ ID NO: 71) |
| Ac-IGLHDPTQGTEPAGC-NH2. | (SEQ ID NO: 72) |

12. The method of claim 11, wherein the peptide or analog thereof further comprises a modification selected from an acetylated N-terminus, an amidated C-terminus, a D amino acid, a non-natural amino acid, a fatty acid modification, esterification, or a combination thereof.

13. The method of claim 11, wherein the peptide or analog thereof has a length of 20 amino acids or less.

14. The method of claim 11, wherein the composition is a pharmaceutical composition further comprising a pharmaceutically acceptable carrier.

15. The method of claim 11, wherein the peptide or analog thereof consists of an amino acid sequence selected from the group consisting of:

| | |
|---|---|
| IGLHDPTQGTEPAG; | (SEQ ID NO: 118) |
| IGLHDPTQGTEPAGE; | (SEQ ID NO: 50) |
| IGLHDPTQGTEP(Aib)GE; | (SEQ ID NO: 51) |
| Ac-IGLHDPTQGTEPAGE; | (SEQ ID NO: 52) |
| (D-Ile)GLHDPTQGTEPAGE; | (SEQ ID NO: 53) |
| Ac-IGLHDPTQGTEPAG-NH2; | (SEQ ID NO: 60) |
| Ac-IGLHDPTQGTEPAGE-NH2; | (SEQ ID NO: 62) |
| IGLHDPTQGTEPAGE-NH2; | (SEQ ID NO: 68) |
| IGLHDPTQGTEPAGC; | (SEQ ID NO: 69) |
| Ac-IGLHDPTQGTEPAGC; | (SEQ ID NO: 70) |
| IGLHDPTQGTEPAGC-NH2; and | (SEQ ID NO: 71) |
| Ac-IGLHDPTQGTEPAGC-NH2. | (SEQ ID NO: 72) |

16. The method of claim 15, wherein the composition is a pharmaceutical composition further comprising a pharmaceutically acceptable carrier.

* * * * *

SEQUENCE LISTING

```
<160> NUMBER OF SEQ ID NOS: 118

<210> SEQ ID NO 1
<211> LENGTH: 15
<212> TYPE: PRT
<213> ORGANISM: Cricetulus sp.
<220> FEATURE:
<223> OTHER INFORMATION: N-term H
<220> FEATURE:
<223> OTHER INFORMATION: C-term OH

<400> SEQUENCE: 1

Ile Gly Leu His Asp Pro Ser His Gly Thr Leu Pro Asn Gly Ser
1               5                   10                  15

<210> SEQ ID NO 2
<211> LENGTH: 15
<212> TYPE: PRT
<213> ORGANISM: Homo sapiens
<220> FEATURE:
<223> OTHER INFORMATION: N-term H
<220> FEATURE:
<223> OTHER INFORMATION: C-term OH

<400> SEQUENCE: 2

Ile Gly Leu His Asp Pro Thr Gln Gly Thr Glu Pro Asn Gly Glu
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 3

Ser His Pro Asn Gly Ser Gly Thr Ile Gly Leu His Asp Pro Leu
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<223> OTHER INFORMATION: N-term H
<220> FEATURE:
<223> OTHER INFORMATION: C-term OH

<400> SEQUENCE: 4

Ser Ser Thr Gly Gly Gly Asp Ile Pro Pro His Leu Leu His Asn
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 5

Asp Gly Gly Thr Pro Gln Pro Gly Asn Trp Ile Glu Leu Thr His
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 6

Ile Gly Leu His Ala Pro Ser His Gly Thr Leu Pro Asn Gly Ser
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 7

Ile Gly Leu His Asp Pro Ser His Gly Thr Leu Pro Ala Gly Ser
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 8
```

```
Ile Gly Leu His Ala Pro Ser His Gly Thr Leu Pro Ala Gly Ser
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 9

Ile Gly Leu His Asp Pro Ser His Gly Thr Leu Pro Ala Gly Ser Lys
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (13)..(13)
<223> OTHER INFORMATION: Aib
<220> FEATURE:
<223> OTHER INFORMATION: C-term OH

<400> SEQUENCE: 10

Ile Gly Leu His Asp Pro Ser His Gly Thr Leu Pro Xaa Gly Ser
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (13)..(13)
<223> OTHER INFORMATION: N-methyl-L-Alanine
<220> FEATURE:
<223> OTHER INFORMATION: C-term OH

<400> SEQUENCE: 11

Ile Gly Leu His Asp Pro Ser His Gly Thr Leu Pro Ala Gly Ser
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term OH
```

```
<400> SEQUENCE: 12

Ile Gly Leu His Asp Pro Ser His Gly Thr Leu Pro Ala Gly Ser
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (1)..(1)
<223> OTHER INFORMATION: D-Isoleucine
<220> FEATURE:
<223> OTHER INFORMATION: C-term OH

<400> SEQUENCE: 13

Ile Gly Leu His Asp Pro Ser His Gly Thr Leu Pro Ala Gly Ser
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (1)..(1)
<223> OTHER INFORMATION: L-NorValine
<220> FEATURE:
<223> OTHER INFORMATION: C-term OH

<400> SEQUENCE: 14

Val Gly Leu His Asp Pro Ser His Gly Thr Leu Pro Ala Gly Ser
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (1)..(1)
<223> OTHER INFORMATION: L-NorLeucine
<220> FEATURE:
<223> OTHER INFORMATION: C-term OH

<400> SEQUENCE: 15

Leu Gly Leu His Asp Pro Ser His Gly Thr Leu Pro Ala Gly Ser
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term Ac
<220> FEATURE:
<223> OTHER INFORMATION: C-term OH

<400> SEQUENCE: 16

Ile Gly Leu His Asp Pro Ser His Gly Thr Leu Pro Asn Gly Ser
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (1)..(1)
<223> OTHER INFORMATION: D-Isoleucine
<220> FEATURE:
<223> OTHER INFORMATION: C-term OH

<400> SEQUENCE: 17

Ile Gly Leu His Asp Pro Ser His Gly Thr Leu Pro Asn Gly Ser
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 18

Ile Gly Leu His Asp Pro Ser His Gly Thr Glu Pro Asn Gly Ser
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 19

Ile Gly Leu His Asp Pro Ser Gln Gly Thr Leu Pro Asn Gly Ser
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
```

```
<223> OTHER INFORMATION: C-term OH

<400> SEQUENCE: 20

Ile Gly Leu His Asp Pro Thr His Gly Thr Leu Pro Asn Gly Ser
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 21

Ile Gly Leu His Asp Pro Ser His Gly Thr Leu Pro Asn Gly Glu
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 22

Ile Gly Leu His Asp Pro Ser His Gly Thr Leu Pro Asn Gly Lys
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 23

Ile Gly Leu His Asp Pro Ser His Gly Thr Leu Pro Ala Gly Lys
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 24

Ile Gly Leu His Asp Pro Ser His Gly Thr Glu Pro Ala Gly Ser
1               5                   10                  15
```

```
<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 25

Ile Gly Leu His Asp Pro Ser Gln Gly Thr Leu Pro Ala Gly Ser
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 26

Ile Gly Leu His Asp Pro Thr His Gly Thr Leu Pro Ala Gly Ser
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 27

Ile Gly Leu His Asp Pro Ser His Gly Thr Leu Pro Ala Gly Glu
1               5                   10                  15

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term NH2

<400> SEQUENCE: 28

Ile Gly Leu His Asp Pro Ser His Gly Thr Leu Pro Ala Gly
1               5                   10

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
```

```
                                       peptide
<220> FEATURE:
<223> OTHER INFORMATION: N-term Ac
<220> FEATURE:
<223> OTHER INFORMATION: C-term NH2

<400> SEQUENCE: 29

Ile Gly Leu His Asp Pro Ser His Gly Thr Leu Pro Ala Gly Ser
1               5                   10                  15

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 30

Ile Gly Leu His Asp Pro Ser His Gly Thr Leu Pro Ala Gly
1               5                   10

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 31

Ile Gly Leu His Asp Pro Ser His Gly Thr Leu Pro Asn Gly Ser
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term NH2

<400> SEQUENCE: 32

Ile Gly Leu His Asp Pro Ser His Gly Thr Leu Pro Asn Gly Ser
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 33
```

Ile Gly Leu His Asp Pro Ser His Gly Thr Leu Pro Asn Gly Ser Cys
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term OH

<400> SEQUENCE: 34

Ile Gly Leu His Asp Pro Ser His Gly Thr Leu Pro Asn Gly Ser Cys
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term NH2

<400> SEQUENCE: 35

Ile Gly Leu His Asp Pro Ser His Gly Thr Leu Pro Asn Gly Ser Cys
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 36

Ile Gly Leu His Asp Pro Ser His Gly Thr Leu Pro Asn Gly Ser Cys
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 37

Ile Gly Leu His Asp Pro Ser His Gly Thr Leu Pro Asn Gly Cys
1               5                   10                  15

<210> SEQ ID NO 38
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term OH

<400> SEQUENCE: 38

Ile Gly Leu His Asp Pro Ser His Gly Thr Leu Pro Asn Gly Cys
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term NH2

<400> SEQUENCE: 39

Ile Gly Leu His Asp Pro Ser His Gly Thr Leu Pro Asn Gly Cys
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 40

Ile Gly Leu His Asp Pro Ser His Gly Thr Leu Pro Asn Gly Cys
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term NH2

<400> SEQUENCE: 41

Ile Gly Leu His Asp Pro Ser His Gly Thr Leu Pro Ala Gly Ser
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
```

```
<220> FEATURE:
<223> OTHER INFORMATION: C-term OH

<400> SEQUENCE: 42

Ile Gly Leu His Asp Pro Ser His Gly Thr Leu Pro Ala Gly Ser Cys
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term OH

<400> SEQUENCE: 43

Ile Gly Leu His Asp Pro Ser His Gly Thr Leu Pro Ala Gly Ser Cys
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term NH2

<400> SEQUENCE: 44

Ile Gly Leu His Asp Pro Ser His Gly Thr Leu Pro Ala Gly Ser Cys
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 45

Ile Gly Leu His Asp Pro Ser His Gly Thr Leu Pro Ala Gly Ser Cys
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 46

Ile Gly Leu His Asp Pro Ser His Gly Thr Leu Pro Ala Gly Cys
1               5                   10                  15
```

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term OH

<400> SEQUENCE: 47

Ile Gly Leu His Asp Pro Ser His Gly Thr Leu Pro Ala Gly Cys
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term NH2

<400> SEQUENCE: 48

Ile Gly Leu His Asp Pro Ser His Gly Thr Leu Pro Ala Gly Cys
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 49

Ile Gly Leu His Asp Pro Ser His Gly Thr Leu Pro Ala Gly Cys
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 50

Ile Gly Leu His Asp Pro Thr Gln Gly Thr Glu Pro Ala Gly Glu
1               5                   10                  15

<210> SEQ ID NO 51
<211> LENGTH: 15
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (13)..(13)
<223> OTHER INFORMATION: Aib
<220> FEATURE:
<223> OTHER INFORMATION: C-term OH

<400> SEQUENCE: 51

Ile Gly Leu His Asp Pro Thr Gln Gly Thr Glu Pro Xaa Gly Glu
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term OH

<400> SEQUENCE: 52

Ile Gly Leu His Asp Pro Thr Gln Gly Thr Glu Pro Ala Gly Glu
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (1)..(1)
<223> OTHER INFORMATION: D-Isoleucine
<220> FEATURE:
<223> OTHER INFORMATION: C-term OH

<400> SEQUENCE: 53

Ile Gly Leu His Asp Pro Thr Gln Gly Thr Glu Pro Ala Gly Glu
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term OH

<400> SEQUENCE: 54

Ile Gly Leu His Asp Pro Thr Gln Gly Thr Glu Pro Asn Gly Glu
1               5                   10                  15

<210> SEQ ID NO 55
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (1)..(1)
<223> OTHER INFORMATION: D-Isoleucine
<220> FEATURE:
<223> OTHER INFORMATION: C-term OH

<400> SEQUENCE: 55

Ile Gly Leu His Asp Pro Thr Gln Gly Thr Glu Pro Asn Gly Glu
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 56

Ile Gly Leu His Asp Pro Thr Gln Gly Thr Glu Pro Asn Gly Ser
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 57

Ile Gly Leu His Asp Pro Thr Gln Gly Thr Glu Pro Ala Gly Ser
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 58

Ile Gly Leu His Asp Pro Thr Gln Gly Thr Leu Pro Asn Gly Glu
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term H
<220> FEATURE:
<223> OTHER INFORMATION: C-term OH

<400> SEQUENCE: 59

Ile Gly Leu His Asp Pro Thr Gln Gly Thr Leu Pro Ala Gly Glu
1               5                   10                  15

<210> SEQ ID NO 60
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 60

Ile Gly Leu His Asp Pro Thr Gln Gly Thr Glu Pro Ala Gly
1               5                   10

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 61

Ile Gly Leu His Asp Pro Thr Gln Gly Thr Glu Pro Asn Gly Glu
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 62

Ile Gly Leu His Asp Pro Thr Gln Gly Thr Glu Pro Ala Gly Glu
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term NH2

<400> SEQUENCE: 63
```

Ile Gly Leu His Asp Pro Thr Gln Gly Thr Glu Pro Asn Gly Glu
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 64

Ile Gly Leu His Asp Pro Thr Gln Gly Thr Glu Pro Asn Gly Cys
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term OH

<400> SEQUENCE: 65

Ile Gly Leu His Asp Pro Thr Gln Gly Thr Glu Pro Asn Gly Cys
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term NH2

<400> SEQUENCE: 66

Ile Gly Leu His Asp Pro Thr Gln Gly Thr Glu Pro Asn Gly Cys
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 67

Ile Gly Leu His Asp Pro Thr Gln Gly Thr Glu Pro Asn Gly Cys
1               5                   10                  15

<210> SEQ ID NO 68
<211> LENGTH: 15
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term NH2

<400> SEQUENCE: 68

Ile Gly Leu His Asp Pro Thr Gln Gly Thr Glu Pro Ala Gly Glu
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 69

Ile Gly Leu His Asp Pro Thr Gln Gly Thr Glu Pro Ala Gly Cys
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term OH

<400> SEQUENCE: 70

Ile Gly Leu His Asp Pro Thr Gln Gly Thr Glu Pro Ala Gly Cys
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term NH2

<400> SEQUENCE: 71

Ile Gly Leu His Asp Pro Thr Gln Gly Thr Glu Pro Ala Gly Cys
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
```

```
<223> OTHER INFORMATION: C-term NH2

<400> SEQUENCE: 72

Ile Gly Leu His Asp Pro Thr Gln Gly Thr Glu Pro Ala Gly Cys
1               5                   10                  15

<210> SEQ ID NO 73
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ile Gly Leu His Asp Pro Ser His Gly Thr Leu Pro Ala Gly
1               5                   10

<210> SEQ ID NO 74
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ile Gly Leu His Asp Pro Ser His Gly Thr Leu Pro Asn Gly
1               5                   10

<210> SEQ ID NO 75
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac

<400> SEQUENCE: 75

Ile Gly Leu His Asp Pro Ser His Gly Thr Leu Pro Asn Gly
1               5                   10

<210> SEQ ID NO 76
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 76

Ile Gly Leu His Asp Pro Ser His Gly Thr Leu Pro Asn Gly
1               5                   10

<210> SEQ ID NO 77
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2
```

```
<400> SEQUENCE: 77

Ile Gly Leu His Asp Pro Ser His Gly Thr Leu Pro Asn Gly
1               5                   10

<210> SEQ ID NO 78
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 78

Ile Gly Leu His Asp Pro Ser His Gly Thr Leu Pro Gln Gly Ser
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 79

Ile Gly Leu His Asp Pro Ser His Gly Thr Leu Pro Asp Gly Ser
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 80

Ile Gly Leu His Asp Pro Ser His Gly Thr Leu Pro Glu Gly Ser
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 81

Ile Gly Leu His Glu Pro Ser His Gly Thr Leu Pro Asn Gly Ser
1               5                   10                  15
```

```
<210> SEQ ID NO 82
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 82

Ile Gly Leu His Gln Pro Ser His Gly Thr Leu Pro Asn Gly Ser
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 83

Ile Gly Leu His Asn Pro Ser His Gly Thr Leu Pro Asn Gly Ser
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 84

Ile Gly Leu His Glu Pro Ser His Gly Thr Leu Pro Ala Gly Ser
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 85

Ile Gly Leu His Gln Pro Ser His Gly Thr Leu Pro Ala Gly Ser
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term H
<220> FEATURE:
<223> OTHER INFORMATION: C-term OH

<400> SEQUENCE: 86

Ile Gly Leu His Asn Pro Ser His Gly Thr Leu Pro Ala Gly Ser
1               5                   10                  15

<210> SEQ ID NO 87
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 87

Ile Gly Leu His Asp Pro Ser His Gly Thr Leu Pro Gln Gly Ser Cys
1               5                   10                  15

<210> SEQ ID NO 88
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 88

Ile Gly Leu His Asp Pro Ser His Gly Thr Leu Pro Asp Gly Ser Cys
1               5                   10                  15

<210> SEQ ID NO 89
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 89

Ile Gly Leu His Asp Pro Ser His Gly Thr Leu Pro Glu Gly Ser Cys
1               5                   10                  15

<210> SEQ ID NO 90
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 90
```

```
Ile Gly Leu His Glu Pro Ser His Gly Thr Leu Pro Asn Gly Ser Cys
1               5                   10                  15

<210> SEQ ID NO 91
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 91

Ile Gly Leu His Gln Pro Ser His Gly Thr Leu Pro Asn Gly Ser Cys
1               5                   10                  15

<210> SEQ ID NO 92
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 92

Ile Gly Leu His Asn Pro Ser His Gly Thr Leu Pro Asn Gly Ser Cys
1               5                   10                  15

<210> SEQ ID NO 93
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 93

Ile Gly Leu His Asp Pro Ser His Gly Thr Leu Pro Gln Gly
1               5                   10

<210> SEQ ID NO 94
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 94

Ile Gly Leu His Asp Pro Ser His Gly Thr Leu Pro Asp Gly
1               5                   10

<210> SEQ ID NO 95
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 95

Ile Gly Leu His Asp Pro Ser His Gly Thr Leu Pro Glu Gly
1               5                   10

<210> SEQ ID NO 96
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 96

Ile Gly Leu His Glu Pro Ser His Gly Thr Leu Pro Asn Gly
1               5                   10

<210> SEQ ID NO 97
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 97

Ile Gly Leu His Gln Pro Ser His Gly Thr Leu Pro Asn Gly
1               5                   10

<210> SEQ ID NO 98
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 98

Ile Gly Leu His Asn Pro Ser His Gly Thr Leu Pro Asn Gly
1               5                   10

<210> SEQ ID NO 99
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
```

<223> OTHER INFORMATION: C-term OH

<400> SEQUENCE: 99

Ile Gly Leu His Glu Pro Ser His Gly Thr Leu Pro Ala Gly
1               5                   10

<210> SEQ ID NO 100
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 100

Ile Gly Leu His Gln Pro Ser His Gly Thr Leu Pro Ala Gly
1               5                   10

<210> SEQ ID NO 101
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 101

Ile Gly Leu His Asn Pro Ser His Gly Thr Leu Pro Ala Gly
1               5                   10

<210> SEQ ID NO 102
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 102

Ile Gly Leu His Asp Pro Ser His Gly Thr Leu Pro Gln Gly Glu
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 103

Ile Gly Leu His Asp Pro Ser His Gly Thr Leu Pro Asp Gly Glu
1               5                   10                  15

```
<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 104

Ile Gly Leu His Asp Pro Ser His Gly Thr Leu Pro Glu Gly Glu
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 105

Ile Gly Leu His Glu Pro Ser His Gly Thr Leu Pro Asn Gly Glu
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 106

Ile Gly Leu His Gln Pro Ser His Gly Thr Leu Pro Asn Gly Glu
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 107

Ile Gly Leu His Asn Pro Ser His Gly Thr Leu Pro Asn Gly Glu
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<223> OTHER INFORMATION: N-term H
<220> FEATURE:
<223> OTHER INFORMATION: C-term OH

<400> SEQUENCE: 108

Ile Gly Leu His Glu Pro Ser His Gly Thr Leu Pro Ala Gly Glu
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 109

Ile Gly Leu His Gln Pro Ser His Gly Thr Leu Pro Ala Gly Glu
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 110

Ile Gly Leu His Asn Pro Ser His Gly Thr Leu Pro Ala Gly Glu
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ile, D-Isoleucine, L-NorValine or L-NorLeucine
<220> FEATURE:
<221> NAME/KEY: MOD_RES
<222> LOCATION: (5)..(5)
<223> OTHER INFORMATION: Ala or Asp
<220> FEATURE:
<221> NAME/KEY: MOD_RES
<222> LOCATION: (7)..(7)
<223> OTHER INFORMATION: Ser or Thr
<220> FEATURE:
<221> NAME/KEY: MOD_RES
<222> LOCATION: (8)..(8)
<223> OTHER INFORMATION: His or Gln
<220> FEATURE:
<221> NAME/KEY: MOD_RES
<222> LOCATION: (11)..(11)
<223> OTHER INFORMATION: Leu or Glu
<220> FEATURE:
<221> NAME/KEY: MOD_RES
<222> LOCATION: (13)..(13)
<223> OTHER INFORMATION: Ala, Asn, alpha-amino-isobutyric acid or
```

```
          N-methyl-L-Alanine
<220> FEATURE:
<223> OTHER INFORMATION: See specification as filed for detailed
      description of substitutions and preferred embodiments

<400> SEQUENCE: 111

Xaa Gly Leu His Xaa Pro Xaa Xaa Gly Thr Xaa Pro Xaa Gly Ser
1               5                   10                  15

<210> SEQ ID NO 112
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Ser, Glu, Cys or Lys
<220> FEATURE:
<221> NAME/KEY: MOD_RES
<222> LOCATION: (16)..(16)
<223> OTHER INFORMATION: May or may not be present
<220> FEATURE:
<223> OTHER INFORMATION: See specification as filed for detailed
      description of substitutions and preferred embodiments

<400> SEQUENCE: 112

Ile Gly Leu His Asp Pro Ser His Gly Thr Leu Pro Asn Gly Xaa Cys
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Ser, Glu, Cys, Lys or absent
<220> FEATURE:
<223> OTHER INFORMATION: see specification as filed for detailed
      description of substitutions and preferred embodiments

<400> SEQUENCE: 113

Ile Gly Leu His Asp Pro Ser His Gly Thr Leu Pro Ala Gly Xaa
1               5                   10                  15

<210> SEQ ID NO 114
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Lys or Cys
<220> FEATURE:
<223> OTHER INFORMATION: see specification as filed for detailed
      description of substitutions and preferred embodiments

<400> SEQUENCE: 114

Ile Gly Leu His Asp Pro Ser His Gly Thr Leu Pro Ala Gly Ser Xaa
1               5                   10                  15

<210> SEQ ID NO 115
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ile or D-Isoleucine
<220> FEATURE:
<221> NAME/KEY: MOD_RES
<222> LOCATION: (11)..(11)
<223> OTHER INFORMATION: Glu or Leu
<220> FEATURE:
<221> NAME/KEY: MOD_RES
<222> LOCATION: (13)..(13)
<223> OTHER INFORMATION: Ala, Asn or alpha-amino-isobutyric acid
<220> FEATURE:
<223> OTHER INFORMATION: See specification as filed for detailed
      description of substitutions and preferred embodiments

<400> SEQUENCE: 115

Xaa Gly Leu His Asp Pro Thr Gln Gly Thr Xaa Pro Xaa Gly Glu
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Ser, Glu or Cys
<220> FEATURE:
<223> OTHER INFORMATION: see specification as filed for detailed
      description of substitutions and preferred embodiments

<400> SEQUENCE: 116

Ile Gly Leu His Asp Pro Thr Gln Gly Thr Glu Pro Asn Gly Xaa
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Ser, Cys or absent
<220> FEATURE:
<223> OTHER INFORMATION: see specification as filed for detailed
      description of substitutions and preferred embodiments

<400> SEQUENCE: 117

Ile Gly Leu His Asp Pro Thr Gln Gly Thr Glu Pro Ala Gly Xaa
1               5                   10                  15

<210> SEQ ID NO 118
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 118

Ile Gly Leu His Asp Pro Thr Gln Gly Thr Glu Pro Ala Gly
1               5                   10
```